(12) United States Patent
Rathore et al.

(10) Patent No.: US 7,438,916 B2
(45) Date of Patent: Oct. 21, 2008

(54) THERAPEUTIC TARGET FOR PROTOZOAL DISEASES

(75) Inventors: Dharmendar Rathore, Blacksburg, VA (US); Dewal Jani, Blacksburg, VA (US); Rana Nagarkatti, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 185 days.

(21) Appl. No.: 11/249,355

(22) Filed: Oct. 14, 2005

(65) Prior Publication Data

US 2007/0087012 A1 Apr. 19, 2007

(51) Int. Cl.
*A61K 39/002* (2006.01)
*A61K 39/015* (2006.01)
*C07H 21/04* (2006.01)
*C07K 14/445* (2006.01)
*C12N 15/30* (2006.01)

(52) U.S. Cl. .............. 424/191.1; 424/185.1; 424/265.1; 424/268.1; 424/272.1; 530/300; 530/350; 536/23.1; 536/23.7; 435/69.1; 435/69.3; 435/172.3; 435/320.1

(58) Field of Classification Search .............. 424/191.1, 424/185.1, 265.1, 268.1, 272.1; 530/300, 530/350; 435/69.1, 69.3, 172.3, 320.1; 536/23.1, 536/23.7
See application file for complete search history.

(56) References Cited

FOREIGN PATENT DOCUMENTS

WO WO02/77195 A2 3/2002

OTHER PUBLICATIONS

Matuschewski et al J. Biol. Chem., vol. 277, Issue 44, 41948-41953, Nov. 1, 2002.*

* cited by examiner

*Primary Examiner*—Shanon A. Foley
*Assistant Examiner*—Padma v Baskar
(74) *Attorney, Agent, or Firm*—Whitham Curtis Christofferson & Cook, PC

(57) ABSTRACT

A novel Fasciclin Related Adhesive Protein (FRAP) from *Plasmodium* and related parasites is provided as a target for therapeutic intervention in diseases caused by the parasites. FRAP has been shown to play a critical role in adhesion to, or invasion into, host cells by the parasite. Furthermore, FRAP catalyzes the neutralization of heme by the parasite, by promoting its polymerization into hemozoin. This invention provides methods and compositions for therapies based on the administration of protein, DNA or cell-based vaccines and/or antibodies based on FRAP, or antigenic epitopes of FRAP, either alone or in combination with other parasite antigens. Methods for the development of compounds that inhibit the catalytic activity of FRAP, and diagnostic and laboratory methods utilizing FRAP are also provided.

16 Claims, 18 Drawing Sheets

*P. falciparum* (SEQ ID NO: 1)
MKNRFYYNLIIKRLYTRSGGLRKPQKVTNDPESINRKVYWCFEHKPVKRTIINLIYSHNEL
KIFSNLLNHPTVGSSLIHELSLDGPYTAFFPSNEAMQLINIESFNKLYNDENKLSEFVLNHV
TKEYWLYRDLYGSSYQPWLMYNEKREAPEKLRNLLNNDLIVKIEGEFKHCNHSIYLNGS
KIIRPNMKCHNGVVHIVDKPIIF

*Figure 1A*

*P. gallinaceum* (SEQ ID NO: 3)
MKNSGYNLIIKRLYTRSGGLRKPQKVTNDPESINRKVYWCFEHKPIKRTIVNLIFSHKELK
FFSNFLNHPNVGVSLIHELSLEGPFTGFLPSNEALKLINSECLNKLYKDDNKLSEFVLNHFT
KDFWLYRDLYGSSYQPWLIYNEKREAPEKITNLMNNDLIVKIKGEFKNCDHSIYLNESKII
RPNMKCHNGVVHIVDKPIIF

*Figure 1B*

*P. reichenowi* (SEQ ID NO: 5)
MKIKFYNLISKRLYTRSGGLRKPQKVTNDPESINRKVYWCFEHKPVKRTIINLIYSHNELK
IFSNLLNHPIVGSSLIHELSLDGPYTAFLPSNEAMKLINIESFNKLYNDENKLSEFVLNHVT
KEYWLYRDLYGSSYQPWLMYNEKREAPEKLRNLLNNDIIVKIEGEFKHCNHSIYLNGSKI
IRPNMKCHNGVVHIVDKPIIF

*Figure 1C*

*P. vivax* (SEQ ID NO: 7)
MKKSRPPFLVIKRLYTRSGGLRKPQKVTNDPESINRKTYWCFEHKPIKRTLVNLIYSHNEL
KLFSRFLNHPNVGTSLVHELSLEGPYTGFLPSNEALKLISPESLAKLYEEGDKLMEFVLGH
FAKDFWLYRDLYGSSYQPWLVFNERRDAPEKITNLVNRDLLVEITGEFKNCDHSISLNGA
KIIRPNMKCHNGVVHIVDRPIIQR

*Figure 1D*

*P. yoelii* (SEQ ID NO: 9)
MKKKLYNLVLKRSYTRSGGLRKPQKVTNDPESINRKVYWCFEHKPVRRTVINLIFSHNE
LKNFSTLLRNTNASSSLIHELSLEGPYTGFLPSDEALNLLSTNSLNKLYKDDNKMSEFVLN
HFTKGLWMYRDLYGSSYQPWLMYNEKREAPEKIQTLVNNDIIVKIEGEFKNCDHSIYLN
EAKIIRPNMKCHNGIIHIIDKPIIF

*Figure 1E*

*P. knowlesi*  (SEQ ID NO: 11)
MKKSHPPFLIIKRLYTRSGGLRKPQKVTNDPESINRKTYWCFEHKPIKRTMVNLIYSHNEL
KLFSRFLSHPNVGTSLIHELSLEGPYTGFLPSNEALKLISPESLAKLYEQRDKLMEFVLGHF
TKDFWLYRDLYRSSYHPWLVFNEKREAPEKITNLVNKDLLVKITGEFKNCDHSIFLNGA
KIITPNMKCHNGVVHIVDRPIIQR

Figure 1F

*P. chaubaudi*  (SEQ ID NO: 13)
MKKKLYNLVLKRNYTRCGGLRRPQKVTNDPESINRKVYWCFEHKPVRRTVINLIFSHNE
LKNFSTLLRNTNASSSLIHELSLEGPYTGFLPSDEALNLLSANSLNKLYNDDNKMSEFVLN
HFTKGLWMYRDLYGSSYQPWLMYNEKRDAPEKLTTLINNDIIVKIEGEFKNCDHSIYLNE
AKIIRPNMKCHNGIIHIIDKPIIF

Figure 1G

*P. berghei*  (SEQ ID NO: 15)
MKKKLYNLVLKRNYTRSGGLRKPQKVTNDPESINRKVYWCFEHKPVRRTVINLIFSHNE
LKNFSTLLKNTNASSSLIHELSLEGPYTGFLPSDEALNLLSTNSLNKLYKDDNKMSEFVLN
HFTKGLWMYRDLYGSSYQPWLMYNEKREAPEKIPTLVNNDIIVKIEGEFKNCDHSIYLNE
AKIIRPNMKCHNGIIHIIDKPIIF

Figure 1H

*T. parva*  (SEQ ID NO: 17)
MFISQALLWRSNFGGLKKLRRVTKDPNVINSKVYWCFEHKYIRRTVLSFCNNNPFTRSFS
SLINPEEESGYRLSHELSLPGPFTGFIPVNEGLTQALSKLEASYKDSVVDFVRSHFTHNLW
LYRDILGSPTQPWLLYNKTRKFPEKLQTINNKSLFFEHTGDLSKGDKEIFVNGSKILRWNL
RCHNGVIHLIDKPLFDI

Figure 1I

*T. annulata*  (SEQ ID NO: 19)
MFLTCYFHFMMFTSKALSWRSNFGGLKKLRRRSKDPNVINSKVYWCFEHKYIRRTVLSF
CNNNPFTRSFSKLINPEEESGIFYFLSHVLGYRLSHELSLPGPFTGFIPVNEGLTQALPKLES
SYKDAVVDFVRSHFTHHLWLHRDLLGSPTQPWLLYNKTRKFPKKLQTLNNKSLFFEHTG
DLSKGDKEIFVNGSRILRWNMRCHNGVIHLIDKPLFDI

Figure 1J

*P. falciparum* (SEQ ID NO: 2)
ATGAAAAATAGATTTTATTATAATTTGATAATTAAAAGATTATATACACGAAGTGGC
GGTTTAAGAAAACCTCAAAAGGTAACCAACGACCCAGAAAGTATAAATAGAAAA
GTATATTGGTGTTTTGAACATAAGCCTGTAAAAAGGACAATTATTAATTTAATATAT
TCACATAACGAACTCAAGATATTTTCTAATCTGTTAAATCATCCTACAGTTGGCAG
CTCGTTAATACATGAATTATCTCTCGATGGCCCTTATACTGCATTTTTTCCCTCCAA
CGAAGCCATGCAATTAATAAATATAGAAAGTTTCAATAAATTGTATAACGATGAAA
ATAAATTATCAGAATTTGTTTTAAATCACGTTACGAAAGAATATTGGCTGTATAGAG
ATTTATATGGTTCATCTTACCAACCGTGGTTAATGTACAATGAAAAAAGGGAAGCT
CCAGAAAAATTAAGAAATTTATTGAATAATGATTTAATAGTAAAAATTGAGGGGGA
ATTTAAACATTGCAATCATTCGATATATTTAAATGGCTCAAAAATTATAAGACCAAA
TATGAAGTGCCACAATGGAGTTGTGCATATAGTAGATAAGCCCATCATTTTTTAA

Figure 2A

*P. gallinaceum* (SEQ ID NO: 4)
ATGAAAAATAGTGGTTATAATTTAATTATTAAAAGACTATATACTCGTAGTGGTGGA
TTACGAAAACCACAAAAAGTAACTAATGATCCAGAAAGTATTAATAGAAAGTTT
ATTGGTGTTTTGAACATAAACCTATTAAAAGGACAATTGTTAATTTAATATTTTCAC
ATAAGGAATTGAAATTTTTCTCTAATTTTTTAAACCATCCAAATGTTGGCGTATCAT
TAATCCATGAATTATCTTTAGAGGGACCATTCACAGGATTTTTACCATCAAATGAA
GCATTAAAGTTAATTAATTCAGAATGTTTAAATAAATTATATAAGGATGATAATAAA
TTATCTGAATTTGTTTTAAATCATTTTACAAAAGATTTTTGGCTATATAGAGATTTAT
ATGGATCATCATACCAGCCTTGGTTAATATATAATGAAAAAAGAGAAGCACCAGAA
AAAATCACTAACTTAATGAATAATGATTTAATAGTAAAAATAAAAGGGGAATTTAA
AAATTGTGATCATTCAATTTATTTAAACGAATCAAAAATTATCAGACCTAATATGAA
ATGTCACAATGGTGTAGTTCATATTGTAGATAAGCCAATAATATTT

Figure 2B

*P. reichenowi* (SEQ ID NO: 6)
ATGAAAATTAAATTTTATAATTTGATAAGTAAAAGATTATATACTCGAAGTGGTGGT
TTAAGAAAGCCTCAAAAGGTAACAAACGACCCAGAAAGTATAAATAGAAAGTAT
ATTGGTGTTTTGAACATAAGCCTGTAAAAAGGACAATTATTAATTTAATATATTCAC
ATAACGAACTCAAGATATTCTCTAATCTGTTAAATCATCCTATAGTTGGTAGCTCGT
TAATACATGAATTATCTCTCGATGGCCCTTATACTGCATTTCTTCCCTCCAACGAAG
CCATGAAATTAATAAATATAGAAAGTTTCAATAAATTGTATAACGATGAAAATAAAT
TATCAGAATTTGTTTTAAATCACGTTACGAAAGAATATTGGCTGTATAGAGATTTAT
ATGGTTCTTCTTACCAACCGTGGTTAATGTACAATGAAAAAAGGGAAGCTCCAGA
AAAATTAAGAAATTTATTGAATAATGATATAATAGTAAAAATTGAGGGGGAATTTAA
ACATTGCAATCATTCGATATATTTAAATGGTTCAAAAATTATAAGACCAAATATGAA
GTGCCACAATGGAGTTGTGCATATAGTAGATAAGCCCATCATTTT

Figure 2C

*P. vivax* (SEQ ID NO: 8)
ATGAAAAAGAGCCGCCCACCCTTCCTTGTCATTAAAAGGCTATACACACGCAGTGG
CGGATTGAGGAAACCGCAAAAAGTGACGAACGATCCCGAAAGCATTAATCGAAAA
ACGTACTGGTGCTTTGAACACAAACCTATTAAGAGGACGTTGGTCAATTTGATATAC
TCTCATAATGAATTGAAATTATTCTCCCGTTTTCTTAATCACCCCAATGTGGGTACCT
CCCTTGTACACGAGCTTTCCTTGGAAGGCCCCTACACGGGGTTCCTGCCTTCGAAC
GAGGCTCTGAAATTGATTAGCCCCGAGAGTTTAGCCAAATTGTATGAAGAAGGAGA
CAAGTTGATGGAATTCGTTTTGGGCCACTTCGCGAAGGACTTCTGGCTCTACAGGG
ACCTGTACGGGTCGTCCTACCAGCCCTGGCTCGTGTTCAACGAGAGGAGGGACGCC
CCTGAGAAAATCACCAACTTAGTTAACAGAGACCTACTTGTAGAGATAACAGGAGA
GTTTAAAAATTGCGACCACTCGATTTCCCTGAATGGAGCGAAGATCATCAGACCGAA
CATGAAGTGCCACAACGGAGTGGTGCACATTGTAGACAGGCCGATAATACAGAGG

Figure 2D

*P. yoelii* (SEQ ID NO: 10)
ATGAAAAAAAAATTGTATAATTTAGTTCTTAAAAGAAGTTACACACGTAGTGGCGGT
TTAAGAAAACCACAAAAAGTAACAAATGATCCAGAAAGTATTAATAGAAAGGTTTAT
TGGTGTTTTGAACATAAACCTGTTAGGAGGACTGTAATTAATTTAATATTTTCCCATAA
TGAATTAAAAAACTTTTCAACTCTTTTAAGAAATACAAATGCTAGCTCATCGCTAATT
CACGAGCTGTCATTGGAAGGGCCTTATACGGGATTTCTTCCATCAGACGAAGCCTTA
AATTTATTGAGTACAAATAGTTTAAATAAATTATATAAAGATGATAATAAAATGTCTGA
GTTTGTTTTAAATCATTTTACTAAAGGTCTGTGGATGTATAGAGATTTATATGGCTCAT
CCTATCAGCCATGGCTAATGTATAATGAAAAAAGAGAGGCCCCAGAAAAAATACAA
ACTTTAGTAAATAACGACATAATTGTAAAAATAGAAGGGGAATTTAAAAATTGTGAT
CATTCTATATATTTAAATGAAGCAAAAATTATAAGACCCAATATGAAATGTCATAATG
GCATAATTCATATCATAGATAAGCCAATAATTTTT

Figure 2E

*P. knowlesi* (SEQ ID NO: 12)
ATGAAAAAGAGCCACCCCCCCTTCCTTATCATTAAAAGGTTATACACACGCAGTGGA
GGATTGAGGAAACCACAAAAAGTGACGAACGATCCCGAAAGCATTAACAGAAAAA
CATACTGGTGCTTCGAACACAAACCTATTAAAAGGACGATGGTCAATTTGATATACTC
CCACAATGAACTGAAATTATTTTCCCGCTTTCTGAGTCATCCCAATGTCGGTACCTCC
CTCATACACGAGCTATCCTTGGAAGGCCCCTATACRGGGTTCCTGCCTTCGAACGAA
GCTCTGAAATTAATTAGCCCCGAAAGCTTAGCCAAATTATATgAACAAAGAGATAAA
TTGATGGAATTTGTTTTGGGGCACTTTACGAAAGACTTCTGGCTCTACAGAGATCTC
TACAGATCTTCCTACCATCCCTGGCTCGTATTTAACGAGAAAAGGGAAGCCCCTGAG
AAAATCACCAACTTAGTTAACAAAGACCTACTTGTAAAAATAACAGGAGAGTTTAAA
AATTGCGATCACTCCATTTTCCTTAATGGAGCGAAGATCATCACACCAAATATGAAG
TGCCACAACGGAGTGGTCCATATTGTAGACAGGCCGATTATACAGAGG

Figure 2F

*P. chaubaudi* (SEQ ID NO: 14)
ATGAAAAAAAAATTGTATAATTTAGTTCTTAAAAGAAATTACACACGCTGTGGCGGT
TTAAGAAGACCACAAAAAGTAACAAATGATCCAGAGAGTATTAATAGAAAGGTTTA
TTGGTGTTTTGAACATAAACCTGTTAGGAGGACTGTAATTAATTTAATATTTTCCCAT
AATGAATTAAAAAACTTTTCAACTCTTTTAAGGAATACAAATGCTAGCTCATCGCTA
ATTCACGAACTGTCATTGGAAGGACCTTATACGGGATTTCTTCCTTCAGACGAGGC
CTTAAATTTATTGAGTGCAAATAGCTTAAATAAATTATATAATGATGATAATAAAATG
TCTGAATTCGTTTTAAATCATTTTACTAAAGGTCTGTGGATGTACAGAGATTTATAT
GGCTCATCCTATCAGCCATGGCTCATGTACAATGAAAAAAGAGACGCCCCAGAAA
AATTAACAACTTTAATAAACAACGACaTAATTGTAAAAATAGAAGGAGAATTTAAA
AATTGTGATCATTCCATATATTTAAATGAAGCAAAAATTATAAGGCCCAATATGAAA
TGCCACAATGGCATAATTCATATCAtAGATaAGCCAATCATTTTT

Figure 2G

*P. berghei* (SEQ ID NO: 16)
ATGAAAAAAAAATTGTATAATTTAGTTCTTAAAAGAAATTACACGCGTAGTGGCGGT
TTAAGAAAACCACAAAAAGTAACAAATGATCCAGAAAGTATTAATAGAAAGGTTTA
TTGGTGTTTTGAGCATAAACCTGTTAGGAGGACTGTAATTAATTTAATATTTTCCCAT
AATGAATTAAAAAACTTTTCAACTCTTTTAAAAAATACAAATGCTAGCTCATCGCTA
ATTCACGAACTATCATTGGAAGGGCCTTATACGGGATTTCTTCCTTCGGATGAGGCC
TTAAATTTATTGAGTACAAATAGTTTAAATAAATTATATAAAGATGATAATAAAATGTC
TGAATTTGTTTTAAATCATTTTACTAAAGGTCTGTGGATGTATAGAGATTTATATGGCT
CATCCTATCAGCCATGGCTCATGTACAATGAAAAAAGAGAGGCCCCAGAAAAAATA
CCAACTTTAGTAAACAACGACATAATTGTAAAAATAGAAGGGGAATTTAAAAATTG
TGATCATTCTATATATTTAAATGAAGCAAAAATTATAAGACCCAATATGAAATGTCAT
AATGGCATAATTCATATCATAGATAAGCCAATAATTTTT

*Figure 2H*

*T. parva* (SEQ ID NO: 18)
ATGTTTATCTCTCAGGCCCTGTTGTGGAGATCTAATTTTGGAGGCTTGAAAAAGTTG
AGAAGAGTAACAAAGGACCCGAACGTCATAAATTCAAAGGTTTACTGGTGTTTTGA
ACATAAATATATTCGCCGTACTGTTCTTTCATTCTGTAATAACAACCCCTTTACGCGT
TCTTTTTCAAGTTTAATAAATCCTGAGGAGGAATCTGGCTATAGGTTATCTCACGAG
TTATCACTTCCAGGGCCTTTTACAGGCTTTATTCCAGTAAATGAGGGCTTAACTCAG
GCTTTATCAAAGCTAGAGGCTTCATACAAGGATTCTGTCGTTGATTTCGTGAGGTCC
CATTTTACACATAACTTATGGCTATATCGTGACATACTAGGTTCTCCAACCCAGCCCT
GGTTATTGTACAATAAAACTCGAAAATTTCCAGAAAAACTTCAAACCATTAATAACA
AATCTTTGTTCTTCGAACACACTGGAGACTTGTCAAAGGGTGATAAGGAAATCTTT
GTAAACGGTTCAAAGATACTTCGCTGGAACCTGAGATGTCATAATGGAGTTATTCAC
CTGATAGATAAACCTCTTTTCGATATCTAA

*Figure 2I*

*T. annulata* (SEQ ID NO: 20)
ATGTTTTTAACTTGTTATTTTCATTTTATGATGTTTACTTCCAAGGCCTTGTCGTGGAG
ATCTAATTTTGGAGGGTTAAAGAAGTTAAGGAGAAGATCAAAGGATCCAAACGTCAT
AAATTCAAAGGTTTATTGGTGTTTTGAGCATAAATATATTCGCCGTACAGTTCTTTCAT
TTTGTAATAATAATCCATTTACACGTTCATTTTCAAAGTTAATAAATCCCGAGGAAGAA
TCAGGTATTTTTTATTTTTTAAGCCATGTTTAGGTTATAGATTATCTCACGAGTTATCA
CTTCCCGGGCCTTTTACGGGCTTCATTCCAGTAAATGAAGGCTTAACACAGGCCTTAC
CGAAGCTGGAGTCCTCATACAAGGATGCGGTAGTTGATTTCGTAAGGTCTCACTTTAC
CCATCATTTATGGCTACATCGTGATCTGCTAGGCTCACCAACACAGCCCTGGCTACTGT
ATAACAAAACTCGCAAATTTCCAAAAAAACTACAAACCCTTAATAACAAATCTTTGTT
CTTCGAACACACAGGAGATCTGTCAAAGGGTGATAAGGAAATCTTTGTAATGGATC
AAGGATACTTCGCTGGAACATGAGATGTCATAATGGAGTTATTCACCTGATAGATAAA
CCCCTCTTTGATATTTAG

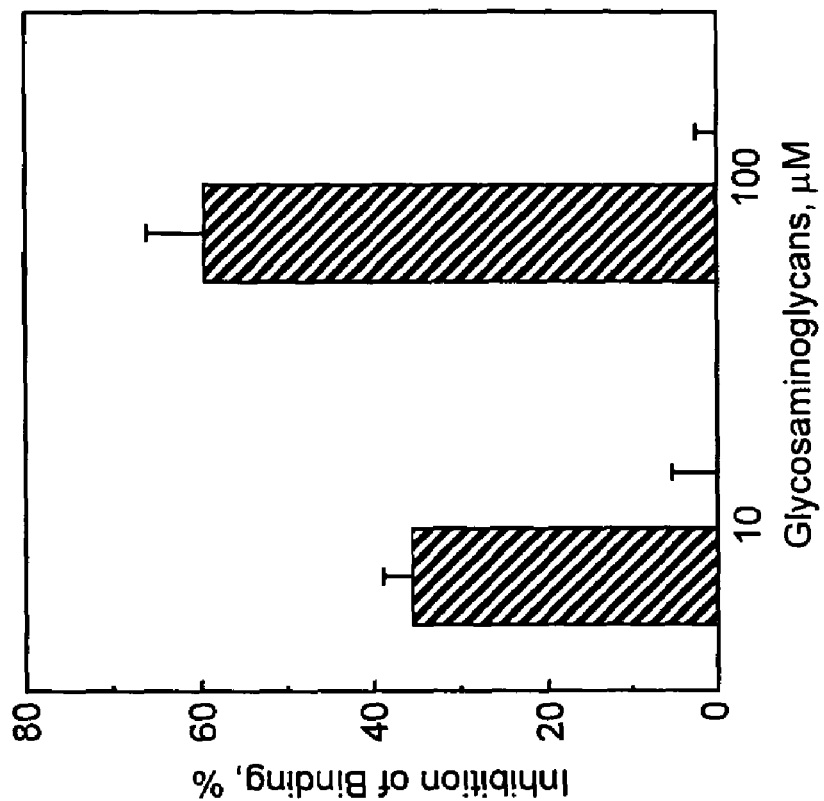
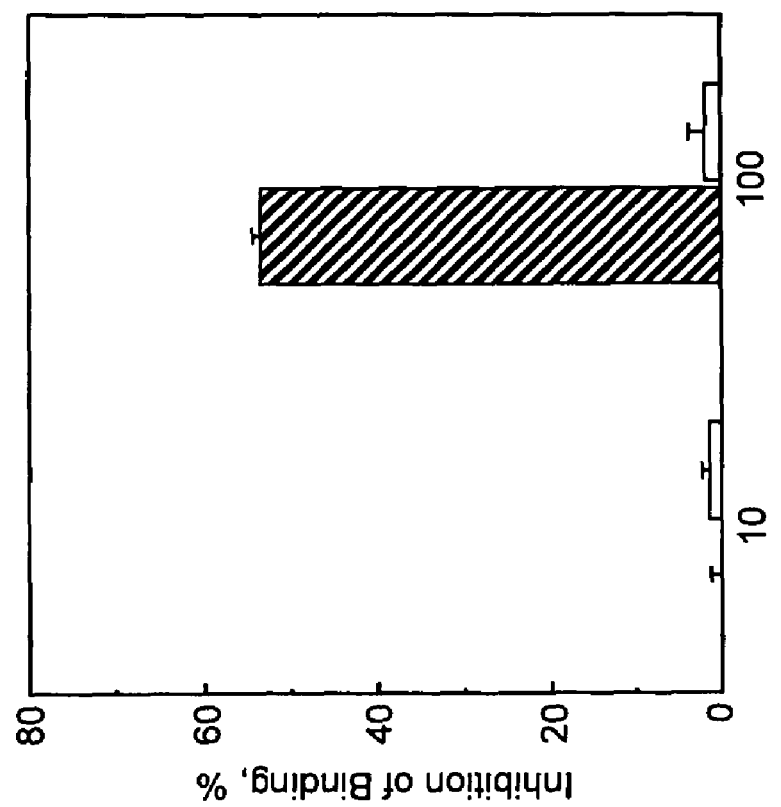

HAI-1: MKNRFYYNLIIKRLYTRSGG
HAI-2: NLIIKRLYTRSGGLRKPQKV
HAI-3: TRSGGLRKPQKVTNDPESIN
HAI-4: GLRKPQKVTNDPESINRKVY
HAI-5: TNDPESINRKVYWCFEHKPV
HAI-6: VYWCFEHKPVKRTIINLIYS
HAI-7: KPVKRTIINLIYSHNELKIF
HAI-8: NLIYSHNELKIFSNLLNHPT
HAI-9: NELKIFSNLLNHPTVGSSLI
HAI-10: NLLNHPTVGSSLIHELSLDG

Figure 7

ATGAAAAATAGATTTTATTATAATTTGATAATTAAAAGATTATATACACGAAGTGGCGG
TTTAAGAAAACCTCAAAAGGTAACCAACGACCCAGAAAGTATAAATAGAAAAGTATA
TTGGTGTTTTGAACATAAGCCTGTAAAAAGGACAATTATTAATTTAATATATTCACATAA
CGAACTCAAGATATTTTCTAATCTGTTAAATCATCCTACAGTTGGCAGCTCGTTAATAC
ATGAATTATCTCTCGATGGCCCTTAT

Figure 15A

MKNRFYYNLIIKRLYTRSGGLRKPQKVTNDPESINRKVYWCFEHKPVKRTIINLIYSHNE
LKIFSNLLNHPTVGSSLIHELSLDGPY

Figure 15B

SEQUENCE LISTING

<160> NUMBER OF SEQ ID NOS: 39

<210> SEQ ID NO 1
<211> LENGTH: 205
<212> TYPE: PRT
<213> ORGANISM: Plasmodium falciparum

<400> SEQUENCE: 1

```
Met Lys Asn Arg Phe Tyr Tyr Asn Leu Ile Ile Lys Arg Leu Tyr Thr
1               5                   10                  15

Arg Ser Gly Gly Leu Arg Lys Pro Gln Lys Val Thr Asn Asp Pro Glu
            20                  25                  30

Ser Ile Asn Arg Lys Val Tyr Trp Cys Phe Glu His Lys Pro Val Lys
        35                  40                  45

Arg Thr Ile Ile Asn Leu Ile Tyr Ser His Asn Glu Leu Lys Ile Phe
    50                  55                  60

Ser Asn Leu Leu Asn His Pro Thr Val Gly Ser Ser Leu Ile His Glu
65                  70                  75                  80

Leu Ser Leu Asp Gly Pro Tyr Thr Ala Phe Phe Pro Ser Asn Glu Ala
            85                  90                  95

Met Gln Leu Ile Asn Ile Glu Ser Phe Asn Lys Leu Tyr Asn Asp Glu
            100                 105                 110

Asn Lys Leu Ser Glu Phe Val Leu Asn His Val Thr Lys Glu Tyr Trp
        115                 120                 125

Leu Tyr Arg Asp Leu Tyr Gly Ser Ser Tyr Gln Pro Trp Leu Met Tyr
    130                 135                 140

Asn Glu Lys Arg Glu Ala Pro Glu Lys Leu Arg Asn Leu Leu Asn Asn
145                 150                 155                 160

Asp Leu Ile Val Lys Ile Glu Gly Glu Phe Lys His Cys Asn His Ser
                165                 170                 175

Ile Tyr Leu Asn Gly Ser Lys Ile Ile Arg Pro Asn Met Lys Cys His
            180                 185                 190

Asn Gly Val Val His Ile Val Asp Lys Pro Ile Ile Phe
        195                 200                 205
```

<210> SEQ ID NO 2
<211> LENGTH: 618
<212> TYPE: DNA
<213> ORGANISM: Plasmodium falciparum

<400> SEQUENCE: 2

```
atgaaaaata gattttatta taatttgata attaaaagat tatatacacg aagtggcggt      60
ttaagaaaac ctcaaaaggt aaccaacgac ccagaaagta aaatagaaa agtatattgg     120
```

-continued

```
tgttttgaac ataagcctgt aaaaaggaca attattaatt taatatattc acataacgaa    180
ctcaagatat tttctaatct gttaaatcat cctacagttg gcagctcgtt aatacatgaa    240
ttatctctcg atggcccttta tactgcattt tttccctcca acgaagccat gcaattaata    300
aatatagaaa gtttcaataa attgtataac gatgaaaata aattatcaga atttgtttta    360
aatcacgtta cgaaagaata ttggctgtat agagatttat atggttcatc ttaccaaccg    420
tggttaatgt acaatgaaaa aagggaagct ccagaaaaat taagaaattt attgaataat    480
gatttaatag taaaaattga gggggaattt aaacattgca atcattcgat atatttaaat    540
ggctcaaaaa ttataagacc aaatatgaag tgccacaatg gagttgtgca tatagtagat    600
aagcccatca ttttttaa                                                  618
```

<210> SEQ ID NO 3
<211> LENGTH: 204
<212> TYPE: PRT
<213> ORGANISM: Plasmodium gallinaceum

<400> SEQUENCE: 3

```
Met Lys Asn Ser Gly Tyr Asn Leu Ile Ile Lys Arg Leu Tyr Thr Arg
1               5                   10                  15

Ser Gly Gly Leu Arg Lys Pro Gln Lys Val Thr Asn Asp Pro Glu Ser
            20                  25                  30

Ile Asn Arg Lys Val Tyr Trp Cys Phe Glu His Lys Pro Ile Lys Arg
        35                  40                  45

Thr Ile Val Asn Leu Ile Phe Ser His Lys Glu Leu Lys Phe Phe Ser
    50                  55                  60

Asn Phe Leu Asn His Pro Asn Val Gly Val Ser Leu Ile His Glu Leu
65                  70                  75                  80

Ser Leu Glu Gly Pro Phe Thr Gly Phe Leu Pro Ser Asn Glu Ala Leu
                85                  90                  95

Lys Leu Ile Asn Ser Glu Cys Leu Asn Lys Leu Tyr Lys Asp Asp Asn
            100                 105                 110

Lys Leu Ser Glu Phe Val Leu Asn His Phe Thr Lys Asp Phe Trp Leu
        115                 120                 125

Tyr Arg Asp Leu Tyr Gly Ser Ser Tyr Gln Pro Trp Leu Ile Tyr Asn
    130                 135                 140

Glu Lys Arg Glu Ala Pro Glu Lys Ile Thr Asn Leu Met Asn Asn Asp
145                 150                 155                 160

Leu Ile Val Lys Ile Lys Gly Glu Phe Lys Asn Cys Asp His Ser Ile
                165                 170                 175

Tyr Leu Asn Glu Ser Lys Ile Ile Arg Pro Asn Met Lys Cys His Asn
            180                 185                 190

Gly Val Val His Ile Val Asp Lys Pro Ile Ile Phe
        195                 200
```

<210> SEQ ID NO 4
<211> LENGTH: 612
<212> TYPE: DNA
<213> ORGANISM: Plasmodium gallinaceum

<400> SEQUENCE: 4

```
atgaaaaata gtggttataa tttaattatt aaaagactat atactcgtag tggtggatta     60
cgaaaaccac aaaaagtaac taatgatcca gaaagtatta tagaaaaagt ttattggtgt    120
tttgaacata aacctattaa aaggacaatt gttaattta tattttcaca taaggaattg    180
```

```
aaattttttct ctaattttttt aaaccatcca aatgttggcg tatcattaat ccatgaatta    240
tctttagagg gaccattcac aggattttta ccatcaaatg aagcattaaa gttaattaat    300
tcagaatgtt taaataaatt atataaggat gataataaat tatctgaatt tgttttaaat    360
cattttacaa aagattttg gctatataga gatttatatg gatcatcata ccagccttgg    420
ttaatatata atgaaaaaag agaagcacca gaaaaaatca ctaacttaat gaataatgat    480
ttaatagtaa aaataaaagg ggaatttaaa aattgtgatc attcaattta tttaaacgaa    540
tcaaaaatta tcagacctaa tatgaaatgt cacaatggtg tagttcatat tgtagataag    600
ccaataatat tt                                                        612

<210> SEQ ID NO 5
<211> LENGTH: 204
<212> TYPE: PRT
<213> ORGANISM: Plasmodium reichenowi

<400> SEQUENCE: 5

Met Lys Ile Lys Phe Tyr Asn Leu Ile Ser Lys Arg Leu Tyr Thr Arg
1               5                   10                  15

Ser Gly Gly Leu Arg Lys Pro Gln Lys Val Thr Asn Asp Pro Glu Ser
            20                  25                  30

Ile Asn Arg Lys Val Tyr Trp Cys Phe Glu His Lys Pro Val Lys Arg
        35                  40                  45

Thr Ile Ile Asn Leu Ile Tyr Ser His Asn Glu Leu Lys Ile Phe Ser
    50                  55                  60

Asn Leu Leu Asn His Pro Ile Val Gly Ser Ser Leu Ile His Glu Leu
65                  70                  75                  80

Ser Leu Asp Gly Pro Tyr Thr Ala Phe Leu Pro Ser Asn Glu Ala Met
                85                  90                  95

Lys Leu Ile Asn Ile Glu Ser Phe Asn Lys Leu Tyr Asn Asp Glu Asn
            100                 105                 110

Lys Leu Ser Glu Phe Val Leu Asn His Val Thr Lys Glu Tyr Trp Leu
        115                 120                 125

Tyr Arg Asp Leu Tyr Gly Ser Ser Tyr Gln Pro Trp Leu Met Tyr Asn
    130                 135                 140

Glu Lys Arg Glu Ala Pro Glu Lys Leu Arg Asn Leu Leu Asn Asn Asp
145                 150                 155                 160

Ile Ile Val Lys Ile Glu Gly Glu Phe Lys His Cys Asn His Ser Ile
                165                 170                 175

Tyr Leu Asn Gly Ser Lys Ile Ile Arg Pro Asn Met Lys Cys His Asn
            180                 185                 190

Gly Val Val His Ile Val Asp Lys Pro Ile Ile Phe
        195                 200

<210> SEQ ID NO 6
<211> LENGTH: 612
<212> TYPE: DNA
<213> ORGANISM: Plasmodium reichenowi

<400> SEQUENCE: 6
atgaaaatta aatttataa tttgataagt aaaagattat atactcgaag tggtggttta     60
agaaagcctc aaaaggtaac aaacgaccca gaaagtataa atagaaaagt atattggtgt    120
tttgaacata agcctgtaaa aaggacaatt attaatttaa tatattcaca taacgaactc    180
aagatattct ctaatctgtt aaatcatcct atagttggta gctcgttaat acatgaatta    240
```

```
tctctcgatg gcccttatac tgcatttctt ccctccaacg aagccatgaa attaataaat    300
atagaaagtt tcaataaatt gtataacgat gaaaataaat tatcagaatt tgttttaaat    360
cacgttacga agaatattg gctgtataga gatttatatg gttcttctta ccaaccgtgg     420
ttaatgtaca atgaaaaaag ggaagctcca gaaaaattaa gaaatttatt gaataatgat    480
ataatagtaa aaattgaggg ggaatttaaa cattgcaatc attcgatata tttaaatggt    540
tcaaaaatta taagaccaaa tatgaagtgc cacaatggag ttgtgcatat agtagataag    600
cccatcattt tt                                                        612
```

<210> SEQ ID NO 7
<211> LENGTH: 206
<212> TYPE: PRT
<213> ORGANISM: Plasmodium vivax

<400> SEQUENCE: 7

```
Met Lys Lys Ser Arg Pro Pro Phe Leu Val Ile Lys Arg Leu Tyr Thr
 1               5                   10                  15

Arg Ser Gly Gly Leu Arg Lys Pro Gln Lys Val Thr Asn Asp Pro Glu
            20                  25                  30

Ser Ile Asn Arg Lys Thr Tyr Trp Cys Phe Glu His Lys Pro Ile Lys
        35                  40                  45

Arg Thr Leu Val Asn Leu Ile Tyr Ser His Asn Glu Leu Lys Leu Phe
    50                  55                  60

Ser Arg Phe Leu Asn His Pro Asn Val Gly Thr Ser Leu Val His Glu
65                  70                  75                  80

Leu Ser Leu Glu Gly Pro Tyr Thr Gly Phe Leu Pro Ser Asn Glu Ala
                85                  90                  95

Leu Lys Leu Ile Ser Pro Glu Ser Leu Ala Lys Leu Tyr Glu Glu Gly
            100                 105                 110

Asp Lys Leu Met Glu Phe Val Leu Gly His Phe Ala Lys Asp Phe Trp
        115                 120                 125

Leu Tyr Arg Asp Leu Tyr Gly Ser Ser Tyr Gln Pro Trp Leu Val Phe
    130                 135                 140

Asn Glu Arg Arg Asp Ala Pro Glu Lys Ile Thr Asn Leu Val Asn Arg
145                 150                 155                 160

Asp Leu Leu Val Glu Ile Thr Gly Glu Phe Lys Asn Cys Asp His Ser
                165                 170                 175

Ile Ser Leu Asn Gly Ala Lys Ile Ile Arg Pro Asn Met Lys Cys His
            180                 185                 190

Asn Gly Val Val His Ile Val Asp Arg Pro Ile Ile Gln Arg
        195                 200                 205
```

<210> SEQ ID NO 8
<211> LENGTH: 618
<212> TYPE: DNA
<213> ORGANISM: Plasmodium vivax

<400> SEQUENCE: 8

```
atgaaaaaga gccgcccacc cttccttgtc attaaaaggc tatacacacg cagtggcgga    60
ttgaggaaac cgcaaaaagt gacgaacgat cccgaaagca ttaatcgaaa acgtactgg    120 tgctttgaac acaaacctat taagaggacg ttggtcaatt tgatatactc tcataatgaa   180
ttgaaattat tctcccgttt tcttaatcac cccaatgtgg gtacctccct tgtacacgag   240
ctttccttgg aaggccccta cacggggttc ctgccttcga acgaggctct gaaattgatt   300
```

-continued

```
agccccgaga gtttagccaa attgtatgaa gaaggagaca agttgatgga attcgttttg    360
ggccacttcg cgaaggactt ctggctctac agggacctgt acgggtcgtc ctaccagccc    420
tggctcgtgt tcaacgagag gagggacgcc cctgagaaaa tcaccaactt agttaacaga    480
gacctacttg tagagataac aggagagttt aaaaattgcg accactcgat ttccctgaat    540
ggagcgaaga tcatcagacc gaacatgaag tgccacaacg gagtggtgca cattgtagac    600
aggccgataa tacagagg                                                   618
```

```
<210> SEQ ID NO 9
<211> LENGTH: 204
<212> TYPE: PRT
<213> ORGANISM: Plasmodium yoelii
<400> SEQUENCE: 9

Met Lys Lys Lys Leu Tyr Asn Leu Val Leu Lys Arg Ser Tyr Thr Arg
1               5                   10                  15

Ser Gly Gly Leu Arg Lys Pro Gln Lys Val Thr Asn Asp Pro Glu Ser
            20                  25                  30

Ile Asn Arg Lys Val Tyr Trp Cys Phe Glu His Lys Pro Val Arg Arg
        35                  40                  45

Thr Val Ile Asn Leu Ile Phe Ser His Asn Glu Leu Lys Asn Phe Ser
    50                  55                  60

Thr Leu Leu Arg Asn Thr Asn Ala Ser Ser Ser Leu Ile His Glu Leu
65                  70                  75                  80

Ser Leu Glu Gly Pro Tyr Thr Gly Phe Leu Pro Ser Asp Glu Ala Leu
                85                  90                  95

Asn Leu Leu Ser Thr Asn Ser Leu Asn Lys Leu Tyr Lys Asp Asp Asn
            100                 105                 110

Lys Met Ser Glu Phe Val Leu Asn His Phe Thr Lys Gly Leu Trp Met
        115                 120                 125

Tyr Arg Asp Leu Tyr Gly Ser Ser Tyr Gln Pro Trp Leu Met Tyr Asn
    130                 135                 140

Glu Lys Arg Glu Ala Pro Glu Lys Ile Gln Thr Leu Val Asn Asn Asp
145                 150                 155                 160

Ile Ile Val Lys Ile Glu Gly Glu Phe Lys Asn Cys Asp His Ser Ile
                165                 170                 175

Tyr Leu Asn Glu Ala Lys Ile Ile Arg Pro Asn Met Lys Cys His Asn
            180                 185                 190

Gly Ile Ile His Ile Ile Asp Lys Pro Ile Ile Phe
        195                 200
```

```
<210> SEQ ID NO 10
<211> LENGTH: 612
<212> TYPE: DNA
<213> ORGANISM: Plasmodium yoelii
<400> SEQUENCE: 10
atgaaaaaaa aattgtataa tttagttctt aaaagaagtt acacacgtag tggcggttta     60
agaaaaccac aaaaagtaac aaatgatcca gaaagtatta atagaaaggt ttattggtgt    120
tttgaacata aacctgttag gaggactgta attaatttaa tattttccca taatgaatta    180
aaaaactttt caactctttt aagaaataca aatgctagct catcgctaat tcacgagctg    240
tcattggaag ggccttatac gggatttctt ccatcagacg aagccttaaa tttattgagt    300
acaaatagtt taaataaatt atataaagat gataataaaa tgtctgagtt tgttttaaat    360
```

-continued

```
cattttacta aaggtctgtg gatgtataga gatttatatg gctcatccta tcagccatgg    420
ctaatgtata atgaaaaaag agaggcccca gaaaaaatac aaactttagt aaataacgac    480
ataattgtaa aaatagaagg ggaatttaaa aattgtgatc attctatata tttaaatgaa    540
gcaaaaatta taagacccaa tatgaaatgt cataatggca taattcatat catagataag    600
ccaataattt tt                                                        612
```

<210> SEQ ID NO 11
<211> LENGTH: 206
<212> TYPE: PRT
<213> ORGANISM: Plasmodium knowlesi

<400> SEQUENCE: 11

```
Met Lys Lys Ser His Pro Pro Phe Leu Ile Ile Lys Arg Leu Tyr Thr
1               5                   10                  15

Arg Ser Gly Gly Leu Arg Lys Pro Gln Lys Val Thr Asn Asp Pro Glu
            20                  25                  30

Ser Ile Asn Arg Lys Thr Tyr Trp Cys Phe Glu His Lys Pro Ile Lys
        35                  40                  45

Arg Thr Met Val Asn Leu Ile Tyr Ser His Asn Glu Leu Lys Leu Phe
    50                  55                  60

Ser Arg Phe Leu Ser His Pro Asn Val Gly Thr Ser Leu Ile His Glu
65                  70                  75                  80

Leu Ser Leu Glu Gly Pro Tyr Thr Gly Phe Leu Pro Ser Asn Glu Ala
                85                  90                  95

Leu Lys Leu Ile Ser Pro Glu Ser Leu Ala Lys Leu Tyr Glu Gln Arg
            100                 105                 110

Asp Lys Leu Met Glu Phe Val Leu Gly His Phe Thr Lys Asp Phe Trp
        115                 120                 125

Leu Tyr Arg Asp Leu Tyr Arg Ser Ser Tyr His Pro Trp Leu Val Phe
    130                 135                 140

Asn Glu Lys Arg Glu Ala Pro Glu Lys Ile Thr Asn Leu Val Asn Lys
145                 150                 155                 160

Asp Leu Leu Val Lys Ile Thr Gly Glu Phe Lys Asn Cys Asp His Ser
                165                 170                 175

Ile Phe Leu Asn Gly Ala Lys Ile Ile Thr Pro Asn Met Lys Cys His
            180                 185                 190

Asn Gly Val Val His Ile Val Asp Arg Pro Ile Ile Gln Arg
        195                 200                 205
```

<210> SEQ ID NO 12
<211> LENGTH: 618
<212> TYPE: DNA
<213> ORGANISM: Plasmodium knowlesi

<400> SEQUENCE: 12

```
atgaaaaaga gccaccccc cttccttatc attaaaaggt tatacacacg cagtggagga    60
ttgaggaaac cacaaaaagt gacgaacgat cccgaaagca ttaacagaaa aacatactgg    120
tgcttcgaac acaaacctat taaaggacg atggtcaatt tgatatactc ccacaatgaa    180
ctgaaattat tttcccgctt tctgagtcat cccaatgtcg gtacctccct catacacgag    240
ctatccttgg aaggccccta tacrgggttc ctgccttcga acgaagctct gaaattaatt    300
agccccgaaa gcttagccaa attatatgaa caaagagata aattgatgga atttgttttg    360
gggcacttta cgaaagactt ctggctctac agagatctct acagatcttc ctaccatccc    420
```

```
tggctcgtat ttaacgagaa aagggaagcc cctgagaaaa tcaccaactt agttaacaaa    480
gacctacttg taaaaataac aggagagttt aaaaattgcg atcactccat tttccttaat    540
ggagcgaaga tcatcacacc aaatatgaag tgccacaacg gagtggtcca tattgtagac    600
aggccgatta tacagagg                                                  618
```

<210> SEQ ID NO 13
<211> LENGTH: 204
<212> TYPE: PRT
<213> ORGANISM: Plasmodium chabaudi

<400> SEQUENCE: 13

```
Met Lys Lys Lys Leu Tyr Asn Leu Val Leu Lys Arg Asn Tyr Thr Arg
1               5                   10                  15

Cys Gly Gly Leu Arg Arg Pro Gln Lys Val Thr Asn Asp Pro Glu Ser
            20                  25                  30

Ile Asn Arg Lys Val Tyr Trp Cys Phe Glu His Lys Pro Val Arg Arg
        35                  40                  45

Thr Val Ile Asn Leu Ile Phe Ser His Asn Glu Leu Lys Asn Phe Ser
    50                  55                  60

Thr Leu Leu Arg Asn Thr Asn Ala Ser Ser Leu Ile His Glu Leu
65                  70                  75                  80

Ser Leu Glu Gly Pro Tyr Thr Gly Phe Leu Pro Ser Asp Glu Ala Leu
                85                  90                  95

Asn Leu Leu Ser Ala Asn Ser Leu Asn Lys Leu Tyr Asn Asp Asp Asn
            100                 105                 110

Lys Met Ser Glu Phe Val Leu Asn His Phe Thr Lys Gly Leu Trp Met
        115                 120                 125

Tyr Arg Asp Leu Tyr Gly Ser Ser Tyr Gln Pro Trp Leu Met Tyr Asn
    130                 135                 140

Glu Lys Arg Asp Ala Pro Glu Lys Leu Thr Thr Leu Ile Asn Asn Asp
145                 150                 155                 160

Ile Ile Val Lys Ile Glu Gly Glu Phe Lys Asn Cys Asp His Ser Ile
                165                 170                 175

Tyr Leu Asn Glu Ala Lys Ile Ile Arg Pro Asn Met Lys Cys His Asn
            180                 185                 190

Gly Ile Ile His Ile Ile Asp Lys Pro Ile Ile Phe
        195                 200
```

<210> SEQ ID NO 14
<211> LENGTH: 612
<212> TYPE: DNA
<213> ORGANISM: Plasmodium chabaudi

<400> SEQUENCE: 14

```
atgaaaaaaa aattgtataa tttagttctt aaaagaaatt acacacgctg tggcggttta     60
agaagaccac aaaaagtaac aaatgatcca gagagtatta tagaaaggt ttattggtgt    120 tttgaacata aacctgttag gaggactgta attaatttaa tattttccca taatgaatta    180
aaaaactttt caactctttt aaggaataca aatgctagct catcgctaat tcacgaactg    240
tcattggaag gacctatac gggatttctt ccttcagacg aggccttaaa tttattgagt    300
gcaaatagct aaataaatt atataatgat gataataaaa tgtctgaatt cgttttaaat    360
cattttacta aaggtctgtg gatgtacaga gatttatatg gctcatccta tcagccatgg    420
ctcatgtaca atgaaaaaag agacgcccca gaaaaattaa caactttaat aaacaacgac    480
```

```
ataattgtaa aaatagaagg agaatttaaa aattgtgatc attccatata tttaaatgaa      540
gcaaaaatta taaggcccaa tatgaaatgc cacaatggca taattcatat catagataag      600
ccaatcattt tt                                                          612
```

```
<210> SEQ ID NO 15
<211> LENGTH: 204
<212> TYPE: PRT
<213> ORGANISM: Plasmodium berghei

<400> SEQUENCE: 15
```

```
Met Lys Lys Leu Tyr Asn Leu Val Leu Lys Arg Asn Tyr Thr Arg
1               5                   10                  15

Ser Gly Gly Leu Arg Lys Pro Gln Lys Val Thr Asn Asp Pro Glu Ser
            20                  25                  30

Ile Asn Arg Lys Val Tyr Trp Cys Phe Glu His Lys Pro Val Arg Arg
        35                  40                  45

Thr Val Ile Asn Leu Ile Phe Ser His Asn Glu Leu Lys Asn Phe Ser
    50                  55                  60

Thr Leu Leu Lys Asn Thr Asn Ala Ser Ser Leu Ile His Glu Leu
65                  70                  75                  80

Ser Leu Glu Gly Pro Tyr Thr Gly Phe Leu Pro Ser Asp Glu Ala Leu
                85                  90                  95

Asn Leu Leu Ser Thr Asn Ser Leu Asn Lys Leu Tyr Lys Asp Asp Asn
            100                 105                 110

Lys Met Ser Glu Phe Val Leu Asn His Phe Thr Lys Gly Leu Trp Met
        115                 120                 125

Tyr Arg Asp Leu Tyr Gly Ser Ser Tyr Gln Pro Trp Leu Met Tyr Asn
    130                 135                 140

Glu Lys Arg Glu Ala Pro Glu Lys Ile Pro Thr Leu Val Asn Asn Asp
145                 150                 155                 160

Ile Ile Val Lys Ile Glu Gly Glu Phe Lys Asn Cys Asp His Ser Ile
                165                 170                 175

Tyr Leu Asn Glu Ala Lys Ile Ile Arg Pro Asn Met Lys Cys His Asn
            180                 185                 190

Gly Ile Ile His Ile Ile Asp Lys Pro Ile Ile Phe
        195                 200
```

```
<210> SEQ ID NO 16
<211> LENGTH: 612
<212> TYPE: DNA
<213> ORGANISM: Plasmodium berghei

<400> SEQUENCE: 16
atgaaaaaaa aattgtataa tttagttctt aaaagaaatt acacgcgtag tggcggttta       60
agaaaaccac aaaagtaac aaatgatcca gaaagtatta atagaaaggt ttattggtgt      120
tttgagcata aacctgttag gaggactgta attaatttaa tattttccca taatgaatta      180
aaaaactttt caactctttt aaaaaataca aatgctagct catcgctaat tcacgaacta      240
tcattggaag ggccttatac gggatttctt ccttcggatg aggccttaaa tttattgagt      300
acaaatagtt taaataaatt atataaagat gataataaaa tgtctgaatt tgttttaaat      360
cattttacta aaggtctgtg gatgtataga gatttatatg gctcatccta tcagccatgg      420
ctcatgtaca atgaaaaaag agaggcccca gaaaaaatac caactttagt aaacaacgac      480
ataattgtaa aaatagaagg ggaatttaaa aattgtgatc attctatata tttaaatgaa      540
```

```
gcaaaaatta taagacccaa tatgaaatgt cataatggca taattcatat catagataag    600
ccaataattt tt                                                        612
```

<210> SEQ ID NO 17
<211> LENGTH: 199
<212> TYPE: PRT
<213> ORGANISM: Theileria parva

<400> SEQUENCE: 17

```
Met Phe Ile Ser Gln Ala Leu Leu Trp Arg Ser Asn Phe Gly Gly Leu
1               5                   10                  15

Lys Lys Leu Arg Arg Val Thr Lys Asp Pro Asn Val Ile Asn Ser Lys
            20                  25                  30

Val Tyr Trp Cys Phe Glu His Lys Tyr Ile Arg Arg Thr Val Leu Ser
        35                  40                  45

Phe Cys Asn Asn Asn Pro Phe Thr Arg Ser Phe Ser Ser Leu Ile Asn
    50                  55                  60

Pro Glu Glu Ser Gly Tyr Arg Leu Ser His Glu Leu Ser Leu Pro
65                  70                  75                  80

Gly Pro Phe Thr Gly Phe Ile Pro Val Asn Glu Gly Leu Thr Gln Ala
                85                  90                  95

Leu Ser Lys Leu Glu Ala Ser Tyr Lys Asp Ser Val Val Asp Phe Val
            100                 105                 110

Arg Ser His Phe Thr His Asn Leu Trp Leu Tyr Arg Asp Ile Leu Gly
        115                 120                 125

Ser Pro Thr Gln Pro Trp Leu Leu Tyr Asn Lys Thr Arg Lys Phe Pro
    130                 135                 140

Glu Lys Leu Gln Thr Ile Asn Asn Lys Ser Leu Phe Phe Glu His Thr
145                 150                 155                 160

Gly Asp Leu Ser Lys Gly Asp Lys Glu Ile Phe Val Asn Gly Ser Lys
                165                 170                 175

Ile Leu Arg Trp Asn Leu Arg Cys His Asn Gly Val Ile His Leu Ile
            180                 185                 190

Asp Lys Pro Leu Phe Asp Ile
        195
```

<210> SEQ ID NO 18
<211> LENGTH: 600
<212> TYPE: DNA
<213> ORGANISM: Theileria parva

<400> SEQUENCE: 18

```
atgtttatct ctcaggccct gttgtggaga tctaattttg gaggcttgaa aaagttgaga    60
agagtaacaa aggacccgaa cgtcataaat tcaaaggttt actggtgttt tgaacataaa    120
tatattcgcc gtactgttct ttcattctgt aataacaacc cctttacgcg ttcttttca    180 agtttaataa atcctgagga ggaatctggc tataggttat ctcacgagtt atcacttcca    240
gggcctttta caggctttat tccagtaaat gagggcttaa ctcaggcttt atcaaagcta    300
gaggcttcat acaaggattc tgtcgttgat ttcgtgaggt cccatttac  acataactta    360 tggctatatc gtgacatact aggttctcca acccagccct ggttattgta caataaaact    420
cgaaaatttc cagaaaaact tcaaaccatt aataacaaat ctttgttctt cgaacacact    480
ggagacttgt caagggtga taaggaaatc tttgtaaacg gttcaaagat acttcgctgg    540
aacctgagat gtcataatgg agttattcac ctgatagata aacctctttt cgatatctaa    600
```

-continued

<210> SEQ ID NO 19
<211> LENGTH: 219
<212> TYPE: PRT
<213> ORGANISM: Theileria annulata

<400> SEQUENCE: 19

```
Met Phe Leu Thr Cys Tyr Phe His Phe Met Met Phe Thr Ser Lys Ala
1               5                   10                  15

Leu Ser Trp Arg Ser Asn Phe Gly Gly Leu Lys Lys Leu Arg Arg Arg
            20                  25                  30

Ser Lys Asp Pro Asn Val Ile Asn Ser Lys Val Tyr Trp Cys Phe Glu
        35                  40                  45

His Lys Tyr Ile Arg Arg Thr Val Leu Ser Phe Cys Asn Asn Asn Pro
    50                  55                  60

Phe Thr Arg Ser Phe Ser Lys Leu Ile Asn Pro Glu Glu Glu Ser Gly
65                  70                  75                  80

Ile Phe Tyr Phe Leu Ser His Val Leu Gly Tyr Arg Leu Ser His Glu
                85                  90                  95

Leu Ser Leu Pro Gly Pro Phe Thr Gly Phe Ile Pro Val Asn Glu Gly
            100                 105                 110

Leu Thr Gln Ala Leu Pro Lys Leu Glu Ser Ser Tyr Lys Asp Ala Val
        115                 120                 125

Val Asp Phe Val Arg Ser His Phe Thr His His Leu Trp Leu His Arg
    130                 135                 140

Asp Leu Leu Gly Ser Pro Thr Gln Pro Trp Leu Leu Tyr Asn Lys Thr
145                 150                 155                 160

Arg Lys Phe Pro Lys Lys Leu Gln Thr Leu Asn Asn Lys Ser Leu Phe
                165                 170                 175

Phe Glu His Thr Gly Asp Leu Ser Lys Gly Asp Lys Glu Ile Phe Val
            180                 185                 190

Asn Gly Ser Arg Ile Leu Arg Trp Asn Met Arg Cys His Asn Gly Val
        195                 200                 205

Ile His Leu Ile Asp Lys Pro Leu Phe Asp Ile
    210                 215
```

<210> SEQ ID NO 20
<211> LENGTH: 660
<212> TYPE: DNA
<213> ORGANISM: Theileria annulata

<400> SEQUENCE: 20

```
atgtttttaa cttgttattt tcattttatg atgtttactt ccaaggcctt gtcgtggaga     60
tctaattttg gagggttaaa gaagttaagg agaagatcaa aggatccaaa cgtcataaat    120
tcaaaggttt attggtgttt tgagcataaa tatattcgcc gtacagttct ttcattttgt    180
aataataatc catttacacg ttcattttca aagttaataa atcccgagga agaatcaggt    240
atttttattt ttttaagcca tgttttaggt tatagattat ctcacgagtt atcacttccc    300
gggcctttta cgggcttcat tccagtaaat gaaggcttaa cacaggcctt accgaagctg    360
gagtcctcat acaaggatgc ggtagttgat ttcgtaaggt ctcactttac ccatcattta    420
tggctacatc gtgatctgct aggctcacca acacagccct ggctactgta taacaaaact    480
cgcaaatttc caaaaaaact acaaaccctt aataacaaat ctttgttctt cgaacacaca    540
ggagatctgt caaagggtga taaggaaatc tttgtgaatg gatcaaggat acttcgctgg    600
aacatgagat gtcataatgg agttattcac ctgatagata aacccctctt tgatatttag    660
```

```
<210> SEQ ID NO 21
<211> LENGTH: 87
<212> TYPE: PRT
<213> ORGANISM: Artificial
<220> FEATURE:
<223> OTHER INFORMATION: consensus sequence

<400> SEQUENCE: 21

Thr Val Phe Ala Pro Thr Asp Glu Ala Phe Lys Lys Leu Pro Pro Gly
 1               5                  10                  15

Thr Leu Asn Ser Leu Leu Ala Asp Pro Lys Leu Lys Gln Leu Leu Lys
            20                  25                  30

Tyr His Ile Val Pro Gly Arg Leu Ser Ser Ala Asp Leu Leu Asn Gly
        35                  40                  45

Gly Thr Leu Pro Thr Leu Ala Gly Ser Lys Leu Arg Val Asn Val Ser
50                  55                  60

Gly Asn Ser Gly Thr Val Thr Val Asn Gly Ala Arg Ile Val Glu Ala
65                  70                  75                  80

Asp Ile Ala Ala Thr Asn Gly
                85

<210> SEQ ID NO 22
<211> LENGTH: 31
<212> TYPE: DNA
<213> ORGANISM: Artificial
<220> FEATURE:
<223> OTHER INFORMATION: synthetic oligomucleotide forward primer

<400> SEQUENCE: 22
caccatgaaa aatagatttt attataattt g                              31

<210> SEQ ID NO 23
<211> LENGTH: 27
<212> TYPE: DNA
<213> ORGANISM: Artificial
<220> FEATURE:
<223> OTHER INFORMATION: synthetic oligonucleotide reverse primer

<400> SEQUENCE: 23
aaaaatgatg ggcttatcta ctatatg                                   27

<210> SEQ ID NO 24
<211> LENGTH: 32
<212> TYPE: PRT
<213> ORGANISM: Plasmodium falciparum

<400> SEQUENCE: 24

Thr Arg Ser Gly Gly Leu Arg Lys Pro Gln Lys Val Thr Asn Asp Pro
 1               5                  10                  15

Glu Ser Ile Asn Arg Lys Val Tyr Trp Cys Phe Glu His Lys Pro Val
            20                  25                  30

<210> SEQ ID NO 25
<211> LENGTH: 87
<212> TYPE: PRT
<213> ORGANISM: Plasmodium falciparum

<400> SEQUENCE: 25

Met Lys Asn Arg Phe Tyr Tyr Asn Leu Ile Ile Lys Arg Leu Tyr Thr
 1               5                  10                  15

Arg Ser Gly Gly Leu Arg Lys Pro Gln Lys Val Thr Asn Asp Pro Glu
```

```
                    20                  25                  30

Ser Ile Asn Arg Lys Val Tyr Trp Cys Phe Glu His Lys Pro Val Lys
        35                  40                  45

Arg Thr Ile Ile Asn Leu Ile Tyr Ser His Asn Glu Leu Lys Ile Phe
    50                  55                  60

Ser Asn Leu Leu Asn His Pro Thr Val Gly Ser Ser Leu Ile His Glu
65                  70                  75                  80

Leu Ser Leu Asp Gly Pro Tyr
                85

<210> SEQ ID NO 26
<211> LENGTH: 261
<212> TYPE: DNA
<213> ORGANISM: Plasmodium falciparum

<400> SEQUENCE: 26
atgaaaaata gatttttatta aatttgata attaaaagat tatatacacg aagtggcggt     60
ttaagaaaac ctcaaaaggt aaccaacgac ccagaaagta taaatagaaa agtatattgg    120
tgttttgaac ataagcctgt aaaaaggaca attattaatt taatatattc acataacgaa    180
ctcaagatat tttctaatct gttaaatcat cctacagttg gcagctcgtt aatacatgaa    240
ttatctctcg atggccctta t                                              261

<210> SEQ ID NO 27
<211> LENGTH: 20
<212> TYPE: PRT
<213> ORGANISM: Plasmodium falciparum

<400> SEQUENCE: 27

Met Lys Asn Arg Phe Tyr Tyr Asn Leu Ile Ile Lys Arg Leu Tyr Thr
1               5                   10                  15

Arg Ser Gly Gly
            20

<210> SEQ ID NO 28
<211> LENGTH: 20
<212> TYPE: PRT
<213> ORGANISM: Plasmodium falciparum

<400> SEQUENCE: 28

Asn Leu Ile Ile Lys Arg Leu Tyr Thr Arg Ser Gly Gly Leu Arg Lys
1               5                   10                  15

Pro Gln Lys Val
            20

<210> SEQ ID NO 29
<211> LENGTH: 20
<212> TYPE: PRT
<213> ORGANISM: Plasmodium falciparum

<400> SEQUENCE: 29

Thr Arg Ser Gly Gly Leu Arg Lys Pro Gln Lys Val Thr Asn Asp Pro
1               5                   10                  15

Glu Ser Ile Asn
            20

<210> SEQ ID NO 30
<211> LENGTH: 20
<212> TYPE: PRT
<213> ORGANISM: Plasmodium falciparum
```

```
<400> SEQUENCE: 30

Gly Leu Arg Lys Pro Gln Lys Val Thr Asn Asp Pro Glu Ser Ile Asn
1               5                   10                  15

Arg Lys Val Tyr
            20

<210> SEQ ID NO 31
<211> LENGTH: 20
<212> TYPE: PRT
<213> ORGANISM: Plasmodium falciparum

<400> SEQUENCE: 31

Thr Asn Asp Pro Glu Ser Ile Asn Arg Lys Val Tyr Trp Cys Phe Glu
1               5                   10                  15

His Lys Pro Val
            20

<210> SEQ ID NO 32
<211> LENGTH: 20
<212> TYPE: PRT
<213> ORGANISM: Plasmodium falciparum

<400> SEQUENCE: 32

Val Tyr Trp Cys Phe Glu His Lys Pro Val Lys Arg Thr Ile Ile Asn
1               5                   10                  15

Leu Ile Tyr Ser
            20

<210> SEQ ID NO 33
<211> LENGTH: 20
<212> TYPE: PRT
<213> ORGANISM: Plasmodium falciparum

<400> SEQUENCE: 33

Lys Pro Val Lys Arg Thr Ile Ile Asn Leu Ile Tyr Ser His Asn Glu
1               5                   10                  15

Leu Lys Ile Phe
            20

<210> SEQ ID NO 34
<211> LENGTH: 20
<212> TYPE: PRT
<213> ORGANISM: Plasmodium falciparum

<400> SEQUENCE: 34

Asn Leu Ile Tyr Ser His Asn Glu Leu Lys Ile Phe Ser Asn Leu Leu
1               5                   10                  15

Asn His Pro Thr
            20

<210> SEQ ID NO 35
<211> LENGTH: 20
```

```
<212> TYPE: PRT
<213> ORGANISM: Plasmodium falciparum

<400> SEQUENCE: 35

Asn Glu Leu Lys Ile Phe Ser Asn Leu Leu Asn His Pro Thr Val Gly
1               5                   10                  15

Ser Ser Leu Ile
            20

<210> SEQ ID NO 36
<211> LENGTH: 20
<212> TYPE: PRT
<213> ORGANISM: Plasmodium falciparum

<400> SEQUENCE: 36

Asn Leu Leu Asn His Pro Thr Val Gly Ser Ser Leu Ile His Glu Leu
1               5                   10                  15

Ser Leu Asp Gly
            20

<210> SEQ ID NO 37
<211> LENGTH: 8
<212> TYPE: PRT
<213> ORGANISM: Plasmodium falciparum

<400> SEQUENCE: 37

Thr Asn Asp Pro Glu Ser Ile Asn
1               5

<210> SEQ ID NO 38
<211> LENGTH: 24
<212> TYPE: DNA
<213> ORGANISM: Plasmodium falciparum

<400> SEQUENCE: 38
accaacgacc cagaaagtat aaat                                          24

<210> SEQ ID NO 39
<211> LENGTH: 96
<212> TYPE: DNA
<213> ORGANISM: Plasmodium falciparum

<400> SEQUENCE: 39
acacgaagtg gcggtttaag aaaacctcaa aaggtaacca acgacccaga agtataaat    60 agaaaagtat attggtgttt tgaacataag cctgta                             96
```

THERAPEUTIC TARGET FOR PROTOZOAL DISEASES

STATEMENT OF FEDERALLY SPONSORED RESEARCH AND DEVELOPMENT

This invention was made, in part, with government support under Grant No. DE-FC36-01GO11086 awarded by the Department of Energy, and No. DAAD19-02-1-0278 awarded by Defense Advanced Research Projects Agency. The government has certain rights in the invention.

BACKGROUND OF THE INVENTION

1. Field of the Invention

The invention generally relates to therapies for the treatment and prevention of certain parasitic diseases. In particular, the invention provides a novel Fasciclin Related Adhesive Protein (FRAP) as a target for therapeutic intervention in diseases caused by *Plasmodium* species.

2. Background of the Invention

Malaria, a blood-borne infection caused by *Plasmodium* parasites, is a major health issue in the tropics, with 300-500 million clinical episodes of this disease occurring each year. A licensed vaccine against malaria is not available and the parasite is developing resistance against most of the currently available antimalarials. There is an urgent need to develop new therapeutics (drugs and vaccines) against malaria, which will reduce the morbidity and mortality associated with this disease. The genome of *Plasmodium falciparum* has been sequenced and can be exploited to understand the molecular basis of the onset and sustenance of infection by these pathogens. Deciphering these mechanisms will unravel the complex interplay between the troika of host, pathogen and its environment, which is vital for identifying new targets for intervention.

Malaria infection starts with the introduction of *Plasmodium* sporozoites into the blood stream of its human host, when it is bitten by an infected mosquito. Of the four *Plasmodium* species that infect humans, *P. falciparum* is the most virulent—resulting in severe anemia and cerebral malaria, which can be fatal. Fewer than 200 sporozoites are introduced and even fewer succeed in invading liver cells, the target organ for the onset of malaria infection in a host. A successful adhesion and liver cell invasion by the sporozoite is critical for this onset and is therefore, the Achilles heel of the parasite. Once inside the liver cell, the parasite rapidly multiplies and within a few days releases thousands of parasites, which leads to the clinical pathology of this disease. Therefore, an ideal approach to control malaria is to develop a vaccine or therapeutic, which either prevents the sporozoite from infecting liver cells or destroys the parasite during liver stages of its life cycle. Such a vaccine is feasible as animals and human volunteers immunized with *Plasmodium* sporozoites that have been attenuated by exposure to X-Ray or gamma radiation, are protected when subsequently challenged with infectious sporozoites (Hoffman, et al. (2002) *J Infect Dis,*, 1155-1164; Nussenzweig et al. (1967) Protective immunity produced by the injection of x-irradiated sporozoites of *Plasmodium berghei. Nature,* 216, 160-162.). While this groundbreaking discovery clearly indicated that it is feasible to make a vaccine against malaria, the biggest stumbling block for malaria researchers worldwide has been to decipher the parasite antigens recognized by the host and to understand the immune mechanisms underlying this protection. Extensive immunological studies with known sporozoite antigens have concluded that this protection is not conferred due to a dominant immune response against a single antigen but is mediated by the summation of many modest humoral and cell-mediated immune responses against a large variety of antigens, many of which are currently not known (Hoffmnan, S. (1996) *Malaria Vaccine Development: A multi immune response approach*. ASM press, Washington, D.C.). Identification of these antigens is not only the major challenge, it is vital for the development of a successful vaccine against malaria.

Historically, antigen(s) selected as a vaccine candidate in a given pathosystem are (i) present on the surface of the pathogen, (ii) are generally involved in host-pathogen interactions and are therefore, one of the first molecules that are recognized by the host immune system (Moxon, R. and Rappuoli, R. (2002) *Br Med Bull,* 62, 45-58). These criteria are also valid for malaria parasite as the two major vaccine candidates viz., Circumsporozoite protein (CSP) (Cerami, C. et al. (1992) *Cell,* 70, 1021-1033) and Thrombospondin-related anonymous protein (TRAP) (Robson, et al. (1995) *Embo J,* 14, 3883-3894) are involved in the invasion of liver cells by the parasite.

Upon entering red blood cells, the *Plasmodium* parasite undergoes rapid multiplication giving rise to 28-32 parasites in less than 48 hours. Hemoglobin represents ~95% of the total RBC content, and the parasite digests up to 75% of the hemoglobin, which serves as its source of amino acids. While this process of hemoglobin digestion provides the parasite with a ready source of amino acids, it also releases free heme, which in the absence of a globin moiety, is extremely toxic for the parasite (Gluzman, et al. (1994) *J Clin Invest,* 93, 1602-1608.). The parasite survives by effectively neutralizing toxic heme into a non-toxic and polymerized product known as hemozoin, which is chemically identical to β-hematin (Francis,et al. (1997) *Annu Rev Microbiol,* 51, 97-123. Most of the currently available antimalarials have been shown to be binding to free heme, which inhibits its polymerization, and the toxicity resulting from the free heme causes the death of the parasite (Slater and Cerami (1992) *Nature,* 355, 167-169).

Therefore, pathway(s) that lead to hemozoin formation are extremely attractive drug targets.

Unfortunately, the mechanism(s) in use by the parasite for the polymerization process is poorly understood. Two parasite proteins viz., Histidine rich protein II and III have been proposed to be responsible for this activity (Sullivan, et al. (1996) *Science,* 271, 219-222.), though parasites lacking either or both of the proteins make copious amounts of hemozoin without any loss of activity (Wellems, et al. (1991) *Proc Natl Acad Sci USA,* 88, 3382-3386). Therefore, an unknown protein(s) has been long thought to be responsible for this activity.

The prior art has thus far failed to provide satisfactory vaccines or drug therapies to combat diseases caused by parasites such as *Plasmodium*. There is thus an ongoing need to identify and characterize potential targets for such therapeutic intervention.

SUMMARY OF THE INVENTION

The parasite protein "Fasciclin Related Adhesive Protein" ("FRAP") has been discovered, and its use as a target for therapeutic intervention in parasitic diseases is described herein. FRAP is expressed during the infective forms of parasites such as *Plasmodium* and *Theileria*, is intimately involved in the onset of parasitic infections, and key sequences of the protein are highly conserved across *Plasmodium* species and related genera. Thus, this protein is an ideal target for the treatment and/or prevention of parasitic diseases by a variety of methods, including vaccine development. In addition, FRAP catalyzes the neutralization of toxic heme into non-toxic hemozoin. Thus, FRAP is an attractive target for inhibitory drug therapies.

The present invention provides a composition for eliciting an immune response to *Plasmodium*. The composition comprises a substantially purified synthesized or recombinant protein comprising an amino acid sequence represented by SEQ ID NO: 1 or SEQ ID NO: 25; or a substantially purified synthesized or recombinant protein comprising an amino acid sequence that displays at least 90% identity to SEQ ID NO: 1 or SEQ ID NO: 25. The composition may further include at least one of: one or more additional antigens, and one or more adjuvants. The composition may further include one or more additional peptides, polypeptides or proteins each of which is different from said substantially purified synthesized or recombinant protein.

The invention also provides a composition for eliciting an immune response to *Plasmodium*, which comprises a substantially purified synthesized or recombinant peptide, polypeptide or protein comprising an amino acid sequence represented by SEQ ID NO: 37. The substantially purified synthesized or recombinant peptide, polypeptide or protein may comprise an amino acid sequence represented by SEQ ID NO: 24, or an amino acid sequence that displays at least about 85% identity to SEQ ID NO: 24. The composition may further include at least one of: one or more additional antigens, and one or more adjuvants. The composition may further include one or more additional peptides, polypeptides or proteins each of which is different from the substantially purified synthesized or recombinant peptide, polypeptide or protein.

In addition, the invention provides a vaccine comprising a substantially purified synthesized or recombinant protein comprising an amino acid sequence represented by SEQ ID NO: 1 or SEQ ID NO: 25; or a substantially purified synthesized or recombinant protein comprising an amino acid sequence that displays at least 90% identity to SEQ ID NO: 1 or SEQ ID NO: 25. The vaccine may further include at least one of one or more additional antigens, and one or more adjuvants.

In another embodiment, the invention provides a vaccine comprising a substantially purified synthesized or recombinant peptide, polypeptide or protein comprising an amino acid sequence represented by SEQ ID NO: 37. The substantially purified synthesized or recombinant peptide, polypeptide or protein may comprise an amino acid sequence represented by SEQ ID NO: 24, or an amino acid sequence that is at least 85% identical to SEQ ID NO: 24. The vaccine may include at least one of: one or more additional antigens, and one or more adjuvants. The vaccine may further include one or more additional peptides, polypeptides or proteins each of which is different from the substantially purified synthesized or recombinant peptide, polypeptide or protein.

In another embodiment, the invention provides a substantially purified synthesized or recombinantly produced antibody specific for: a protein with an amino acid sequence represented by SEQ ID NO: 1 or SEQ ID NO: 25; or a protein with an amino acid sequence that displays at least 90% identity to SEQ ID NO: 1 or SEQ ID NO: 25. In some embodiments, the antibody is chimeric, humanized, or fully human.

In another embodiment, the invention provides a substantially purified synthesized or recombinantly produced antibody specific for: a peptide with an amino acid sequence represented by SEQ ID NO: 37, or a peptide with an amino acid sequence represented by SEQ ID NO: 24. In some embodiments, the antibody is chimeric, humanized, or fully human.

The invention further provides a transfected cell comprising expressable recombinant DNA that encodes: one or more of a peptide, polypeptide or protein which is or includes an amino acid sequence represented by SEQ ID NO: 1, SEQ ID NO: 24, SEQ ID NO: 25, or SEQ ID NO: 37; or one or more of a peptide, polypeptide or protein which is or includes an amino acid sequences that displays at least 90% identity with one or more of SEQ ID NO: 1, SEQ ID NO: 25, or SEQ ID NO: 37, or at least about 85% identity with SEQ ID NO: 24. In another embodiment, such transfected cells are used to elicit an immune response and/or to serve as a vaccine.

In yet another embodiment, the invention provides a method of treating or preventing a disease caused by a *Plasmodium* parasite in a patient in need thereof. The method comprises the step of administering to the patient one or more antibodies specific for one or more amino acid sequences represented by SEQ ID NO: 1, SEQ ID NO: 24, SEQ ID NO: 25 or SEQ ID NO: 37. The antibody may be synthesized or recombinantly produced.

In yet another embodiment, the invention provides a method of eliciting an immune response to a *Plasmodium* parasite in a patient in need thereof. The method comprises the step of administering to the patient one or more peptides, polypeptides or proteins which comprise one or more amino acid sequences selected from the group consisting of SEQ ID NO: 1, SEQ ID NO: 24, SEQ ID NO: 25, SEQ ID NO: 37, and amino acid sequences which display at least 90% identity with SEQ ID NO: 1, SEQ ID NO: 25, SEQ BD NO: 37, or at least about 85% identity with SEQ ID NO: 24. The peptides, polypeptides or proteins may be synthesized or recombinantly produced.

In yet another embodiment, the invention provides a method of treating or preventing a disease caused by a *Plasmodium* or *Theileria* parasite in a patient in need thereof. The method comprises the step of administering to the patient a compound that inhibits FRAP protein. In one embodiment, the patient is an animal. In one embodiment, the compound is an antibody. In some instances, the compound interacts with a peptide, polypeptide protein that comprises an amino acid sequence selected from the group consisting of SEQ ID NO: 1, SEQ ID NO: 7, SEQ ID NO: 17, SEQ ID NO: 19, SEQ ID NO: 24, SEQ ID NO: 25 and SEQ ID NO: 37. In addition, the compound may bind to or interact with one or more of amino acid residues F42, H44 and H122 of FRAP protein encoded by SEQ ID NOS:1, 7 and 11, or with one or more equivalent amino acid residues in other FRAP proteins, i.e. amino acid residues that fulfill the same or a similar function in another FRAP protein, such as the proteins encoded by SEQ ID NO: 3, SEQ ID NO: 5, or SEQ ID NO: 9, SEQ ID NO: 13, SEQ ID NO: 15, SEQ ID NO: 17 and SEQ ID NO: 19.

In yet another embodiment, the invention provides a whole organism vaccine against a parasite. The vaccine comprises an attenuated parasite which is unable to produce a fully functional FRAP protein. The attenuated parasite may include one or more mutations or deletions in a coding region that encodes the fully functional FRAP protein. One or more mutations may be in a coding region that encodes the fully functional FRAP protein at a site which encodes for an amino acid residue selected from the group consisting of phenylalanine 42, histidine 44, phenylalanine 64, histidine 79, phenylalanine 90, histidine 122, cysteine 191, histidine 192 and histidine 197 of FRAP proteins encoded by SEQ ID NOS: 1, 7 and 11, or the equivalent amino acid residues in other FRAP proteins, i.e. amino acid residues that fulfill the same or a similar function in another FRAP protein, such as the proteins encoded by SEQ ID NO: 3, SEQ ID NO: 5, or SEQ ID NO: 9, SEQ ID NO: 13, SEQ ID NO: 15, SEQ ID NO: 17 and SEQ ID NO: 19. In one embodiment, the parasite is unable to produce a fully functional FRAP protein due to RNA silencing. In another embodiment, the parasite is unable to produce normal levels of a fully functional FRAP protein due to attenuation of a promoter that is operably linked to DNA encoding FRAP.

The invention also provides a method for high throughput screening for antimalarial agents that inhibit the conversion of heme to hemozoin. The method comprises the steps of: providing a potential antimalarial agent; determining a first level of conversion of heme substrate to hemozoin by FRAP in the presence of said potential antimalarial agent, and a second level of conversion of heme substrate to hemozoin by FRAP in the absence of said potential antimalarial agent; and comparing said first level of conversion to said second level of conversion, wherein if said second level of said conversion is higher than said first level of conversion, said potential antimalarial agent inhibits the conversion of heme to hemozoin. In some embodiments, FRAP has one or more amino acid sequences selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and SEQ ID NO: 19.

The invention also provides a method for expression and purification of a recombinant protein. The method comprises the step of providing a vector that operably encodes the recombinant protein, wherein said recombinant protein comprises one or more of SEQ ID NO: 1 or SEQ ID NO: 25. The recombinant protein may be a fusion protein, and may comprise one or more copies of SEQ ID NO: 24 or SEQ ID NO: 37. The vector may also encode an antigen such as CSP or TRAP.

The invention also provides a method for diagnosing prior exposure to *Plasmodium* or *Theileria*. The method comprises the steps of: obtaining a biological sample from a patient and determining whether at least one of an amino acid sequence selected from the group consisting of SEQ ID NO: 1, SEQ ID NO: 7, SEQ ID NO: 17, SEQ ID NO: 19, SEQ ID NO: 24, SEQ ID NO: 25 and SEQ ID NO: 37, or an antibody to at least one of SEQ ID NO: 1, SEQ ID NO: 7, SEQ ID NO: 17, SEQ ID NO: 19, SEQ ID NO: 24, SEQ ID NO: 25 and SEQ ID NO: 37 is present in said biological sample.

The invention also provides a diagnostic assay for determining exposure to *Plasmodium* or *Theileria*, comprising: one or more substances capable of selectively binding i) at least one amino acid sequence selected from the group consisting of SEQ ID NO: 1, SEQ ID NO: 7, SEQ ID NO: 17, SEQ ID NO: 19, SEQ ID NO: 24, SEQ ID NO: 25 and SEQ ID NO: 37; or ii) an antibody to at least one of SEQ ID NO: 1, SEQ ID NO: 7, SEQ ID NO: 17, SEQ ID NO: 19, SEQ ID NO: 24, SEQ ID NO: 25 and SEQ ID NO: 37; and one or more labels which are activated upon binding by said one or more substances.

The invention also provides a method for identifying compounds that inhibit heme neutralization by FRAP. The method comprises the steps of a) contacting FRAP, or an extract containing FRAP, with a known amount of heme, in the presence or absence of a known dilution of a test compound; and b) quantitating a percent inhibition of said heme neutralization by said test compound by comparing differences in said heme neutralization in the presence and absence of said test compound. FRAP may have one or more amino acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and SEQ ID NO: 19.

The invention also provides a method for diagnosing exposure (prior or ongoing) to *Plasmodium* or *Theileria*. The method comprises the steps of: obtaining a biological sample from a patient and determining whether at least one of a nucleic acid sequence selected from the group consisting of SEQ ID NO: 2, SEQ ID NO: 8, SEQ ID NO: 18, SEQ ID NO: 20, SEQ ID NO: 25, SEQ ID NO: 26 and SEQ ID NO: 38, is present in said biological sample. The step of determining may be performed using polymerase chain reaction.

The invention also provides a diagnostic kit or assay for determining exposure (prior or ongoing) to *Plasmodium* or *Theileria*. The kit or assay comprises: one or more nucleic acids which hybridize to one or more nucleic acid sequence selected from the group consisting of SEQ ID NO: 2, SEQ ID NO: 8, SEQ ID NO: 18, SEQ ID NO: 20, SEQ ID NO: 26, SEQ ID NO: 38 and SEQ ID NO: 39; and a mechanism for detecting hybridization. The kit may further comprise means for quantifying an amount of hybridization, and the one or more nucleic acids may be bound to a substrate, such as a biochip.

The invention further provides a composition for eliciting an immune response to *Plasmodium*. The composition comprises a nucleic acid sequence encoding an amino acid sequence represented by SEQ ID NO: 1. SEQ ID NO: 7 or SEQ ID NO: 25. The nucleic acid sequence may be SEQ ID NO: 2, SEQ ID NO: 8, or SEQ ID NO: 26 or a sequence that displays at least 90% homology to SEQ ID NO: 2, SEQ ID NO: 8, or SEQ ID NO: 26. The composition may contain one or more adjuvants. The composition may contain a nucleic acid encoding one or more peptides, polypeptides or proteins which are not encoded by SEQ ID NO: 2, SEQ ID NO: 8, or SEQ ID NO: 26. In one embodiment, the nucleic acid sequence is contained in a vector, for example, an adenoviral vector.

The invention also provides a composition for eliciting an immune response to *Plasmodium* which comprises a nucleic acid sequence encoding the amino acid sequence represented by SEQ ID NO: 37. In one embodiment, the nucleic acid sequence comprises a nucleic acid sequence encoding an amino acid sequence represented by SEQ ID NO: 24. The nucleic acid sequence may be SEQ ID NO: 38 or SEQ ID NO: 39, or a sequence that displays at least 90% homology to SEQ ID NO: 38, or a sequence that displays at least 85% homology to SEQ ID NO: 39. The composition may contain one or more adjuvants, and may further comprise nucleic acids encoding one or more peptides, polypeptides or proteins which are not encoded by SEQ ID NO: 38 or SEQ ID NO: 39. In one embodiment, the nucleic acid sequence is contained in a vector, for example, an adenoviral vector.

The invention also provides a vaccine for eliciting an immune response to *Plasmodium*, the vaccine comprising a nucleic acid sequence encoding an amino acid sequence represented by SEQ ID NO: 1, SEQ ID NO: 7 or SEQ ID NO: 25. In some embodiments, the nucleic acid sequence is SEQ ID NO: 2, SEQ ID NO: 8, or SEQ ID NO: 26, or a sequence that displays at least 90% homology to SEQ ID NO: 2, SEQ ID NO: 8, or SEQ ID NO: 26. The composition may contain one or more adjuvants, and may comprise a nucleic acid encoding one or more peptides, polypeptides or proteins which are not encoded by SEQ ID NO: 2, SEQ ID NO: 8, or SEQ ID NO: 26. In one embodiment, the nucleic acid sequence is contained in a vector, for example, an adenoviral vector.

The invention further provides a vaccine for eliciting an immune response to *Plasmodium*, the vaccine comprising a nucleic acid sequence encoding an amino acid sequence represented by SEQ ID NO: 37. In one embodiment, the nucleic acid sequence comprises a nucleic acid sequence encoding an amino acid sequence represented by SEQ ID NO: 24. The nucleic acid sequence may be SEQ ID NO: 38 or SEQ ID NO: 39, or a sequence that displays at least 90% homology to SEQ ID NO: 38, or a sequence that displays at least 85% homology to SEQ ID NO: 39. The composition may contain one or more adjuvants, and may comprise nucleic acids encoding one or more peptides, polypeptides or proteins which are not encoded by SEQ ID NO: 38 or SEQ ID NO: 39.ln one embodiment, the nucleic acid sequence is contained in a vector, for example, an adenoviral vector.

The invention further provides a vaccine for eliciting an immune response to *Theileria*, the vaccine comprising a nucleic acid sequence encoding an amino acid sequence represented by SEQ ID NO: 17 or SEQ ID NO: 19. In some embodiments, the nucleic acid sequence is SEQ ID NO: 18 or SEQ ID NO: 20, or a sequence that displays at least 90% homology to SEQ ID NO: 18or SEQ ID NO: 20.

BRIEF DESCRIPTION OF THE DRAWINGS

FIG. 1A-J. This figure shows the amino acid sequences of the FRAP protein in a variety of organisms as follows: A, *Plasmodium falciparum*; B, *Plasmodium vivax*; C, *Plasmodium gallinaceum*; D, *Plasmodium knowlesi*; E, *Plasmodium reichenowi*; F, *Plasmodium yoelii*; G, *Plasmodium berghei*; H, *Plasmodium chaubaudi*; I, *Theileria parva*, and J, *Theileria annulata*.

FIG. 2A-J. This figure shows the nucleic acid sequences that encode the FRAP protein in a variety of organisms as follows: A, *Plasmodium falciparum*; B, *Plasmodium vivax*; C, *Plasmodium gallinaceum*; D, *Plasmodium knowlesi*; E, *Plasmodium reichenowi*; F, *Plasmodium yoelii*; G, *Plasmodium berghei*; H, *Plasmodium chaubaudi*; I, *Theileria parva*, and J, *Theileria annulata*. The sequences represent the coding sequence of FRAP from different parasites. The gene itself is present on three separate exons and the sequence provided below is intron-free and represents only the coding sequence of the protein.

FIG. 3: Multiple sequence alignment of FRAP from *Plasmodium* and *Theileria* parasites. Sequences were aligned using the Clustal W algorithm. Amino acids in bold (60 total) represent residues that are conserved across the two genera of phylum apicomplexa. Residues marked with an asterisk represent amino acid positions that are identical only in the Plasmodial genus. Overall, the Plasmodial sequences have 60% sequence identity. FAS1 domain of FRAP has been aligned with the consensus sequence of FAS1 domain (SEQ ID NO: 21) and has an e-value of 2e- 10. The two conserved motifs have been underlined.

FIG. 6. Nature of FRAP receptor on liver cells. Binding activity of the FRAP proteins was evaluated on liver cells in the absence or presence of different concentrations of heparin and Chondroitin sulfate A. Panel A: FRAP; Panel B: FRAP2. Blank and hashed bars represent inhibition of binding activity in the presence of different concentrations of heparin and chondroitin sulfate A, respectively.

FIG. 7. Overlap between FRAP-based peptides. Ten overlapping peptides spanning the FRAP2 sequence were synthesized and utilized for the identification of regions(s) recognized by antibodies specific for FRAP.

FIG. 15 A and B. A, amino acid and B, nucleic acid encoding the FRAP2 derivative of FRAP.

DETAILED DESCRIPTION OF THE PREFERRED EMBODIMENTS OF THE INVENTION

Figure 4A:
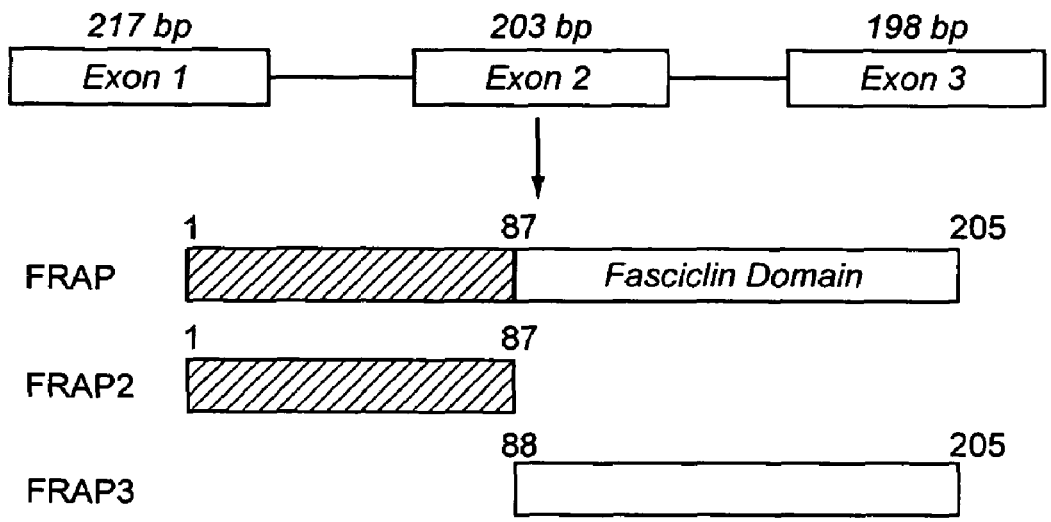
FIG. 4. Schematic representation of *P. falciparum* FRAP gene organization and the expressed recombinant proteins. (A) FRAP represents the full length protein encoding 205 amino acids. FRAP 2 represents a truncated version of the full length protein containing only amino acids 1-87, while FRAP 3 represents amino acids 88-205, encoding the Fasciclin 1 domain. (B) RT-PCR analysis of PfFRAP. DNA encoding the coding region of FRAP was amplified by RT-PCR using total RNA from sporozoite stage of the parasite's lifecycle. The amplification was performed in the presence (+RT) and absence of reverse transcriptase (−RT) to rule out the direct amplification from any contaminating genomic DNA. (C) Recombinant Expression and Purification of PEFRAP proteins. Full-length FRAP (lane 1) and its truncated variants, FRAP2 (lane 2) and FRAP3 (lane 3) were purified to homogeneity by a two step chromatography. (D) Western Blot analysis. Purified proteins were resolved on a 12% Nu-PAGE gel; transferred onto a nitrocellulose membrane and the membrane was probed using anti-FRAP2 antibody followed by an anti-mouse HRP conjugate.

The present invention is based on the discovery of several surprising properties of a previously uncharacterized family of parasite proteins. The protein family has been designated "FRAP" for "Fasciclin Related Adhesive Protein". FRAP, expressed by *Plasmodium* and *Theileria* parasites, is intimately involved in the onset of parasitic infections. Hence, the FRAP family of proteins, and the nucleic acids that encode them, are ideal targets for the treatment and/or prevention of certain parasitic diseases.

The initial FRAP protein was selected for study based on a systematic analysis of the genome of *Plasmodium falciparum* using a combination of in-silico algorithms, microarray and proteomic techniques. This process is described in detail in Example 1 of the Examples section. The study predicted that FRAP should be expressed on the surface of the *P. falciparum* sporozoite, and thus would be involved in early interactions between the sporozoite and host cells, making it an attractive target for therapeutic intervention. These predictions have been confirmed. FRAP protein is present in micronemes, a specialized secretory organelle that transports proteins to the surface of the *Plasmodium* sporozoite. FRAP and an 87 amino acid polypeptide derivative, FRAP2 (amino acid sequence, SEQ ID NO: 25; nucleic acid sequence, SEQ ID NO: 26; FIG. 15) bind to liver cells, thereby preventing sporozoite invasion. Further, antibodies specific for FRAP2 also prevent sporozoite invasion of liver cells. A thirty-two amino acid sequence that is recognized by these antibodies, encodes the inhibitory epitope and is common to the FRAP family of proteins (TRSGGLRKPQKVTNDPESINRKVYWCFE-HKPV, SEQ ID NO: 24), has also been discovered. This sequence shows 100% sequence homology and 87.5% sequence identity within the *Plasmodium* genus. In addition, the enzymatic activity of FRAP has been elucidated. FRAP catalyzes the neutralization of toxic heme into non-toxic hemozoin, making this protein a highly significant target for inhibitory drug therapy.

Herein we describe the application of these discoveries to the prevention and treatment of parasitic diseases. For example, FRAP proteins and various derivatives of FRAP proteins, including the antigenic epitope, and the nucleic acids that encode them, are useful as vaccine components. In addition, the inhibition of FRAP proteins or nucleic acids that encode them (e.g. by compounds that bind to the active site of the protein, or by RNA silencing) also provides a strategy for therapeutic intervention in parasitic disease. Further, the invention provides diagnostic tools related to the detection of parasites harboring either the FRAP protein or nucleic acids encoding FRAP. These and other aspects of the invention are discussed in detail below.

The FRAP protein that was first identified originated from *P. falciparum* and is represented by SEQ ID NO: 1 (see FIG. 1). The protein is encoded by the nucleic acid sequence represented by SEQ ID NO: 2 (FIG. 2). However, the FRAP family of proteins is not limited to those originating from *P. falciparum*. FRAP orthologs from *Plasmodium* species other than *P. falciparum* have been identified, for example, FRAP orthologs from human (*P. vivax*) simian (*P. knowlesi, P. reichenowi*), avian (*P. gallinaceum*) and rodent (*P. berghei, P. yoelii* and *P. chaubaudi*) malaria parasites. Overall, FRAP has extremely high sequence homology across the *Plasmodium* genus and the region encoding the inhibitory epitope identified in *P. falciparum* protein is very highly conserved in all known FRAP orthologs. Furthermore, polymerization of human heme into hemozoin by FRAP from rodent malaria parasite *P. yoelii* has been demonstrated. Therefore, FRAP sequences between different species of the parasites are functionally interchangeable and transgenic malaria parasites expressing the FRAP sequence from any member of the *Plasmodium* genus can be utilized for human malaria drug and for vaccine development. In addition, FRAP orthologs present in many related species such as *Theileria* may also be utilized for use in drug and vaccine development for the diseases they cause, e.g. bovine tropical theileriosis (Preston et al., Inate and adaptive immune responses co-operate to protect cattle against *Theileria annulata*. Parasitol Today. 1999 July; 15(7): 268-74). All such orthologs, examples of which are given in FIG. 1, are encompassed by the present invention. The nucleic acids that encode some exemplary FRAP proteins are presented in FIG. 2.

Those of skill in the art will recognize that a FRAP protein need not have an exact sequence as depicted in FIG. 1 in order to be suitable for use in the practice of the present invention. Rather, the invention also encompasses variants (derivatives) of such proteins. The term "protein" as used herein refers to sequences of about 100 or more amino acids; and the term "polypeptide" refers to sequences of about 100 amino acids or less, although these terms may be used interchangeably. (Shorter sequences, e.g. about 35 or fewer amino acids, will generally be referred to as peptides.) Variants or derivatives of FRAP proteins may be isolated from nature or be purposefully constructed. The primary sequence of such a variant or derivative may differ from the original sequence (e.g. as represented in FIG. 1) in any of several ways, including the following: conservative amino acid substitutions; non-conservative amino acid substitutions; truncation by, for example, deletion of amino acids at the amino or carboxy terminus, or internally within the molecule; or by addition of amino acids at the amino or carboxy terminus, or internally within the molecule (e.g. the addition of a histidine tag for purposes of facilitating protein isolation, the substitution of residues to alter solubility properties, the replacement of residues which comprise protease cleavage sites to eliminate cleavage and increase stability, the replacement of residues to form a convenient protease cleavage site, the addition or elimination of glycosylation sites, and the like, for any reason). Such variants may be naturally occurring (e.g. as the result of natural variations between species or between individuals, or as a result of different expression systems used to produce the amino acid sequence, etc.); or they may be purposefully introduced (e.g. in a laboratory setting using genetic engineering techniques). The amino acid sequences may be in a variety of forms, including a neutral (uncharged) forms, or forms which are salts, and may contain modifications such as glycosylation, side chain oxidation or deamidation, phosphorylation and the like. Also included are amino acid sequences modified by additional substituents such as glycosyl units, lipids, or inorganic ions such as phosphates, as well as modifications relating to chemical conversions or the chains, such as oxidation of sulfhydryl groups.

All such variants of the amino acid sequences disclosed herein are intended to be encompassed by the teachings of the present invention, provided the variant protein/polypeptide displays sufficient identity to the original sequence as disclosed herein, or an amino acid sequence that can be translated from a nucleic acid sequence disclosed herein. Preferably, amino acid identity will be in the range of about 50 to 100%, and preferably about 60 to 100%, or more preferably about 70 to 100%, or even more preferably about 80 to 100%, or most preferably about 90 to 100%, or even about 95 to 100%, of the disclosed sequences. The identity is with reference to the portion of the amino acid sequence that corresponds to the original amino acid sequence as translated directly from the nucleic acid sequences disclosed herein, i.e. not including additional elements that might be added, such as sequences added to form chimeric proteins, histidine tags, etc. Those of skill in the art are well acquainted with the methods available for determining the identity between amino acid sequences, for example, FASTA, FASTP, the BLAST suite of comparison software, ClustalW, Lineup, Pileup, or many other alignment software packages.

In addition, such protein/polypeptide variants retain at least about 50 to 100% or more of the activity of the original polypeptide, and preferably about 60 to 100% or more, or more preferably about 70 to 100% or more, or even more preferably about 80 to 100% or more, and most preferably about 90 to 100% or more of the activity of the original sequence. By "activity" we mean the activity or role of the amino acid sequence in the parasite from which is was isolated, which may include but is not limited to: characteristic enzyme activity, activity as a structural component, role as a membrane component, binding activity, etc.

The peptides, polypeptides and proteins of the present invention are generally provided as recombinant molecules, although the amino acid sequences may also be produced synthetically via known peptide synthesis techniques. The peptides, polypeptides and proteins of the present invention are provided in a substantially purified form, i.e. they are generally free of extraneous materials (such as other proteins, nucleic acids, lipids, cellular debris, etc.) and will generally be at least about 75% pure, preferably about 85% pure, and most preferably at least about 90-95% or more pure, as would be understood by one of ordinary skill in the art.

In general, the proteins and polypeptides of the invention are produced in recombinant expression systems. In a preferred embodiment of the present invention, the recombinant system is an *E. coli* recombinant system. However, they may also be produced in a variety of other recombinant expression systems. For example, yeast, insect cells (using for example, a baculovirus expression vector), plant cells (e.g. tobacco, potato, corn, etc.), transgenic animals, or mammalian cell culture systems can be used for expression of recombinant proteins. Any appropriate expression system that suitably produces the proteins and polypeptides of the invention may be used in the practice of the invention. Such systems and their use for the production of recombinant proteins are well known to those of ordinary skill in the art.

The invention also provides antigenic peptides, in particular an antigenic epitope common to the FRAP family of proteins. The epitope has the amino acid sequence TRSGGL-RKPQKVTNDPESINRKVYWCFEHKPV (SEQ ID NO: 24). Some modification of this sequence may be tolerated without compromising the antigenicity of the sequence. Those of skill in the art will recognize that peptides may be obtained by several means, including but not limited to chemical synthesis methods, production using genetic engineering techniques, enzymatic digestion of larger polypeptides, etc. The particular source of a peptide is not a crucial feature of the invention. In a preferred embodiment, the peptide will be chemically synthesized. In some embodiments of the invention, the FRAP epitope will be used as an antigen in combination with at least one other known parasite antigenic epitope. For example, genetic engineering techniques may be employed to construct chimeric polypeptides or proteins containing two or more of such epitopes on the same molecule. Alternatively, separate preparations of the peptidic epitopes may be prepared and mixed into a single solution, for example, to be administered as a vaccine.

In addition to utilizing FRAP proteins, polypeptides and peptides, the present invention also encompasses use of the nucleic acids that encode such amino acid sequences. Exemplary DNA sequences that encode FRAP proteins are given in FIG. 2A-J. The nucleic acids may be used as a tool, e.g. to produce a protein. Alternatively, the nucleic acid sequences themselves may be used in certain aspects of the invention, e.g. as components of DNA vaccines, or for gene silencing applications (see below). Those of skill in the art will recognize that many variants (derivatives) of such sequences may exist in nature or be constructed which would still be suitable for use in the practice of the present invention. For example, with respect to the translation of amino acid sequences from the nucleic acid sequences, due to the redundancy of the genetic code, more than one codon may be used to code for an amino acid. Further, as described above, changes in the amino acid primary sequence may be desired, and this would necessitate changes in the encoding nucleic acid sequences. In addition, those of skill in the art will recognize that many variations of the nucleic acid sequences may be constructed for purposes related to other aspects of the invention, for example: for cloning strategies (e.g. the introduction of restriction enzyme cleavage sites for ease of manipulation of a sequence for insertion into a vector, for rendering the sequence compatible with the cloning system vector or host, for enabling fluorescent or affinity labeling technologies, etc.), for purposes of modifying transcription (e.g. the introduction of specific promoter or enhancer sequences, insertion or deletion of splice signals, for enhancing or negatively regulating transcription levels, for regulating polyadenylation, for controlling termination, and the like), or for modification of active or inactive domains, for elimination or modification of certain activities or domains, for optimizing expression due to codon usage or other compositional biases, for addition of immunologically relevant (enhancing or inhibiting) sequences or for any other suitable purpose. All such variants of the nucleic acid sequences encoding the proteins, polypeptides and peptides disclosed herein are intended to be encompassed by the present invention, provided the sequences display homology in the range of about 50 to 100%, and preferably about 60 to 100%, or more preferably about 70 to 100%, or even more preferably about 80 to 100%, or most preferably about 90 to 100% or about 95 to 100% to the disclosed sequences. The homology is with reference to the portion of the nucleic acid sequence that corresponds to the original sequence, and is not intended to apply to additional elements such as promoters, vector-derived sequences, restriction enzyme cleavage sites, etc. derived from other sources. Those of skill in the art are well-acquainted with methods to determine nucleic acid similarity or identity using simple software alignment tools such as FASTA, the BLAST suite of programs, CLUSTAL W, Lineup, Pileup (GCG), or many others.

In addition, the nucleic acids are not limited to DNA, but are intended to encompass other nucleic acids as well, such as MRNA, RNA-DNA hybrids, and various modified forms of DNA and RNA known to those of skill in the art. For example, for use in vivo, nucleic acids may be modified to resist degradation via structural modification (e.g. by the introduction of secondary structures, such as stem loops, or via phosphate backbone modifications, etc.) Alternatively, the nucleic acids may include phosphothioate or phosphodithioate rather than phosphodiesterase linkages within the backbone of the molecule, or methylphosphorothiate terminal linkages. Other variations include but are not limited to: nontraditional bases such as inosine and queosine; acetyl-, thio- and similarly modified forms of adenine, cytidine, guanine, thymine and uridine; stabilized nucleic acid molecules such as nonionic DNA analogs, alkyl-and aryl phosphonates; nucleic acid molecules which contain a diol, such as tetrahyleneglycol or hexaethyleneglycol, at either or both termini; etc. Further, the nucleic acid molecules may be either single or double stranded, or may comprise segments of both single and double strand nucleic acid.

In the course of practicing the invention, FRAP-related nucleic acid molecules may be cloned into one of many suitable vectors. In some embodiments, vectors containing nucleic acid sequences (e.g. DNA) that encode the amino acid sequences of the invention will encode a single protein, polypeptide, or peptide. However, this need not always be the case. Such vectors may contain DNA encoding more than one amino acid sequence, either as separate, discrete sequences, or combined into a single chimeric sequence. For example, in the case of an expression vector, two or more nucleic acids according to the invention may be present in the vector, and the nucleic acids may be expressed separately, resulting in the translation of one amino acid sequence for each nucleic acid. Alternatively, a single polypeptide chain containing more than one amino acid sequence of the invention, or portions of more than one amino acid sequence of the invention, may be combined in tandem. For example, one or more highly antigenic proteins or regions of proteins of the invention may be expressed as a chimera from a single DNA sequence. Alternatively, the amino acid sequences of the invention may be expressed as part of a chimeric protein comprising amino acid sequences from another source, e.g. antigenic sequences known to be useful as adjuvants (e.g. PADRE [and other Pan-DR T helper cell epitope], hepatitis B core antigen, DNA sequences CPG, other chemokines, CTB or cholera toxin B subunit, Ricin B and other plant toxin subunits, LPS or lipopolysaccharide, KLH [key hole limpet hemocyanin], Freund's complete and Freund's incomplete adjuvant, and many other reagents, etc. ), sequences that permit targeting of the protein to a specific location within the cell (e.g. nucleus, nucleolus or nuclear membrane, mitochondrion/mitosome/ mitochondria-like organelle, membrane, endoplasmic reticulum, golgi, rhoptry, dense granules, calcisomes or acidocalcisomes, and other subcellular organelles compartments, etc.).

One application of the present invention is the provision of vaccines that provide immunity to disease caused by parasites such as *Plasmodium*. By "immunity" we mean that administration to an individual of one or more proteins, polypeptides or peptides of the invention, or nucleic acids encoding them, either alone or in combination with other antigenic entities prevents the development of disease symptoms in that individual after exposure to or infection by a parasite. Alternatively, the disease symptoms that develop in the individual may be milder than those that would otherwise develop in, for example, a matched control individual. Those of skill in the art are well acquainted with the use and meaning of "controls" when comparing results of individuals or populations that have been exposed to different variables (e.g. vaccinated or not). In particular, the inhibitory epitope peptide of the invention may be used in combination with one or more other antigenic epitopes for the production of a multicomponent vaccine. Such a vaccine addresses previous lackluster vaccine performance by presenting several highly immunogenic epitopes to the immune system of a vaccinated individual in a single preparation. This type of vaccine closely mimics the natural in vivo presentation of antigens on the surface of a parasite, and thus elicits a robust immune response.

According to an embodiment of the invention, the vaccine may either be prophylactic (i.e. to prevent or attenuate symptoms of infection) or therapeutic (i.e. to treat disease after infection). Such vaccines comprise one or more of: immunizing antigen(s), immunogen(s), polypeptide(s), protein(s) and nucleic acid(s) from the FRAP family (as described herein), usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens. Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor, etc; and (6) other substances that act as immunostimulating agents to enhance the effectiveness of the composition. Alum and MF59™ are preferred.

The immunogenic compositions (eg. the immunizing antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles. Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for eliciting the production of antibodies, for eliciting a cellular immune response, (or both), and/or for treatment or prevention of disease. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. The immunogenic compositions are conventionally administered parenterally, eg. by injection, either subcutaneously, intramuscularly, intranasally, or transdermally/transcutaneously. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents. As an alternative to protein-based vaccines, DNA vaccination may be employed [eg. Robinson & Torres (1997) *Seminars in Immunology* 9:271-283; Donnelly et al. (1997) *Annu Rev Immunol* 15:617-648].

Vaccines can be composed of live, attenuated or killed organisms, or chemically inactivated toxins (toxoids), against which the body can raise an effective immune response, leading to effective protection against the live agent or active toxins produced during the infection. Combination vaccines make it possible to immunize individuals against multiple pathogens at a time. Examples of combination vaccines are DTaP (Diphtheria, Tetanus, combined with acellular Pertussis) or MMR (Measles, Mumps, and Rubella). Conjugated vaccines, such as PCV (Pneumococcal Conjugated Vaccine) provide better immunization of infants. In conjugated vaccines polysaccharide antigens are chemically linked to protein antigens which provide a better stimulus for the immature immune system. Through the use of recombinant DNA technology it is possible to isolate and express individual genes or combinations of genes, encoding antigens from pathogens and produce vaccines by fermentation. Recent advances in genomics and proteomics of (re-)emerging pathogens will enable entirely new generations of vaccine based on identification of surface proteins. Table 1 lists common types of vaccines in current use or in development, and some important attributes.

TABLE 1

Vaccine types in current use and development

| Type | Vaccine | Advantages | Disadvantages |
| --- | --- | --- | --- |
| Live, attenuated vaccines | Measles, mumps, rubella, polio (Sabin vaccine), yellow fever | Produce a strong immune response; often give lifelong immunity with one or two doses | Remote possibility that the live microbe could mutate back to a virulent form; must be refrigerated to stay potent |
| Inactivated or "killed" vaccines | Cholera, flu, hepatitis A, Japanese encephalitis, plague, polio (Salk vaccine), rabies | Safer and more stable than live vaccines; don't require refrigeration; more easily stored, transported | Produce a weaker immune response than live vaccines; usually require additional doses |
| Toxoid vaccine | Diphtheria, tetanus | Teaches immune system to fight off bacterial toxins; often easy to produce | Protect only against deleterious effect of toxin, but do not provide protection from pathogen |
| Subunit vaccines | Hepatitis B, pertussis, pneumonia caused by *Streptococcus pneumoniae* | Targeted to very specific parts of the microbe; fewer antigens, so lower chance of adverse reactions | When developing a new vaccine, identifying the best antigens can be difficult and time consuming |
| Conjugate vaccines | *Haemophilus influenzae* type B, pneumonia caused by *Streptococcus pneumoniae* | Allow infant immune systems to recognize certain antigens | |
| DNA vaccines | In development | Produce a strong antibody and cellular immune response; relatively easy and inexpensive to produce | Still in experimental stages |

TABLE 1-continued

Vaccine types in current use and development

| Type | Vaccine | Advantages | Disadvantages |
|---|---|---|---|
| Recombinant vector vaccines | In development | Closely mimic a natural infection, stimulating a strong immune response | Still in experimental stages |

Source: Understanding Vaccines: What they are, how they work. U.S. DHHS/NIH/NIAID, NIH Publication No. 03-4219, 2003.

Most vaccines in Table 1 are administered by subcutaneous or intramuscular injection. The oral route of administration is occasionally used in case of Oral Polio Vaccine. New vaccine technology is being developed to produce vaccines that (i) generate stronger and broader immunity, (ii) meet more stringent safety and quality requirements, and (iii) that have greater ease of delivery at lower cost. Therefore, a significant amount of research is ongoing to develop new delivery methods and adjuvants. For effective immunization most vaccines are delivered using adjuvants. Adjuvants are emulsions or formulations, often containing lipids or aluminum salts, which provide for slow release of the antigen into the plasma, and also stimulate the immune response in ways that are not fully understood. Slow release of the antigen is also important to prevent metabolism and removal from the plasma prior to the initiation of the immune response. Delivery of antigen to the cells that participate in antigen presentation, macrophages and dendritic cells, is also improved by the use of adjuvants. Table 2 lists a number of commonly used adjuvants and new adjuvant delivery methods in development.

TABLE 2

Commonly used adjuvants and new products in development.

| Adjuvant Category | New product or method | Comments/Examples |
|---|---|---|
| Gel type | Aluminum hydroxide/phosphate | Improve delivery to APCs and secondary lymphoid organs |
|  | Calcium phosphate |  |
| Microbial | Muramyl dipeptide (MDP) |  |
|  | Bacterial exotoxins | Cholera toxin (CT) |
|  | Endotoxin based adjuvants | *Escherichia coli* heat labile toxin (LT) |
|  |  | Monophosphoryl lipid A (MLA) |
| Particulate | Biodegradable polymer microspheres |  |
|  | Immuno-stimulatory complexes (ISCOMs) |  |
|  | Liposomes |  |
| Oil emulsion/ surfactant | Freunds incomplete adjuvant | Animal experimental uses only |
|  | Microfluidized emulsions | MF59 (Squalene), SAF |
|  | Saponins | Qs-21 |
| Synthetic | Muramyl peptide derivatives | Murabutide, Threonyl-MDP |
|  | Non-ionic block co-polymers | L121 |
|  | Polyphosphazene (PCPP) |  |
| Cytokines | Interleukin-2, -12 | Molecules secreted by macrophages or dendritic cells that stimulate the inflammatory and immune response |
|  | GM-CSF |  |
|  | Interferon gamma |  |
| Genetic | Genes encoding cytokines or co-stimulatory molecules delivered by plasmids | IL-12, IL-2, LFNg, CD40L |

Sources: Progress in Immunologic Adjuvant Development 1982-2002, The Jordan Report 2002, US DHHS/NIH/NIAID, and the website located at www.niaid.nih.gov/daids/vaccine/pdf/compendium.pdf.

New physical administration methods being developed include delivery by inhalation, oral delivery, or transdermal delivery. Inhalation delivery includes intranasal delivery for delivery to the upper respiratory tract, which is being used in FluMist (influenza vaccine) or other powder or particle based methods to deliver immunization to the lower respiratory tract. Oral delivery includes new formulations to allow antigens to pass through the stomach and intestinal tract without acid or protease inactivation. New methods of oral delivery include edible vaccines, where plants such as potatoes, tomatoes, or bananas are genetically engineered to express the antigen in parts of the plant that are consumed by humans. New transdermal delivery methods that avoid injection are being explored as well. However the large size (high molecular weight) of the antigen(s) usually is a limitation for this delivery method. A relatively new delivery method is expression of antigens in a strain of virus or a bacterium that is not naturally pathogenic, or is made avirulent either through mutation or genetic engineering. Attenuated viruses such as polio, or bacteria such as *Vibrio cholerae* and *Salmonella typhi*, are being explored as delivery vehicles.

Production methods for vaccines vary with the type of vaccine. Live, attenuated or killed virus vaccines are produced in mammalian cell culture. In the latter case virus particles are killed by chemical inactivation, heat or radiation. A major concern of mammalian cell culture based production methods is contamination with other pathogens, specifically retroviruses such as HIV, or other as of yet uncharacterized mammalian viruses. Influenza vaccine is produced either through cell culture or growth of virus in fertilized chicken eggs, followed by purification from the yolk. Live, attenuated or killed bacterial vaccines are produced by microbial fermentation. Concerns with this method are contamination with other micro-organisms (bio-burden), or presence of bacterial endo- or exo-toxins that can cause anaphylactic shock. Toxoid vaccines, such as diphtheria or tetanus vaccines, are produced by microbial fermentation and harvesting of the exo-toxins from the culture medium. Toxoid vaccines can also be produced with recombinant DNA technology, followed by purification of the recombinant protein. Conjugated vaccine components are produced through multiple methods. The polysaccharide component is harvested from bacteria grown in culture, and the protein component of the antigen can be produced through fermentation or recombinant DNA technology. The conjugation step is done through a chemical reaction. Subunit vaccines, existing of specific protein antigens (or combinations) are made through fermentation or recombinant DNA technology. Other transgenic production methods, such as expression in the milk of transgenic animals, or production in genetically engineered plants, are being explored for subunit vaccines as well. DNA vaccines are produced using recombinant DNA technology. Vector vaccines are produced through genetic engineering of the vector, i.e. to produce the antigens of interest, and either microbial fermentation or mammalian cell culture.

In particular, with respect to DNA vaccines, U.S. Pat. No. 6,214,804 (Felgner, et al., 2001, the complete contents of which is hereby incorporated by reference) describes the induction of a protective immune response in a mammal by injecting a DNA sequence. Methods for delivering an isolated polynucleotide to the interior of a cell in a vertebrate are provided. The methods can be used to deliver a therapeutic polypeptide to the cells of the vertebrate, to provide an immune response upon in vivo translation of the polynucleotide, to deliver antisense polynucleotides, to deliver receptors to the cells of the vertebrate, or to provide transitory gene therapy.

In addition, U.S. Pat. No. 6,923,958 (Xiang et al., 2005, the complete contents of which is hereby incorporated by reference) describes DNA vaccines encoding carcinoembryonic antigen (CEA) and a CD40 ligand and methods of their use. The DNA vaccine is effective for eliciting an immune response against cells that present a carcinoembryonic antigen, and could be incorporated in a delivery vector such as an attenuated live bacterium or virus, or a liposome carrier. Alternatively, the DNA vaccine is administered orally to a mammal, such as a human, to elicit an immune response against CEA presenting cells such as colon cancer cells. The mammal may be further treated with recombinant antibody fusion proteins to enhance the immune response effectiveness of the vaccine.

Another embodiment of the invention provides antibodies specific for FRAP proteins, polypeptides and peptides. As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows binding of the antibody with the antigen. "Antibody" includes, for example, vertebrate antibodies, hybrid antibodies, chimeric antibodies, humanised antibodies, fully human antibodies, altered antibodies, univalent antibodies, Fab proteins and fragments, and single domain antibodies. Antibodies to the polypeptides and peptides of the invention, both polyclonal and monoclonal, may be prepared by conventional methods that are well-known to those of skill in the art. If desired, the antibodies (whether polyclonal or monoclonal) may also be labeled using conventional techniques.

Antibodies for therapeutic applications for the prevention or treatment of malarial disease, or diagnostic applications in the detection of parasite infection, can be made by standard methods. In most cases the antibodies will be of monoclonal origin, and either produced in rats or mice.

Protein for immunization is made by recombinant methods. Any of the proteins from the group of SEQ ID NOS: 1, 3, 5, 7, 9, 11, 13, 15, 17, and 19, or portions thereof, can be produced by cloning the corresponding DNA sequences of SEQ ID NOS: 2, 4, 6, 8, 10, 12, 14, 16, 18, and 20, or portions thereof, in recombinant protein expression vectors. Protein can be produced in this manner in *E. coli*, yeast, fungi, plants, mammalian, or insect cells. It is obvious that the preferred protein used for immunization is from the *Plasmodium* species that infect humans, i.e. SEQ ID NOS: 1 and 7. However, in principle SEQ ID NOS: 3, 5, 9, 11, 13 and 15, could also be used to generate antibodies that are effective as therapeutics or diagnostic tools. Immunization material for short peptides and small proteins can also be made through chemical synthesis.

For example the 8-mer peptide represented by SEQ ID NO: 37 may be encoded by: ACCAACGACCC AGAAAG-TATAAAT (SEQ ID 38), or other sequences; and the 32-mer peptide represented by SEQ ID NO: 24 may be encoded by: ACACGAAGTGGCGGTTTAAGAAAACCTCAAAAGG TAACCAACGACCCAGAAAGT ATAAATAGAAAAG-TATATTGGTGTTTTGAACATAA GCCTGTA (SEQ ID 39), or other sequences. Alternatively, the these peptides may be chemically synthesized.

Expressed protein can be purified with standard HPLC and other chromatographic methods, in quantities and sufficient purity to be injected in the mice or standard rats. Rats or mice are injected in the presence of adjuvants, and in a standard schedule of injections and boosters, in order to generate a vigorous immune response. In order to make monoclonal antibodies, spleen cells are harvested from the animals and fused with immortalized cell lines. Numerous immortalized cell lines are screened for their ability to secrete antibodies that bind the original antigen used in immunizations. Positive cell lines are purified and cloned, and their antibodies are characterized and screened to identify antibodies that have strong binding characteristics. Upon identification of such cell lines, the antibody genes are cloned, sequenced and can be used to engineer mammalian cell culture strains for high level production.

In order to avoid a human immune response against the therapeutic antibody, the sequence of the monoclonal antibody is modified to most closely resemble the sequence of native human antibodies. This is done by recombinant DNA methods, through selective replacement of the significant portions of the murine antibody light and heavy chain sequences with human sequences (chimeras), or through replacement of almost all of the non-variable sections of the murine antibody light and heavy chains, with those from human antibody chain conserved sequences, while maintaining the original rat or mouse sequence of the hyper-variable domain which is responsible for antigen recognition and binding ('CDR grafting' or 'humanization'). For example U.S. Pat. No. 6,500,931 describes the method of humanizing antibodies.

Alternatively, fully human monoclonal antibodies can be made in mice directly, when these mice are engineered to produce only human antibody chains. For example the technology practiced by companies such as Abgenix Inc. [XenoMouse technology, U.S. Pat. No. 6,657,103], Medarex Inc. and GenMab A/S [HuMab Mouse or UltiMAB technology; WO2005023177] can be used. Purified proteins as described above are used to immunize such engineered mice. Monoclonals produced in this manner are produced, screened and characterized in the standard manner. Fully human antibodies can also be produced using phage display methods by screening against human antibody phage display libraries. For example technologies practiced by companies such as Cambridge Antibody Technology [U.S. Pat. No. 5,969,108 and U.S. Pat. No. 6,172,197] and others, can be used to identify fully human antibodies in this manner. Phage display screening has an added advantage in that the process does not rely on animal immunization. The genes for fully human antibodies produced using engineered mice, or identified through phage display, can be isolated, sequenced and cloned for expression in mammalian cell lines for high level expression using standard methods.

Patents describing this technology in detail are incorporated herein by reference.

Such antibodies may be used, for example, for affinity chromatography, immunoassays, and for distinguishing or identifying parasite proteins or portions thereof. In a preferred embodiment of the invention, such antibodies may be used therapeutically, e.g. for administration to patients suffering from a parasitic disease such as malaria, or prophylactically in order to prevent a parasitic disease in patients at risk for developing the disease.

In yet another embodiments of the invention cells or cell lines containing the nucleic acids and/or the amino acid sequences of the invention as described herein. For example, the cell may be a host cell that harbors one or more vectors containing nucleic acid sequences used in the invention (e.g. DNA or RNA) and/or amino acid sequences of the invention translated from such vectors. Such cells may contain multiple vectors, and the vectors may be the same or different. Further, the cells may be either in vitro or in vivo.

The invention also comprehends pharmaceutical compositions and their use. The pharmaceutical compositions can comprise one or more proteins, polypeptides, peptides, antibodies, or nucleic acids according to the invention, or combinations of these. The pharmaceutical compositions comprise a therapeutically effective amount of such molecules.

The term "therapeutically effective amount" as used herein refers to an amount of a therapeutic agent that is sufficient to treat, ameliorate, or prevent a disease or condition, or to exhibit a detectable therapeutic or preventative effect. The effect can be detected by, for example, chemical markers or antigen levels. Therapeutic effects also include reduction of physical symptoms of the parasitic disease. The precise effective amount for a subject will depend upon several parameters, including the subject's size, general health, gender, age, etc., and the therapeutics or combination of therapeutics selected for administration. Thus, it is not useful to specify an exact effective amount in advance. However, the effective amount for a given situation can be determined by routine experimentation and is within the judgement of those of skill in the art, e.g. a physician. For purposes of the present invention, an effective dose will be from about 0.01 mg/kg to 50 mg/kg or about 0.05 mg/kg to about 10 mg/kg of active, therapeutic agent.

A pharmaceutical composition may also contain a pharmaceutically acceptable carrier. The term "pharmaceutically acceptable carrier" refers to a carrier for administration of a therapeutic agent, such as antibodies or a polypeptide, genes, and other therapeutic agents. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's *Pharmaceutical Sciences* (Mack Pub. Co., N.J. 1991).

In addition, pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Once formulated, the compositions of the invention are administered to the subject. The subjects to be treated may be animals; in particular, human subjects can be treated. Direct delivery of the compositions will generally be accomplished by injection, either subcutaneously, intraperitoneally, intravenously or intramuscularly or delivered to the interstitial space of a tissue. Other modes of administration include oral and pulmonary administration, suppositories, and intranasal, transdermal or transcutaneous applications (eg. see WO98/20734), needles, and gene guns or hyposprays. Dosage treatment may be a single dose schedule or a multiple dose schedule.

Yet another embodiment of the invention provides tools and methods for the diagnosis of parasitic infections. Such tools include primers containing nucleotide sequences that specifically hybridize to nucleic acid sequences that are unique to FRAP. Hybridization of the primers to such a unique sequence permits amplification of the unique sequence (for example, by polymerase chain reaction (PCR)), thus providing a means to specifically identify the presence of FRAP in biological samples (blood, feces, sputum, urine, bronchoaveloar lavage, etc.). Amplification may be directly from the genome of the organism located in the sample, or from RNA, e.g. mRNA.

By "primer" we mean a nucleotide sequence that hybridizes to another nucleotide sequence of interest, the primer typically being a relatively short nucleotide sequence (e.g. from about 10 to about 100 base pairs) and the nucleotide sequence of interest typically being transcribed from the genome of an organism. PCR amplification techniques are well-known to those of skill in the art. In general, two primers are selected that target sites that flank the sequence of interest (e.g. a gene encoding FRAP) for diagnostics or identification. These primers are designed to recognize only the target sequence; i.e., they will hybridize only to the target sequence and to no other sequences. The primers generally range from 18-30 nucleotides in length (but can be longer or shorter), have Tm's (melting temperatures) that are selected to be compatible with both amplification conditions and with specificity, have little or no internal structure (stem-loop structures caused by internal complementarity), little or no ability to dimerize with themselves, little or no ability to dimerize with the other primer, have few homopolymeric stretches, etc. Many computer programs (e.g., Primer3, Oligo, etc.) are available for primer design. At times, an internal fluorescent probe is also included for specific use in even more sensitive and automated tests. The internal probe is fluorescently labeled such that it is specifically degraded and therefore fluoresces only if it specifically hybridizes to the target sequence. Alternately, other fluorescent probes can be designed that only fluoresce upon binding specifically to an amplified specific sequence. Thus, several alternative approaches are available for the generation and detection of specific sequences amplified by PCR, and any of these can be applied for diagnostic or identification purposes. (See, for example: Mullis, K., F. Faloona, S. Scharf, R. Saki, G. Horn, and H. Erlich. (1986) Specific enzymatic amplication of DNA in vitro: The Polymerase Chain Reaction. Cold Spring Harbor Symposia on Quantitative Biology 51: 263; Saiki, R. K., D. H. Gelfand, S. Stoffel, S. J. Scharf, R. Higuchi, G. T. Horn, K. B. Mullis, and H. A. Erlich. (1988) Primer-directed enzymatic amplification of DNA with a thermostable DNA polymerase. Science 239: 487; Schutzbank T E, Stern H J. (1993) Principles and applications of the polymerase chain reaction. J Int Fed Clin Chem. 1993 Jul; 5(3):96-105; Erlich H A. (1999) Principles and applications of the polymerase chain reaction. Rev Immunogenet. 1(2):127-34; Wang, A. M., Doyle, M. V., and D. F. Mark. (1989) Quantitation of mRNA by the polymerase chain reaction. Proc Natl Acad Sci U S A. 1989 December; 86(24): 9717-9721; Kawasaki, E. S., and A. M. Wang. (1989) Detection of gene expression. In: Erlich, H. A., ed., PCR Technology: Principles and Applications of DNA Amplification. Stockton Press, Inc., New York, N.Y., pp. 89-97; Dieter Klein (2002) Quantification using real-time PCR technology: applications and limitations. Trends in Molecular Medicine, 8(6):257-260; Buck GE. (1996) The polymerase chain reaction: a revolutionary new procedure for the laboratory diagnosis of infectious disease. J Ky Med Assoc. Apr; 94(4):148-52.)

Because the primers are unique to FRAP, a positive amplification result is indicative of the presence of FRAP in the biological sample, and thus of infection by a parasite whose genome encodes FRAP. Similar tests can be carried out with antibodies specific for FRAP. In this case, a positive result indicates that the biological sample being tested contains FRAP, and thus, by inference, the individual from whom the sample was obtained is infected with a parasite that produced FRAP.

The following Examples describe: the discovery and characterization of the novel FRAP protein family; the expression, localization and purification of recombinantly expressed FRAP; the generation of antibodies to FRAP2; experiments demonstrating the binding of FRAP to liver cells; prevention of sporozoite invasion of liver cells by FRAP and antibodies to FRAP2; discovery of the inhibitory epitope of FRAP; FRAP as a drug target; the use of FRAP in high throughput assays for hemozoin formation for screening novel antimalarials; siRNA mediated inhibition of FRAP; the creation of FRAP variant attenuated parasites for use as whole organism vaccines; and the use of FRAP as a tool for high levels of expression and purification of recombinant proteins.

EXAMPLES

Example 1

Discovery and Characterization of a Novel *Plasmodium Falciparum* Protein Involved in Malaria Pathogenesis

*Plasmodium* sporozoites adhere to and invade host liver cells, leading to the onset of malaria. Here we describe a novel, 205 amino acids long, *Plasmodium falciparum* protein involved in sporozoite-liver cell interactions. Orthologs of this protein were identified in seven other *Plasmodium* species, representing the four distinct phylogenetic clades, and the protein showed 60% sequence identity within the genus. Additionally, amino acids 88-205 have a 20% sequence identity to fasciclin 1, an ancient adhesive domain found in prokaryotes, plants and animal proteins. The DNA encoding the protein was cloned, expressed in *E. coli* and the protein was purified to homogeneity. Immunoelectron microscopy showed that the protein was localized in the micronemes of the sporozoites. The protein contributes to sporozoite's adhesion and invasion activities and antibodies raised against this protein can prevent >94% of *P. falciparum* sporozoites from invading liver cells, thus suggesting a role for this protein in malaria pathogenesis. Furthermore, we provide evidence that the protein exploits heparan sulfate proteoglycans expressed on the liver cell surface as its receptor. Due to its role in host cell adhesion and the presence of fasciclin 1 domain, we have named this protein as Fasciclin Related Adhesive Protein or FRAP. Our results show that FRAP is an excellent target for malaria vaccine development.

A bite by a parasite-infected mosquito delivers *Plasmodium* sporozoites in the blood stream, which is followed by its entry into the liver cells. A successful adhesion and invasion of liver cells by the parasite sets the stage for rapid multiplication, development and subsequent release of parasites in circulation, leading to the erythrocytic infection and the clinical pathology associated with malaria. It is widely believed that the host cell adhesion and invasion is a multistep process involving several parasitic proteins, many of which are currently not known. Of these, Circumsporozoite (CS) and Sporozoite Surface Protein-2/Thrombospondin-Related Anonymous Protein (SSP2/TRAP), have been extensively investigated (1, 2). Across pathosystems, proteins involved in host-pathogen interactions are the molecules of choice for vaccine development. Likewise, CS and SSP2/TRAP have become major targets for intervention and are being actively pursued as vaccine candidates (3-6). While the results from these trials have been encouraging, they have revealed that the immunological protection against malaria is not conferred due to a dominant immune response against a single antigen but is mediated by the summation of many modest humoral and cell-mediated immune responses against a large variety of known and unknown antigens (7). Therefore, identification of malarial proteins that are involved in disease pathogenesis will not only lead to a better understanding of the disease process, but is also vital for the development of a successful vaccine against malaria. With the availability of the genome sequence and proteome analysis of *P. falciparum* parasites (8, 9), efforts are now being made to mine this information for identification and characterization of proteins that contribute towards pathogenesis (10).

In recent years, the concept of protein domains and domain families has risen to greater prominence due to an increasing realization that by organizing proteins sequences from distinct organisms into domain families, one can often reliably predict their molecular functions (11, 12). In case of pathogens, identification of adhesive domain-containing proteins has played a pivotal role in deciphering the mechanics of disease pathogenesis. For example, the *Plasmodium* genome encodes several proteins that contain an adhesive thrombospondin type I repeat (TSR) domain, most of which have now been shown to be involved in host-parasite interactions (1, 2, 10, 13). Therefore, identification and characterization of parasite proteins containing adhesive domains will improve our understanding of the disease process and here we describe a novel malarial protein that encodes a single fasciclin 1 (FAS1) domain.

Figure 3:
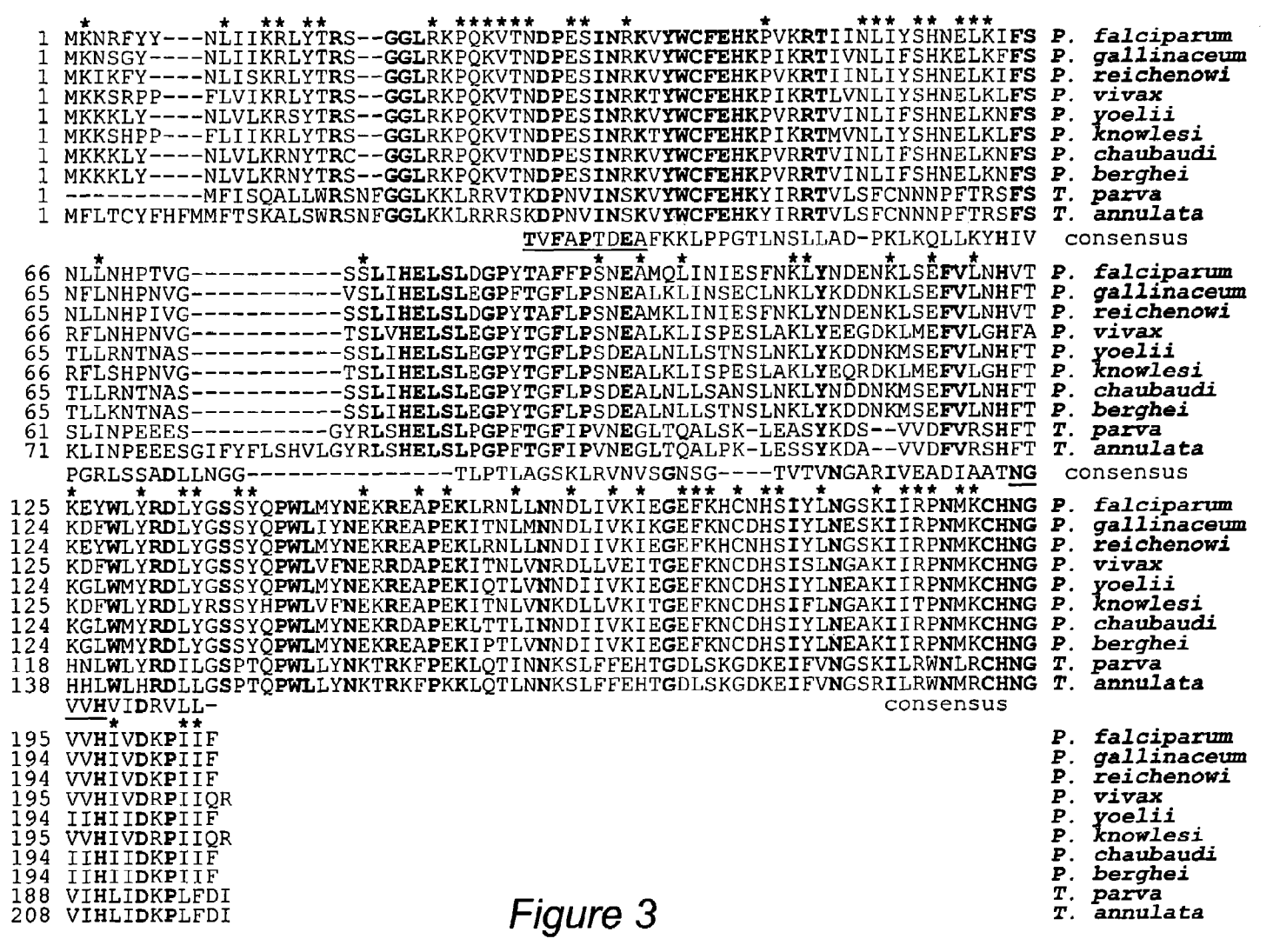

FAS 1 is an adhesive domain named due to its initial discovery in proteins involved in fasciculating axons and growth cones (14). It is an ancient extracellular adhesive module found in proteins of prokaryotic, plant and animal origin (15-18). Most of the FAS1 domain-containing proteins possess multiple copies of the domain, though proteins encoding only a single copy, have also been identified (17). A large number of FAS1 domain containing proteins have been reported in *Drosophila* and Grasshopper, where they are involved in neuronal development (19, 20). In contrast, in humans, FAS1 domains have been found in a large multi-domain scavenger receptor protein on endothelial cells, involved in the removal of hyaluronan from blood stream (21), as well as in extracellular matrix protein, where they mediate corneal epithelial cell adhesion (22). However, unlike many domains which show a high degree of sequence conservation, FAS1 domains show huge sequence diversity; typically have 20% sequence identity in a pairwise alignment (23) and are recognized by only two short semi-conserved sequence motifs (underlined in FIG. 3).

Here we describe a novel *P. falciparum* FAS1 domain-containing protein and its role in malaria infectivity during sporozoite stage of the lifecycle. We demonstrate that the protein contributes towards liver cell adhesion and invasion by the parasite and have named it as Fasciclin Related Adhesive Protein or FRAP.

Materials and Methods

Sequence analysis and identification of FRAP orthologs: Sequences for *P. falciparum* (Accession # AAN37059), *P. berghei* (Accession # CAH94515) and *P. chaubaudi* (Accession # CAH77280) FRAP were obtained from GenBank, where they have been deposited as part of the parasite genome sequencing projects (8, 24) Using *P. falciparum* FRAP sequence, orthologs were identified from unannotated genome sequences of *P. gallinaceum*, *P. reichenowi*, *P. vivax*, *P. yoelii* and *P. knowlesi* parasites, available at PlasmoDB, Sanger Center and TIGR web sites (25). FRAP orthologs from *Theileria parva* (Accession # EAN32245) and *T annulata* (Accession # CAI76887) were from the published genome sequence (26, 27). The nucleic acid sequences of the genes are provided in FIG. 2A-J. The amino acid sequences were aligned using Clustal W algorithm (28) for multiple sequence alignment, using the DNASTAR package. The amino acid sequences are depicted in FIG. 1, and the alignment is given in FIG. 3.

Reverse Transcription, Amplification and Cloning of FRAP proteins: Total RNA was obtained from highly purified preparations of *P. falciparum* (3D7 strain) sporozoites (29). 2 µg of total RNA was reverse transcribed and amplified with the forward 5'CACCATGAAAAATAGATTTTAT-TATAATTTG 3' (SEQ ID NO: 22) and reverse 5'AAAAAT-GATGGGCTTATCTACTATATG 3' (SEQ ID NO: 23) primers, using Promega Access RT-PCR kit. The amplified fragment was cloned in pET101-TOPO (Invitrogen) an *E. coli* expression vector containing a C-terminal [His]$_6$ tag, giving rise to plasmid pFRAP. The forward primers encoded a tetra nucleotide CACC, which facilitated the directional cloning of amplified fragments in the expression vector. The authenticity of the clone was verified by DNA sequencing. Two other FRAP constructs, encoding amino acids 1-87 and 88-205 were generated by PCR-based subcloning using pFRAP as template, giving rise to plasmid pFRAP2 and pFRAP3 respectively. Authenticity of these constructs was verified by DNA sequencing. Sequencing was performed at the core laboratory sequencing facility of the Virginia Bioinformatics Institute.

Expression, localization and purification of recombinantly expressed FRAP protein: For protein expression, *E. coli* BL21cells were transformed with a desired plasmid, grown in super broth, and at the $OD_{600}$=1.0, expression was induced with IPTG, at a final concentration of 1 mM. Three hours post-induction, the culture was harvested by centrifugation at 3000 g for 10 minutes. To identify the intracellular site of accumulation of the protein, pellet was resuspended in 20% sucrose solution in mM Tris pH 7.5 and incubated on ice for 10 min. Cells were spun at 5000 g for 20 min and the pellet was resuspended in chilled water for 10 minutes. This was followed by centrifugation at 8000 g for minutes to isolate periplasmic fluid. Spheroplast pellet was further processed to isolate inclusion bodies, as previously described (30). Inclusion bodies were solubilized in 50 mM CAPS buffer containing 0.3% N-lauryl lauryl sarkosine and 0.3 M NaCl, pH 11.0 for 30 min and centrifuged at 10000 g for 30 min at room temperature. The supernatant was loaded onto a His-Trap High Performance affinity column (GE Health Care) and bound protein was eluted using an imidazole gradient in 50 mM CAPS pH 11.0 containing 0.3% N-lauryl sarkosine and 0.3 M NaCl. Relevant fractions were pooled and purified to homogeneity by gel filtration chromatography on Superdex 200 10/300 GL column (GE Health Care). Authenticity of the purified protein was verified by amino terminal sequencing and western blotting using anti-polyhistidine tag monoclonal antibody. For obtaining recombinant CS protein, pCS27IVC a plasmid with a polyhistidine tag at the carboxyl terminus (1) was expressed in BL21 *E. coli* cells and the protein was purified from the periplasm as previously described (31).

Generation of anti-FRAP2 antibodies: The protocol for antibody generation was approved by the animal care committee at Virginia Tech. 6-8 weeks old female CD1 mice were subcutaneously immunized with 10 μg of purified FRAP2 emulsified in complete Freunds adjuvant. Two subsequent booster doses in incomplete Freunds adjuvant were administered on days 21 and 35, after the first immunization. Sera were collected two weeks after the last booster. Antibodies were purified on a Protein G affinity column using AKTA FPLC chromatography system.

Confocal analysis: Purified P. falciparum sporozoites were air dried on a glass slide. The slide was blocked with 5% normal goat serum in phosphate buffer saline (PBS). Subsequently, the slide was incubated with doubling dilutions (1:20 to 1:20480) of anti-FRAP2 or pre immune mouse serum and incubated at room temperature, in a humidified chamber, for one hour. Unbound antibodies were removed by washing the slide with TBS containing 0.05% Tween 20 followed by the addition of an anti-mouse FITC conjugate (1:500 dilution). Confocal imaging was performed using BioRad Radiance confocal microscope.

Immunoelectron microscopy: Preparations of Plasmodium falciparum-infected salivary glands were fixed in 4% paraformaldehyde (Electron Microscopy Sciences, PA) in 0.25 M HEPES (pH 7.4) for 1 hr at room temperature, then in 8% paraformaldehyde in the same buffer overnight at 4° C. They were infiltrated, frozen and sectioned as previously described (32). The sections were immunolabeled with mouse anti-FRAP antibodies (1:1000 in PBS/1% fish skin gelatin), then with anti-mouse IgG antibodies, followed directly by 10 nm protein A-gold particles (Department of Cell Biology, Medical School, Utrecht University, the Netherlands) before examination with a Philips CM120 Electron Microscope (Eindhoven, the Netherlands) under 80 kV.

Liver Cell binding assay: The binding of proteins was assayed on HepG2 cells as described previously (1, 31). Briefly, cells were plated at a density of 25,000 cells/well, in a 96 well plate, 36 hours before the start of the experiment. The cells were fixed with paraformaldehyde, blocked with 1% BSA, followed by the addition of equimolar concentrations of recombinant proteins. Bound protein was detected using anti-polyhistidine tag monoclonal antibody (1:10,000) and anti-mouse antibody conjugated to alkaline phosphatase (1:2000). Amount of bound protein was detected by using 4-methylumbelliferyl phosphate, a fluorescent substrate, and measurement of fluorescence using a fluorescent plate reader (Molecular Devices, CA) with excitation and emission set at 350 nm and 460 nm respectively. Results are shown as mean±standard deviation of mean of a representative experiment performed in triplicate. Binding inhibition assays were performed by combining the recombinant proteins with increasing amounts of glycosaminoglycans and incubating at 37° C. for 15 min. For enzyme treatment, cells were incubated with different concentrations of Heparinase I or Chondroitinase ABC for 90 minutes at 37° C. as previously described (31), before the addition of proteins. The bound protein was assayed as described above.

All the proteins used in the binding assay possessed a polyhistidine tag at their carboxyl terminus. Therefore, binding activity was probed using a polyhistidine tag monoclonal antibody. This excluded the possibility of misinterpretation of the data due to differences in antibody affinities.

Sporozoite Invasion Assay: Invasion assay was performed with HepG2 (Human hepatoma) cells as previously described (31). Briefly, HepG2 cells were plated (50,000 cells/0.3 ml) and incubated overnight at 37° C. in a $CO_2$ incubator. Next day, medium was removed and 50 μl of diluted FRAP proteins (final concentrations: 20 and 10 μg/ml) or anti-FRAP2 antibodies (40 μg/ml final concentration) were added per well. Anti CS monoclonal antibody NFS1 was used at a final concentration of 100 μg/ml. All protein concentrations and serum dilutions were evaluated in triplicate. This was immediately followed by the addition of 20,000 sporozoites in 50 μl of medium to each well. P. falciparum (strain NF54) sporozoites were obtained from the salivary glands of An. stephensi mosquitoes as described by Ozaki (33). The sporozoites were allowed to invade liver cells for three hours followed by the washing of cells with PBS at pH 7.4. Subsequently, the cells were fixed with cold methanol. Sporozoites were visualized by immunostaining using NFS1 as primary antibody and anti-mouse IgG-peroxidase conjugate. The slides were mounted with Paramount and only intracellular sporozoites were counted as described (31). Percentage inhibition of invasion was calculated with the following formula:

[(Control-test)/control]×100

Results

Identification and sequence analysis of FRAP: Analysis of the published DNA sequence of chromosome 14 of P. falciparum (8) identified a 824 nucleotide sequence (Accession # NP702335) containing a hypothetical, single copy, three-exon gene, encoding a 205 amino acids long protein (FIG. 1, SEQ ID NO: 1). Bioinformatical analysis of the predicted protein using the NCBI conserved domain database (CDD) search tool (34), revealed that the protein encodes a Fasciclin (FAS1) domain (SMART accession no. SM00554) from amino acids 88-204 with an e-value of 2e-10. FIG. 1 depicts the FRAP protein sequence and its alignment with the consensus sequence of FAS1 domain in the database. FAS1 domains are known for their huge sequence diversity and typically have 20% sequence identity in a pairwise alignment (23). They are recognized by only two short semi-conserved sequence motifs (underlined in FIG. 3). A similar pattern is seen in FRAP as its FAS1 domain has 21% sequence identity with the consensus sequence.

Using published, unpublished and unannotated sequences in the databases for pathogens at Sanger, PlasmoDB and TIGR web sites, P. falciparum FRAP orthologs were identified in all Plasmodial species that have been sequenced till date or are currently undergoing sequencing (FIG. 1). Orthologs of P. falciparum FRAP were found in avian (P. gallinaceum), rodent (P. berghei, P. yoelii and P. chaubaudi) simian (P. knowlesi and P. reichenowi) and human (P. vivax) malaria parasites suggesting that the FRAP protein is most likely present in all the members of Plasmodium genus and, hence, could be playing an important role in the biology of the parasite. Within the Plasmodium genus, the protein maintains a 60% sequence identity (FIG. 3) with 124 out of 205 residues being identical. Beyond Plasmodium, FRAP homologs were only found in the two recently sequenced Theileria genomes (26, 27) with an overall sequence identity of 29% (FIG. 3). In contrast, FRAP homologs could not be found in the recently sequenced Leishmania (35) and Trypanosome genomes (36). This selective presence in Plasmodium and Theileria genomes could point towards a common function of the protein between otherwise two very different parasites.

The amino acid sequences for the FRAP proteins discussed above are depicted in FIG. 1, the nucleic acid sequences that encode the proteins are depicted in FIG. 2, and the corresponding SEQ ID NOS: are given in Table 3.

TABLE 3

SEQ ID NOS: for amino acid and nucleic acid

| | SEQ ID NO: | |
|---|---|---|
| Organism | Amino acid sequence | Nucleic acid sequence |
| P. falciparum | SEQ ID NO: 1 | SEQ ID NO: 2 |
| P. gallinaceum | SEQ ID NO: 3 | SEQ ID NO: 4 |
| P. reichenowi | SEQ ID NO: 5 | SEQ ID NO: 6 |
| P. vivax | SEQ ID NO: 7 | SEQ ID NO: 8 |
| P. yoelii | SEQ ID NO: 9 | SEQ ID NO: 10 |
| P. knowlesi | SEQ ID NO: 11 | SEQ ID NO: 12 |
| P. chaubaudi | SEQ ID NO: 13 | SEQ ID NO: 14 |
| P. berghei | SEQ ID NO: 15 | SEQ ID NO: 16 |
| T. parva | SEQ ID NO: 17 | SEQ ID NO: 18 |
| T. annulata | SEQ ID NO: 19 | SEQ ID NO: 20 |

Figure 4B:
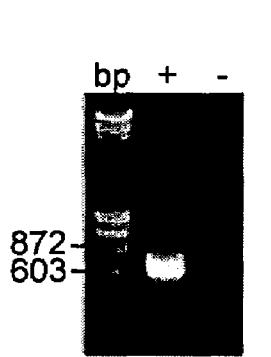

Cloning of P. falciparum FRAP: Coding sequence of P. falciparum FRAP was amplified by RT-PCR using total RNA from the sporozoite stage of the parasite, giving rise to a 615 bp fragment. This PCR product was not due to the presence of contaminating genomic DNA in the RNA preparation, as a parallel reaction performed in the absence of reverse transcriptase enzyme, showed no amplification. Also, the size of the amplified fragment, viz. 615 bp, matched the size of the predicted mature mRNA (FIG. 4b). The amplified fragment from the sporozoite stage was cloned in a T7 promoter-based E. coli expression vector, giving rise to plasmid pFRAP. Sequencing of the cloned DNA fragment authenticated the predicted exon structure and coding sequence for the FRAP protein (data not shown). To investigate the role of FAS1 domain in the biology of the protein, two more plasmid constructs viz., pFRAP2 and pFRAP3, were generated by sub-cloning, using pFRAP as template. pFRAP2 encoded the DNA sequence for amino acids 1-87 of the full length protein while pFRAP3 encoded the FAS1 domain represented by amino acids 88-205 (FIG. 4a). The authenticity of these clones was also verified by sequencing.

Figure 4C:
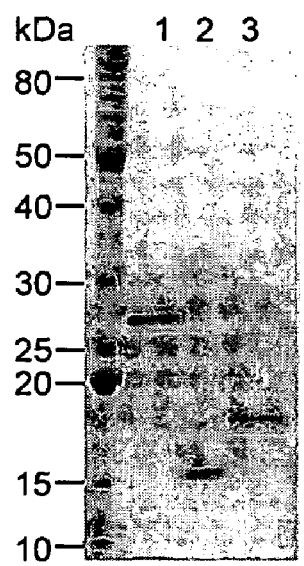
Figure 4D:
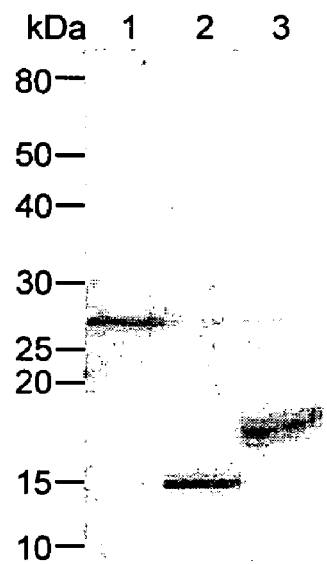

Recombinant Expression and Purification of FRAP proteins: To obtain recombinant FRAP proteins, the desired construct was transformed in E. coli BL21 cells and the expression was induced with IPTG. Three hours post induction, the culture was harvested and the site of accumulation of the recombinant protein was evaluated by sub-cellular fractionation. For all three FRAP proteins, the expression was localized in the spheroplast in the form of insoluble inclusion bodies (data not shown). Spheroplast pellet was further processed to isolate inclusion bodies, as previously described (30). Inclusion bodies were solubilized and the proteins were purified by a combination of affinity and gel filtration chromatography. The presence of a polyhistidine tag at the carboxyl terminus of the recombinantly expressed proteins facilitated the purification and all three proteins were initially purified on a His-Trap affinity column (data not shown). The proteins at this stage were 95% pure. Further purification to apparent homogeneity was done by gel filtration chromatography (FIG. 4c). Purified FRAP, FRAP2 and FRAP3 had the expected molecular weights of 27.8, 12.3 and 17.7 kDa respectively and were recognized by a monoclonal antibody directed against the polyhistidine tag present at the carboxyl terminus of all the proteins (FIG. 4d). The first 15 residues of each of the proteins were also verified by amino terminal sequencing (data not shown). Together, these results authenticated the recombinant proteins and suggested that they were structurally intact.

FRAP is localized in the micronemes of the sporozoites: To detect the expression of FRAP on sporozoites, protein-specific antibodies were raised by immunizing mice with FRAP2 protein. Anti-FRAP2 antibodies readily recognized the expression of FRAP protein on the sporozoite (not shown). The binding was specific as pre-immune serum did not recognize any expression on the sporozoites. This indicated that transcription of FRAP mRNA can be correlated to its expression during the sporozoite stage of the lifecycle. Immunoelectron microscopy using anti-FRAP2 antibodies revealed that FRAP was localized in the lumen of micronemes, a specialized secretory organelle in the cytoplasm (not shown). The protein was present in the apical micronemes, suggesting that it could be secreted during the infectivity process. In Plasmodium, micronemes contain several adhesive domain-containing proteins that are associated with host cell adhesion and invasion at both, sporozoite and erythrocytic stages of its lifecycle (13, 37, 38). This suggested that FRAP could be playing a role in the infectivity process.

Figure 5:
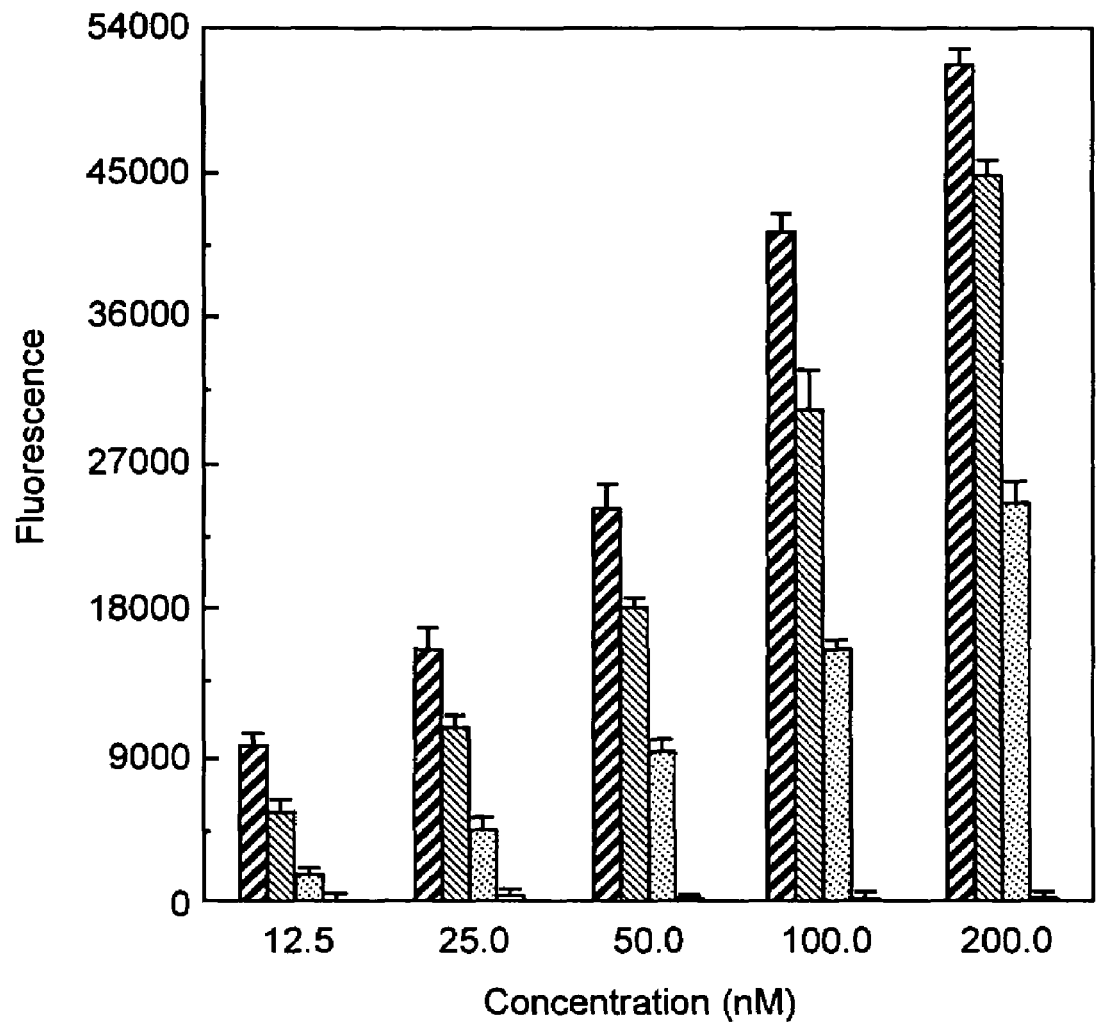
FIG. 5. Binding analysis of FRAP proteins on HepG2 cells. Five different concentrations of recombinant proteins were investigated for their potential to bind to liver cells. Bound protein was detected using anti-polyhistidine monoclonal followed by the addition of anti-mouse alkaline phosphatase conjugate and a fluorescent substrate. Fluorescence was measured using a plate reader with excitation at 350 nm and emission at 460 nm. Black bars: CS protein; Hashed bars: FRAP; Grey bars: FRAP2; White bars: FRAP3.

FRAP is involved in adhesion of sporozoites to liver cells: FRAP was investigated for its possible role in host cell adhesion using a human hepatocyte cell line, HepG2, an established model for investigating sporozoite-liver cell interactions in malaria (1, 31). FRAP showed a dose dependent binding on liver cells (FIG. 5) which was comparable to the binding activity of CS protein, a known parasite protein involved in the adhesion and invasion of liver cells by the sporozoites (1). This suggested that FRAP could be serving as one of the parasite ligands in host-parasite interactions. This host-cell binding activity of FRAP was not due to the presence of the FAS1 domain alone, as FRAP3, a protein encoding only the FAS1 domain (amino acids 88-205) did not bind to liver cells, even at the highest concentration used in the assay (54). Although FAS1 domain alone did not show any binding, its deletion from the full length protein (protein FRAP2) lead to a 50% loss of activity, in comparison to the full length protein (FIG. 5). This suggested that both, FAS1 domain and the amino terminus region, contribute to the binding activity of the protein and an intact FRAP is required for its optimal activity.

FRAP binds liver cells through heparan sulfate proteoglycans: As FRAP showed potent liver cell binding, the nature of its receptor on liver cells was investigated by utilizing glycosaminoglycans as competitive inhibitors. Inhibition of adherence by the addition of soluble glycosaminoglycans in an assay may suggest that the involved host receptor is a proteoglycan (31, 39). In the presence of free heparin, binding activity of FRAP and FRAP2 was reduced by 55 and 60% respectively (FIG. 6). In contrast, chondroitin sulfate A showed no inhibition at the highest concentration evaluated in the assay (FIG. 6). This suggested that FRAP utilizes heparan sulfate-based proteoglycans (HSPG) as a receptor for adhesion.

The involvement of HSPG as a receptor was further verified by evaluating the binding of the protein on liver cells that were pretreated with specific glycosaminoglycan-cleaving enzymes. Cells were pre-treated with heparinase I or chondroitinase ABC followed by the evaluation of binding activity of FRAP and FRAP2. Heparinase I selectively removes heparan sulfate while chondroitinase ABC cleaves chondroitin sulfate A, B and C type sugars from the liver cell surface. Both, FRAP and FRAP2 lost 50% of their binding activity on heparinase I treated cells (Table 4) confirming the involvement of a heparin-based receptor on the liver cell surface. CS protein, which binds hepatocytes through HSPG (39) also showed a similar decrease in binding activity. In contrast, treatment of liver cells with chondroitinase ABC resulted in no loss of activity.

TABLE 4

Binding of FRAP proteins to hepatocytes is inhibited by pretreatment of cells with glycosaminoglycan cleaving enzyme. Cells were pretreated with different concentrations of either Heparinase I or Chondroitinase ABC for 90 minutes followed by the addition of 100 nM of protein. Inhibition of binding was calculated by comparing the binding of respective proteins on non-treated HepG2 cells in the same plate.

|  | Inhibition of Binding (%) | | |
| --- | --- | --- | --- |
| Enzyme, U/ml | FRAP | FRAP2 | CSP |
| Heparinase I | | | |
| 1.25 | 39.4 ± 4.2 | 42.3 ± 10.4 | 48.1 ± 12.0 |
| 2.50 | 42.1 ± 7.6 | 41.4 ± 1.5 | 57.7 ± 7.9 |
| 5.00 | 47.8 ± 1.4 | 49.4 ± 9.2 | 59.1 ± 6.5 |
| Chondroitinase ABC | | | |
| 0.01 | — | — | — |
| 0.12 | — | — | — |
| 1.25 | — | — | — |

FRAP is involved in liver cell invasion: As FRAP proteins efficiently bound to HepG2 cells, we investigated the ability of the two proteins and the anti-FRAP2 antibodies in preventing invasion of human liver cells by *P. falciparum* sporozoites in culture. Both FRAP and FRAP2 could prevent sporozoites from invading liver cells by 89.5% and 92.4% respectively, at the highest concentration of the protein used in the assay. This activity was comparable to the invasion inhibition activity of CSP protein, which at a similar concentration could also inhibit the invasion by 92.6%. Anti-FRAP2 antibodies showed extreme potency as at a concentration of 40 µg/ml, it inhibited sporozoite invasion by 94.6%, a level comparable to the inhibitory activity of anti-CS monoclonal antibody NFS1 (Table 5). This indicated that (i) FRAP not only plays a role in binding, it is also involved in the invasion process (ii) the protein utilizes its amino terminus (amino acids 1-87) for its invasion activity and (iii) a potent antibody response against FRAP2 by the host may play a role in malaria control.

TABLE 5

FRAP is involved in invasion of liver cells by *P. falciparum* sporozoites. Invasion of HepG2 cells by *P. falciparum* sporozoites was evaluated in the presence of different concentrations of free proteins or anti-FRAP2 antibodies and compared with the invasion activity in the presence of culture medium. % inhibition represents the decrease in the number of sporozoites that invaded liver cells in comparison to the invasion level in cells incubated with culture medium.

| Treatment | Concentration µg/ml | % Inhibition |
| --- | --- | --- |
| Culture Medium | — | — |
| FRAP | 20 | 89.5 + 1.0 |
|  | 10 | 80.9 + 1.0 |
| FRAP2 | 20 | 92.4 + 3.5 |
|  | 10 | 88.1 + 4.6 |
| CS Protein | 20 | 92.6 + 2.0 |
| Anti-FRAP2 antibody | 40 | 94.6 + 1.2 |
| Anti-CS monoclonal | 100 | 97.4 + 0.7 |

Discussion

Deciphering the mechanism of infectivity of the malaria parasite is a major prerequisite for developing intervention strategies. Key to this process is the unique set of proteins, many of them currently unknown, expressed by the parasite to bind and invade host cells. Therefore, a combination of biochemical and functional studies of malarial genes is required to identify parasitic proteins involved in pathogenesis.

We identified *P. falciparum* FRAP, a new parasite protein and showed that it is expressed during the sporozoite stage of the lifecycle. Orthologs of *P. falciparum* FRAP were identified in rodent, avian, simian and human malaria species and multiple sequence alignment revealed that the protein has 60% sequence identity within the *Plasmodium* genus (FIG. 3). Its universal presence and conserved nature suggested that the protein plays an important role in the biology of the parasite.

The protein was localized in the sporozoite micronemes by immunoelectron microscopy. Micronemes are specialized secretory organelles in *Plasmodium* and during the sporozoite stage secrete a wide variety of proteins involved in parasite motility, traversal and host cell infection. Previously, TRAP/SSP2 and SPECT, two sporozoite proteins with adhesive Thrombospondin type I repeat (TSR) domains have been found in the micronemes and have subsequently been shown to be involved in the infectivity process (13, 37). As FRAP encoded FAS1, an ancient adhesive domain present in both prokaryotes and eukaryotes, we therefore investigated the role of FRAP in host cell adhesion and invasion by the sporozoites.

The protein was recombinantly expressed in *E. coli* and purified to homogeneity by column chromatography (FIG. 4c). The purified protein showed robust and dose dependent binding to liver cells indicating that it is involved in the attachment of sporozoites to liver cells (FIG. 5). This activity was comparable to the binding activity of CS protein, considered to be the primary binding ligand, suggesting that FRAP could be one of the primary parasite proteins involved in attachment of sporozoites to liver cells. In βig-h3, a FAS1 domain-containing human protein involved in corneal cell adhesion, the adhesion activities of the protein completely resides in the FAS1 domain (22). To investigate the role of FAS1 domain in FRAP, we expressed FAS1 domain alone (amino acids 88-205, protein FRAP3) and evaluated its cell binding activity on HepG2 cells. The protein did not show any cell binding activity (FIG. 5), indicating that the deleted segment (amino acids 1-87) of the protein plays an important role in the binding activity of the protein.

This was investigated by expressing amino acids 1-87 (protein FRAP2) in *E. coli* and evaluation of its cell binding activities on the liver cell line. FRAP2 was capable of binding to liver cells, albeit at only half the strength of its full length protein, FRAP. This suggested that amino terminus region of the protein plays an important role in the host cell binding, however, an intact FRAP molecule is required for its optimal activity. The loss of activity seen here could be due to loss of the required tertiary conformation of the binding domain (due to the absence of the FAS1 domain) and/or part of the binding motif is present in the FAS1 domain of the protein. A similar situation exists in the case of CS protein, where the unique amino terminus region plays an important role in liver cell binding and invasion activities of the protein (31).

FRAP exploited heparan sulfate proteoglycans, expressed on liver cell surface, as receptor for its biological activities (Table 4). This was revealed by competition studies with defined carbohydrates, as well as loss of binding upon enzymatic removal of host glycans. Heparan sulfate-protein interactions involve positively charged residues of the protein, which interact with the negatively charged carboxylate and sulfate ions of the glycosaminoglycan chain. The amino terminus of FRAP possesses a disproportionate number of positively charged residues (13 out of the first 50) some of which are extremely conserved within the *Plasmodium* genus (FIG. 3). Their conserved nature suggests that they could possibly be involved in these interactions. Parallels exist for such mechanism in other heparin-binding proteins where a large number of positively charged residues involved in heparin/HS interaction are present in a close proximity in the protein (40).

Entry of sporozoites into the hepatocyte is a multistep process, where the initial attachment to the hepatocytes is followed by the invasion of liver cells, by the parasite. To investigate the role of FRAP in the invasion process, recombinant FRAP proteins and anti-FRAP2 antibodies were used as competitors in an in vitro invasion assay. Proteins FRAP, FRAP2 and anti-FRAP2 antibodies inhibited the invasion of liver cells by *P. falciparum* sporozoites with extreme competence, showing as high as 94.6 % inhibition (Table 5) in the assay. These levels were comparable to the inhibitory activity of CSP protein and anti-CSP monoclonal antibody. These results indicated that FRAP is utilized by sporozoites for both adhesion and subsequent invasion of liver cells and the amino terminal region plays an important role in these processes. It is noteworthy that similar level (>90%) of inhibition has only been possible by targeting CSP, SSP2/TRAP and the recently discovered SPATR protein (10). Recently, AMA1 has been shown to be involved in liver cell invasion but antibodies against the protein could inhibit the invasion only by about 50% (41). CSP and SSP2/TRAP are being vigorously pursued as vaccine candidates and are currently being evaluated in the clinic (4, 5). Involvement of FRAP in liver cell invasion and its strong inhibition by antibodies suggest that a potent immunological response against this protein in vivo could serve as a strategy for intervention and the immunological competence of FRAP as a vaccine candidate needs to be investigated.

Although we have investigated the role of FRAP in the liver cell adhesion and invasion by the sporozoites, it is noteworthy that microarray and proteomic studies have revealed that FRAP is also transcribed and expressed during the erythrocytic stages of the lifecycle, especially during the schizonts, which is immediately followed by the release of merozoites and invasion of red blood cells (9, 42, 43). AMA1 and MAEBL, two micronemal proteins that are expressed at sporozoites and erythrocytic stages of the lifecycle, are involved in pathogenesis, both, at pre-erythrocytic and blood stages, where they play a role in host cell adhesion and invasion (41, 44-46). With its multistage expression, it is possible that FRAP could also be involved in host-parasite interactions during erythrocytic stages of the lifecycle.

In conclusion, we have identified and characterized a new parasite protein involved in malaria pathogenesis at the sporozoite stage of the lifecycle. It's involvement in pathogenesis indicates that developing intervention strategies targeting FRAP creates new treatment options for controlling malaria.

REFERENCES FOR EXAMPLE 1

1. Cerami, C., Frevert, U., Sinnis, P., Takacs, B., Clavijo, P., Santos, M. J. & Nussenzweig, V. (1992) *Cell* 70, 1021-33.
2. Robson, K. J., Frevert, U., Reckmann, I., Cowan, G., Beier, J., Scragg, I. G., Takehara, K., Bishop, D. H., Pradel, G., Sinden, R. & et al. (1995) *Embo J* 14, 3883-94.
3. Wang, R., Doolan, D. L., Le, T. P., Hedstrom, R. C., Coonan, K. M., Charoenvit, Y., Jones, T. R., Hobart, P., Margalith, M., Ng, J., Weiss, W. R., Sedegah, M., de Taisne, C., Norman, J. A. & Hoffman, S. L. (1998) *Science* 282, 476-80.
4. Alonso, P. L., Sacarlal, J., Aponte, J. J., Leach, A., Macete, E., Milman, J., Mandomando, I., Spiessens, B., Guinovart, C., Espasa, M., Bassat, Q., Aide, P., Ofori-Anyinam, O., Navia, M. M., Corachan, S., Ceuppens, M., Dubois, M. C., Demoitie, M. A., Dubovsky, F., Menendez, C., Tomieporth, N., Ballou, W. R., Thompson, R. & Cohen, J. (2004) *Lancet* 364, 1411-20.
5. Moorthy, V. S., Imoukhuede, E. B., Keating, S., Pinder, M., Webster, D., Skinner, M. A., Gilbert, S. C., Walraven, G. & Hill, A. V. (2004) *J Infect Dis* 189, 2213-9.
6. Nardin, E. H., Calvo-Calle, J. M., Oliveira, G. A., Nussenzweig, R. S., Schneider, M., Tiercy, J. M., Loutan, L., Hochstrasser, D. & Rose, K. (2001) *J Immunol* 166, 481-9.
7. Hoffmran, S. (1996) *Malaria Vaccine Development: A multi immune response approach* (ASM press, Washington, D.C.).
8. Gardner, M. J., Hall, N., Fung, E., White, O., Berriman, M., Hyman, R. W., Carlton, J. M., Pain, A., Nelson, K. E., Bowman, S., Paulsen, I. T., James, K., Eisen, J. A., Rutherford, K., Salzberg, S. L., Craig, A., Kyes, S., Chan, M. S., Nene, V., Shallom, S. J., Suh, B., Peterson, J., Angiuoli, S., Pertea, M., Allen, J., Selengut, J., Haft, D., Mather, M. W., Vaidya, A. B., Martin, D. M., Fairlamb, A. H., Fraunholz, M. J., Roos, D. S., Ralph, S. A., McFadden, G. I., Cummings, L. M., Subramanian, G. M., Mungall, C., Venter, J. C., Carucci, D. J., Hoffinan, S. L., Newbold, C., Davis, R. W., Fraser, C. M. & Barrell, B. (2002) *Nature* 419, 498-511.
9. Florens, L., Washburn, M. P., Raine, J. D., Anthony, R. M., Grainger, M., Haynes, J. D., Moch, J. K., Muster, N., Sacci, J. B., Tabb, D. L., Witney, A. A., Wolters, D., Wu, Y., Gardner, M. J., Holder, A. A., Sinden, R. E., Yates, J. R. & Carucci, D. J. (2002) *Nature* 419, 520-6.
10. Chattopadhyay, R., Rathore, D., Fujioka, H., Kumar, S., De La Vega, P., Haynes, D., Moch, K., Fryauff, D., Wang, R., Carucci, D. J. & Hoffmnan, S. L. (2003) *J Biol Chem* 278, 25977-25981.
11. Bateman, A., Coin, L., Durbin, R., Finn, R. D., Hollich, V., Griffiths-Jones, S., Khanna, A., Marshall, M., Moxon, S., Sonnhammer, E. L., Studholme, D. J., Yeats, C. & Eddy, S. R. (2004) *Nucleic Acids Res* 32, D138-41.
12. Letunic, I., Copley, R. R., Schmidt, S., Ciccarelli, F. D., Doerks, T., Schultz, J., Ponting, C. P. & Bork, P. (2004) *Nucleic Acids Res* 32, DI 42-4.
13. Ishino, T., Yano, K., Chinzei, Y. & Yuda, M. (2004) *PLoS Biol* 2, E4.
14. Bastiani, M. J., Harrelson, A. L., Snow, P. M. & Goodman, C. S. (1987) *Cell* 48, 745-55.
15. Terasaka, K., Yamaguchi, R., Matsuo, K., Yamazaki, A., Nagai, S. & Yamada, T. (1989) *FEMS Microbiol Lett* 49, 273-6.
16. Snow, P. M., Zinn, K., Harrelson, A. L., McAllister, L., Schilling, J., Bastiani, M. J., Makk, G. & Goodman, C. S. (1988) *Proc Natl Acad Sci USA* 85, 5291-5.
17. Johnson, K. L., Jones, B. J., Bacic, A. & Schultz, C. J. (2003) Plant Physiol 133, 1911-25.
18. Wang, W. C., Zinn, K. & Bjorkman, P. J. (1993) *J Biol Chem* 268, 1448-55.
19. Hu, S., Sonnenfeld, M., Stahl, S. & Crews, S. T. (1998) *J Neurobiol* 35, 77-93.
20. Zinn, K., McAllister, L. & Goodman, C. S. (1988) *Cell* 53, 577-87.

21. Politz, O., Gratchev, A., McCourt, P. A., Schledzewski, K., Guillot, P., Johansson, S., Svineng, G., Franke, P., Kannicht, C., Kzhyshkowska, J., Longati, P., Velten, F. W. & Goerdt, S. (2002) *Biochem J* 362, 155-64.
22. Kim, J. E., Kim, S. J., Lee, B. H., Park, R. W., Kim, K. S. & Kim, I. S. (2000) *J Biol Chem* 275, 30907-15.
23. Clout, N. J., Tisi, D. & Hohenester, E. (2003) *Structure (Camb)* 11, 197-203.
24. Hall, N., Karras, M., Raine, J. D., Carlton, J. M., Kooij, T. W., Berriman, M., Florens, L., Janssen, C. S., Pain, A., Christophides, G. K., James, K., Rutherford, K., Harris, B., Harris, D., Churcher, C., Quail, M. A., Ormond, D., Doggett, J., Trueman, H. E., Mendoza, J., Bidwell, S. L., Rajandream, M. A., Carucci, D. J., Yates, J. R., 3rd, Kafatos, F. C., Janse, C. J., Barrell, B., Turner, C. M., Waters, A. P. & Sinden, R. E. (2005) *Science* 307, 82-6.
25. Bahl, A., Brunk, B., Coppel, R. L., Crabtree, J., Diskin, S. J., Fraunholz, M. J., Grant, G. R., Gupta, D., Huestis, R. L., Kissinger, J. C., Labo, P., Li, L., McWeeney, S. K., Milgram, A. J., Roos, D. S., Schug, J. & Stoeckert, C. J., Jr. (2002) *Nucleic Acids Res* 30, 87-90.
26. Gardner, M. J., Bishop, R., Shah, T., de Villiers, E. P., Carlton, J. M., Hall, N., Ren, Q., Paulsen, I. T., Pain, A., Berriman, M., Wilson, R. J., Sato, S., Ralph, S. A., Mann, D. J., Xiong, Z., Shallom, S. J., Weidman, J., Jiang, L., Lynn, J., Weaver, B., Shoaibi, A., Domingo, A. R., Wasawo, D., Crabtree, J., Wortman, J. R., Haas, B., Angiuoli, S. V., Creasy, T. H., Lu, C., Suh, B., Silva, J. C., Utterback, T. R., Feldblyum, T. V., Pertea, M., Allen, J., Nierman, W. C., Taracha, E. L., Salzberg, S. L., White, 0. R., Fitzhugh, H. A., Morzaria, S., Venter, J. C., Fraser, C. M. & Nene, V. (2005) *Science* 309, 134-7.
27. Pain, A., Renauld, H., Berriman, M., Murphy, L., Yeats, C. A., Weir, W., Kerhornou, A., Aslett, M., Bishop, R., Bouchier, C., Cochet, M., Coulson, R. M., Cronin, A., de Villiers, E. P., Fraser, A., Fosker, N., Gardner, M., Goble, A., Griffiths-Jones, S., Harris, D. E., Katzer, F., Larke, N., Lord, A., Maser, P., McKellar, S., Mooney, P., Morton, F., Nene, V., O'Neil, S., Price, C., Quail, M. A., Rabbinowitsch, E., Rawlings, N. D., Rutter, S., Saunders, D., Seeger, K., Shah, T., Squares, R., Squares, S., Tivey, A., Walker, A. R., Woodward, J., Dobbelaere, D. A., Langsley, G., Rajandream, M. A., McKeever, D., Shiels, B., Tait, A., Barrell, B. & Hall, N. (2005) *Science* 309, 131-3.
28. Thompson, J. D., Higgins, D. G. & Gibson, T. J. (1994) *Nucleic Acids Res* 22, 4673-80.
29. Haynes, J. D. & Moch, J. K. (2002) *Methods Mol Med* 72, 489-97.
30. Rathore, D., Hrstka, S. C., Sacci, J. B., Jr., De la Vega, P., Linhardt, R. J., Kumar, S. & McCutchan, T. F. (2003) *J Biol Chem* 278, 40905-10.
31. Rathore, D., Sacci, J. B., de la Vega, P. & McCutchan, T. F. (2002) *J Biol Chem* 277, 7092-8.
32. Folsch, H., Pypaert, M., Schu, P. & Mellman, I. (2001) *J Cell Biol* 152, 595-606.
33. Ozaki, L. S., Gwadz, R. W. & Godson, G. N. (1984) *J Parasitol* 70, 831-3.
34. Marchler-Bauer, A. & Bryant, S. H. (2004) *Nucleic Acids Res* 32, W327-31.
35. Ivens, A. C., Peacock, C. S., Worthey, E. A., Murphy, L., Aggarwal, G., Berriman, M., Sisk, E., Rajandream, M. A., Adlem, E., Aert, R., Anupama, A., Apostolou, Z., Attipoe, P., Bason, N., Bauser, C., Beck, A., Beverley, S. M., Bianchettin, G., Borzym, K., Bothe, G., Bruschi, C. V., Collins, M., Cadag, E., Ciarloni, L., Clayton, C., Coulson, R. M., Cronin, A., Cruz, A. K., Davies, R. M., De Gaudenzi, J., Dobson, D. E., Duesterhoeft, A., Fazelina, G., Fosker, N., Frasch, A. C., Fraser, A., Fuchs, M., Gabel, C., Goble, A., Goffeau, A., Harris, D., Hertz-Fowler, C., Hilbert, H., Horn, D., Huang, Y., Klages, S., Knights, A., Kube, M., Larke, N., Litvin, L., Lord, A., Louie, T., Marra, M., Masuy, D., Matthews, K., Michaeli, S., Mottram, J. C., Muller-Auer, S., Munden, H., Nelson, S., Norbertczak, H., Oliver, K., O'Neil, S., Pentony, M., Pohl, T. M., Price, C., Pumelle, B., Quail, M. A., Rabbinowitsch, E., Reinhardt, R., Rieger, M., Rinta, J., Robben, J., Robertson, L., Ruiz, J. C., Rutter, S., Saunders, D., Schafer, M., Schein, J., Schwartz, D. C., Seeger, K., Seyler, A., Sharp, S., Shin, H., Sivam, D., Squares, R., Squares, S., Tosato, V., Vogt, C., Volckaert, G., Wambutt, R., Warren, T., Wedler, H., Woodward, J., Zhou, S., Zimmermann, W., Smith, D. F., Blackwell, J. M., Stuart, K. D., Barrell, B., et al. (2005) *Science* 309, 436-42.
36. Berriman, M., Ghedin, E., Hertz-Fowler, C., Blandin, G., Renauld, H., Bartholomeu, D. C., Lennard, N. J., Caler, E., Hamlin, N. E., Haas, B., Bohme, U., Hannick, L., Aslett, M. A., Shallom, J., Marcello, L., Hou, L., Wickstead, B., Alsmark, U. C., Arrowsmith, C., Atkin, R. J., Barron, A. J., Bringaud, F., Brooks, K., Carrington, M., Cherevach, I., Chillingworth, T. J., Churcher, C., Clark, L. N., Corton, C. H., Cronin, A., Davies, R. M., Doggett, J., Djikeng, A., Feldblyum, T., Field, M. C., Fraser, A., Goodhead, I., Hance, Z., Harper, D., Harris, B. R., Hauser, H., Hostetler, J., Ivens, A., Jagels, K., Johnson, D., Johnson, J., Jones, K., Kerhomou, A. X., Koo, H., Larke, N., Landfear, S., Larkin, C., Leech, V., Line, A., Lord, A., Macleod, A., Mooney, P. J., Moule, S., Martin, D. M., Morgan, G. W., Mungall, K., Norbertczak, H., Ormond, D., Pai, G., Peacock, C. S., Peterson, J., Quail, M. A., Rabbinowitsch, E., Rajandream, M. A., Reitter, C., Salzberg, S. L., Sanders, M., Schobel, S., Sharp, S., Simmonds, M., Simpson, A. J., Tallon, L., Turner, C. M., Tait, A., Tivey, A. R., Van Aken, S., Walker, D., Wanless, D., Wang, S., White, B., White, O., Whitehead, S., Woodward, J., Wortman, J., Adams, M. D., Embley, T. M., Gull, K., Ullu, E., Barry, J. D., Fairlamb, A. H., Opperdoes, F., Barrell, B. G., Donelson, J. E., Hall, N., Fraser, C. M., et al. (2005) *Science* 309, 416-22.
37. Muller, H. M., Reckmiam, I., Hollingdale, M. R., Bujard, H., Robson, K. J. & Crisanti, A. (1993) *Embo J* 12, 2881-9.
38. Sim, B. K., Chitnis, C. E., Wasniowska, K., Hadley, T. J. & Miller, L. H. (1994) *Science* 264, 1941-4.
39. Frevert, U., Sinnis, P., Cerami, C., Shreffler, W., Takacs, B. & Nussenzweig, V. (1993) *J Exp Med* 177, 1287-98.
40. Hileman, R. E., Fromm, J. R., Weiler, J. M. & Linhardt, R. J. (1998) *Bioessays* 20, 156-67.
41. Silvie, O., Franetich, J. F., Charrin, S., Mueller, M. S., Siau, A., Bodescot, M., Rubinstein, E., Hannoun, L., Charoenvit, Y., Kocken, C. H., Thomas, A. W., Van Gemert, G. J., Sauerwein, R. W., Blackman, M. J., Anders, R. F., Pluschke, G. & Mazier, D. (2004) *J Biol Chem* 279, 9490-6.
42. Bozdech, Z., Zhu, J., Joachimiak, M. P., Cohen, F. E., Pulliam, B. & DeRisi, J. L. (2003) *Genome Biol* 4, R9.
43. Bozdech, Z., Llinas, M., Pulliam, B. L., Wong, E. D., Zhu, J. & DeRisi, J. L. (2003) *PLoS Biol* 1, E5.
44. Preiser, P., Renia, L., Singh, N., Balu, B., Jarra, W., Voza, T., Kaneko, O., Blair, P., Torii, M., Landau, I. & Adams, J. H. (2004) *Infect Immun* 72, 3604-8.

45. Kappe, S. H., Noe, A. R., Fraser, T. S., Blair, P. L. & Adams, J. H. (1998) *Proc Natl Acad Sci USA* 95, 1230-5.
46. Mitchell, G. H., Thomas, A. W., Margos, G., Dluzewski, A. R. & Bannister, L. H. (2004) *Infect Immun* 72, 154-8.

Example 2

Inhibitory Epitope in FRAP

Identification of inhibitory epitope by peptide mapping As we have demonstrated that antibodies against FRAP2, an 87 amino acid polypeptide can prevent invasion, the region of the protein responsible for this recognition was mapped by developing a set of overlapping peptides that were utilized for ELISA. A set of 10 overlapping peptides (Table 6) were chemically synthesized and used as coating antigen to identify the epitope recognized by these antibodies. Overlapping Peptides HAI-3,4, & 5 were predominantly recognized by these antibodies, suggesting that a 32 amino acid sequence (TRSGGLRKPQKVTNDPESINRKVYWCFEHKPV, SEQ ID NO: 24), comprised by these peptides is being recognized by the inhibitory antibodies (Table 7). A sequence comparison of these peptides reveals that an 8 amino acid sequence (TNDPESIN, SEQ ID NO: 37) is present in all of them (FIG. 7) suggesting that this sequence could be an important component of the region recognized by the anti-protein antibodies. Therefore, the 32 amino acid sequence or portion thereof can be exploited as part of a multi-epitope subunit vaccine. The 32 amino acid region has 100% sequence homology or 87.5% sequence identity within the *Plasmodium* genus implying that this region plays a critical role in all the *Plasmodium* species and an immune response(s) generated against this region of the protein in one species could be a factual representation of immune responses against other species, generated by its host. Two other peptides (HAI-7 and HAI- 10) were also recognized by the anti-protein antibodies suggesting that their recognition is also important in preventing parasites from initiating an infection.

TABLE 6

Sequence of peptides chemically synthesized for identification of inhibitory epitope.

| Peptide | Sequence | SEQ ID NO |
|---|---|---|
| HAI-1 | MKNRFYYNLIIKRLYTRSGG | SEQ ID NO: 27 |
| HAI-2 | NLIIKRLYTRSGGLRKPQKV | SEQ ID NO: 28 |
| HAI-3 | TRSGGLRKPQKVTNDPESIN | SEQ ID NO: 29 |
| HAI-4 | GLRKPQKVTNDPESINRKVY | SEQ ID NO: 30 |
| HAI-5 | TNDPESINRKVYWCFEHKPV | SEQ ID NO: 31 |
| HAI-6 | VYWCFEHKPVKRTIINLIYS | SEQ ID NO: 32 |
| HAI-7 | KPVKRTIINLIYSHNELKIF | SEQ ID NO: 33 |
| HAI-8 | NLIYSHNELKIFSNLLNHPT | SEQ ID NO: 34 |
| HAI-9 | NELKIFSNLLNHPTVGSSLI | SEQ ID NO: 35 |
| HAI-10 | NLLNHPTVGSSLIHELSLDG | SEQ ID NO: 36 |

TABLE 7

Recognition of FRAP-derived peptides by ELISA. Peptides were coated onto the ELISA plate followed by the addition of log dilutions of antibodies followed by anti-mouse antibodies conjugated to alkaline phosphatase. Recognition was measured at 405 nm using an ELISA plate reader.

| Peptide/ | 1:100 | | 1:1000 | | 1:10K | |
|---|---|---|---|---|---|---|
| Antigen | FRAP | FRAP2 | FRAP | FRAP2 | FRAP | FRAP2 |
| HAI-1 | 0.010 | 0.015 | — | — | — | — |
| HAI-2 | 0.010 | 0.020 | — | — | — | — |
| HAI-3 | 0.710 | 0.530 | 0.223 | 0.190 | 0.026 | 0.020 |
| HAI-4 | 0.789 | 0.710 | 0.4445 | 0.630 | 0.063 | 0.230 |
| HAI-5 | 0.660 | 0.636 | 0.290 | 0.465 | 0.030 | 0.110 |
| HAI-6 | 0.005 | — | — | — | — | — |
| HAI-7 | 0.730 | 0.065 | 0.550 | 0.026 | 0.165 | — |
| HAI-8 | 0.020 | 0.290 | — | 0.039 | — | — |
| HAI-9 | 0.030 | — | — | — | — | — |
| HAI-10 | 0.250 | 0.300 | 0.030 | 0.045 | — | — |
| FRAP* | 0.670 | 0.600 | 0.650 | 0.465 | 0.340 | 0.130 |
| FRAP** | 0.210 | 0.260 | 0.070 | 0.400 | — | 0.190 |

*4 pmol of protein
**2 nmol of each peptide in 50 ul coating buffer

Optimal recognition of an epitope by the host immune system requires that the epitope maintains its structural conformation. While short amino acid sequences can be easily recognized in vitro, their recognition under in-vivo conditions almost always requires them to be present as part of a much larger polypeptide. This is especially important for configurational epitopes present in the surface antigens of malaria parasite whose recognition requires that a continuous stretch of amino acids, larger than its identified epitope, be present for its optimal recognition. Therefore, a 32 amino acid long region is most likely required for optimal recognition of FRAP protein by the host immune system and it could be utilized either alone or in combination with other known and unknown malarial antigens in a vaccine.

FRAP is recognized by the host immune system of malaria-infected subjects. Sera from 17 malaria infected subjects was screened for the presence of anti-FRAP antibodies, by ELISA. 0.5 microgram of purified FRAP protein was coated as antigen and its recognition was probed with sera at 1:200 dilution. 4 sera samples from north American volunteers, who have never been exposed to malaria were used as control. A cutoff value of OD405=0.378, which represented mean of OD+2 SD was used to determine samples that were positive. The ELISA results indicated that 10 out of 17 (58.8%) infected subjects had anti-FRAP antibodies (Table 8) with OD values above the set cutoff.

TABLE 8

Recognition of full length FRAP by sera from infected subjects living in Bandiagara, a malaria-endemic district in Mali.

| Sample ID | Absorbance, 405 nm | Positive |
|---|---|---|
| 1A-001 | 0.79 ± 0.07 | Y |
| 1A-002 | 1.03 ± 0.05 | Y |
| 1A-004 | 0.47 ± 0.02 | Y |
| 1A-005 | 0.23 ± 0.01 | N |
| 1A-007 | 0.23 ± 0.01 | N |
| 1A-008 | 0.49 ± 0.07 | Y |
| 1A-010 | 0.26 ± 0.01 | N |
| 1A-011 | 0.21 ± 0.01 | N |
| 1A-013 | 0.91 ± 0.00 | Y |
| 1A-014 | 0.30 ± 0.01 | N |
| 1A-016 | 0.60 ± 0.01 | Y |
| 1A-017 | 0.15 ± 0.01 | N |
| 1A-019 | 0.43 ± 0.00 | Y |

TABLE 8-continued

Recognition of full length FRAP by sera from infected subjects living in Bandiagara, a malaria-endemic district in Mali.

| Sample ID | Absorbance, 405 nm | Positive |
|---|---|---|
| 1A-020 | 0.56 ± 0.01 | Y |
| 1A-021 | 0.40 ± 0.00 | Y |
| 1A-023 | 0.41 ± 0.02 | Y |
| 1A-024 | 0.20 ± 0.00 | N |

Example 3

FRAP is a Malaria Drug Target

Once a malaria parasite infects red blood cells, host hemoglobin serves as its primary source of amino acids required for its geometric increase in infection. It achieves its goal by cannibalizing hemoglobin to its constituent amino acids, which it recycles for its own protein synthesis. While the parasite is extremely effective in digesting the protein (globin) component of hemoglobin the heme prosthetic group serves as a challenge to its survivability. Free heme released from hemoglobin is lethal for the parasite and to escape its deleterious effects the parasite enzymatically polymerizes heme into a non-toxic byproduct known as hemozoin. Therefore, any mechanism by which polymerization of heme into nontoxic hemozoin can be inhibited will lead to a very effective therapeutic for malaria.

Figure 8:
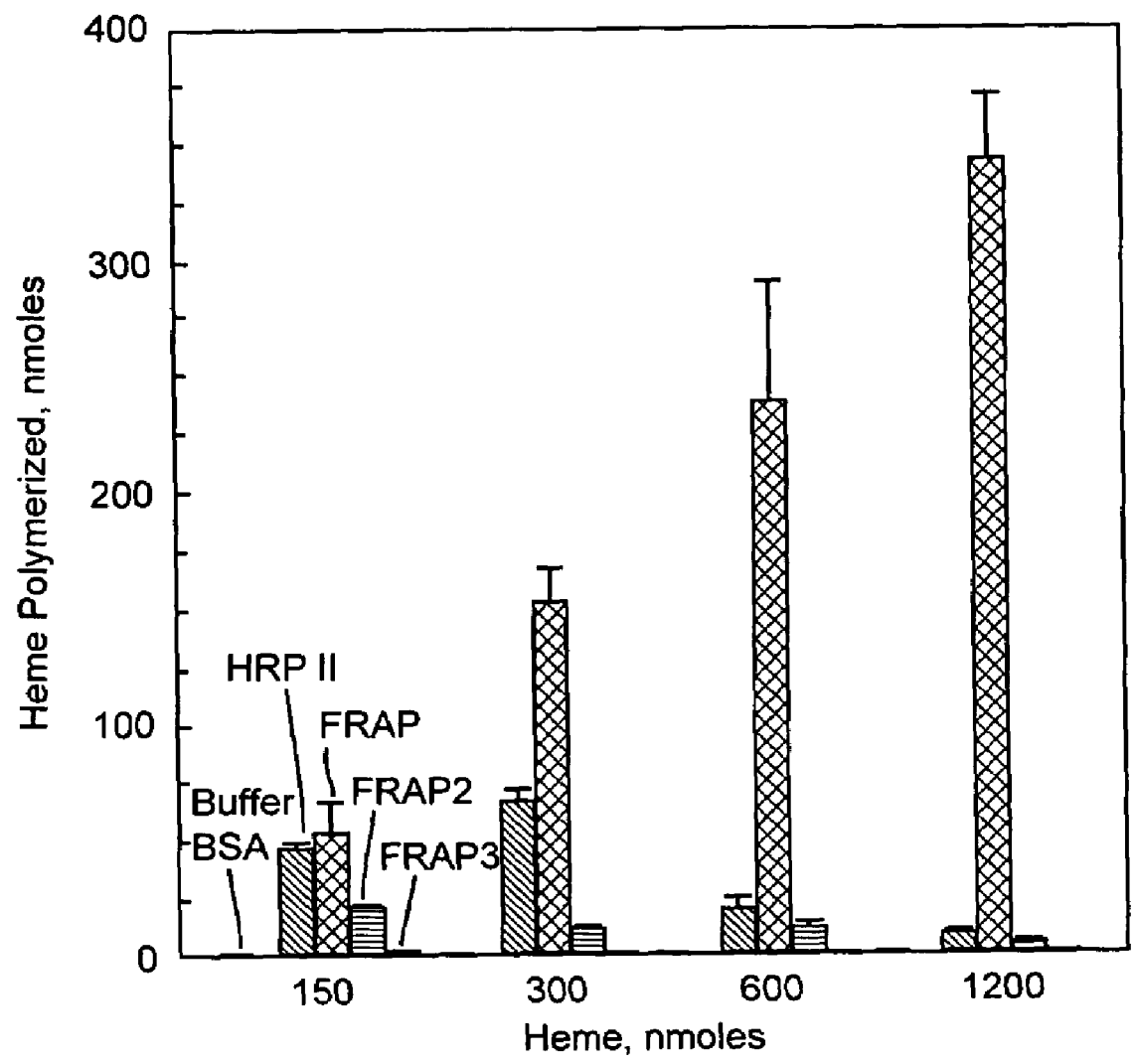
FIG. 8. FRAP-mediated neutralization of toxic heme into non-toxic Hemozoin. 500 pmoles of each of the protein was incubated with different concentrations of free heme at 37° C. for 16 hours, under acidic conditions (500 mM Sodium acetate pH 5.2). After 16 hours, free heme was removed by washing and the insoluble pellet representing hemozoin was solubalized in sodium hydroxide and estimated using a spectrophotometer. FRAP showed 10-20 fold more activity in comparison to HRPII, indicating that it could be the major protein responsible for polymerization of heme in the parasite.
Figure 9:
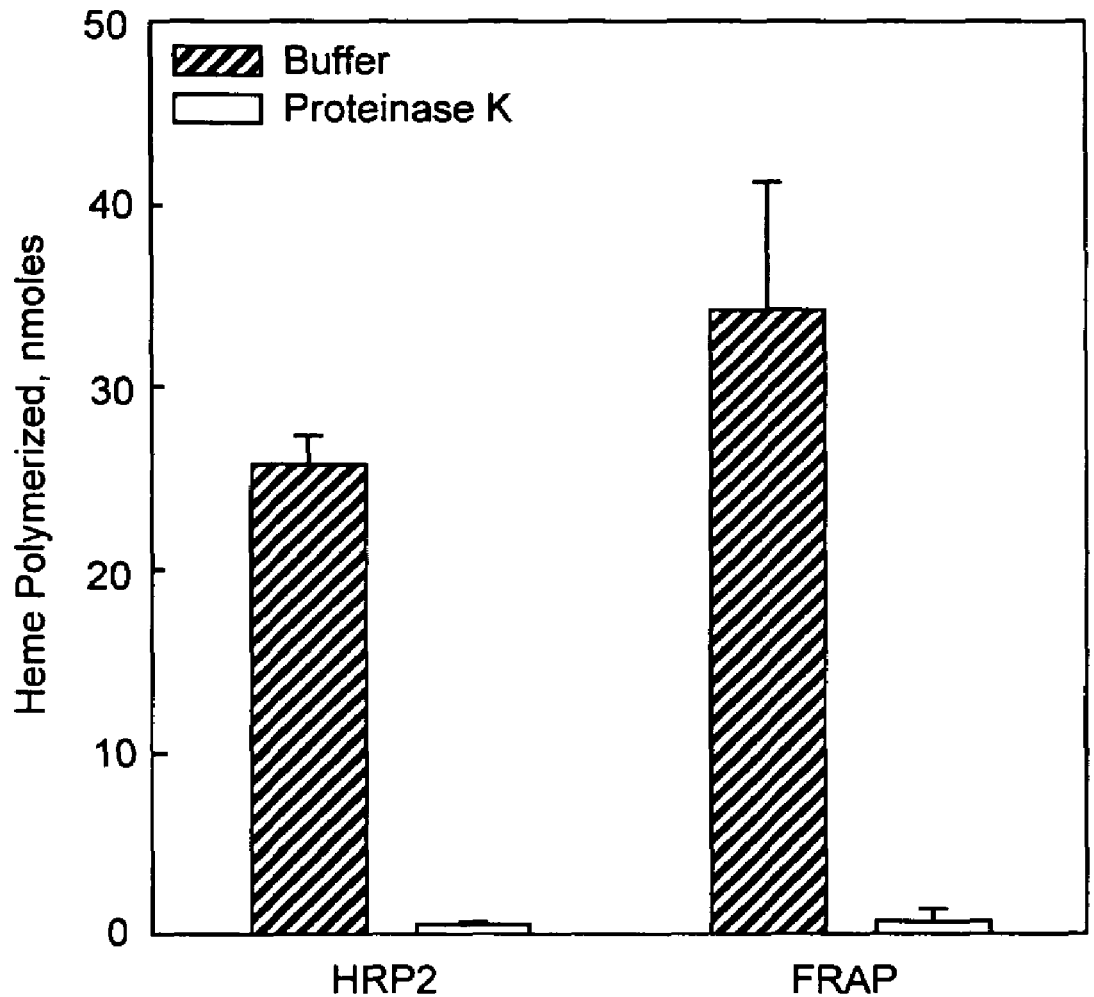
FIG. 9. FRAP-mediated hemozoin formation requires intact protein. Hemozoin formation was investigated with FRAP pretreated with proteinase K, a nonspecific protease or with buffer alone. Incubation of FRAP with Proteinase K led to a complete loss of activity suggesting that the conversion of heme into hemozoin requires intact FRAP protein.

We show here that FRAP is responsible for this activity. FRAP effectively converted toxic heme into inactive hemozoin in a dose dependent manner (FIG. 8). The hemozoin formation activity was 10-20-fold higher in comparison to histidine rich protein II, the only known parasite protein capable of making hemozoin. This activity was specific as it was lost when the protein was pre-treated with proteinase K (a non specific protease) suggesting that an intact protein is required for this activity (FIG. 9). The activity requires the complete protein as two truncated variants of FRAP (FRAP2 and FRAP3) did not show any hemozoin formation (FIG. 8).

Figure 10:
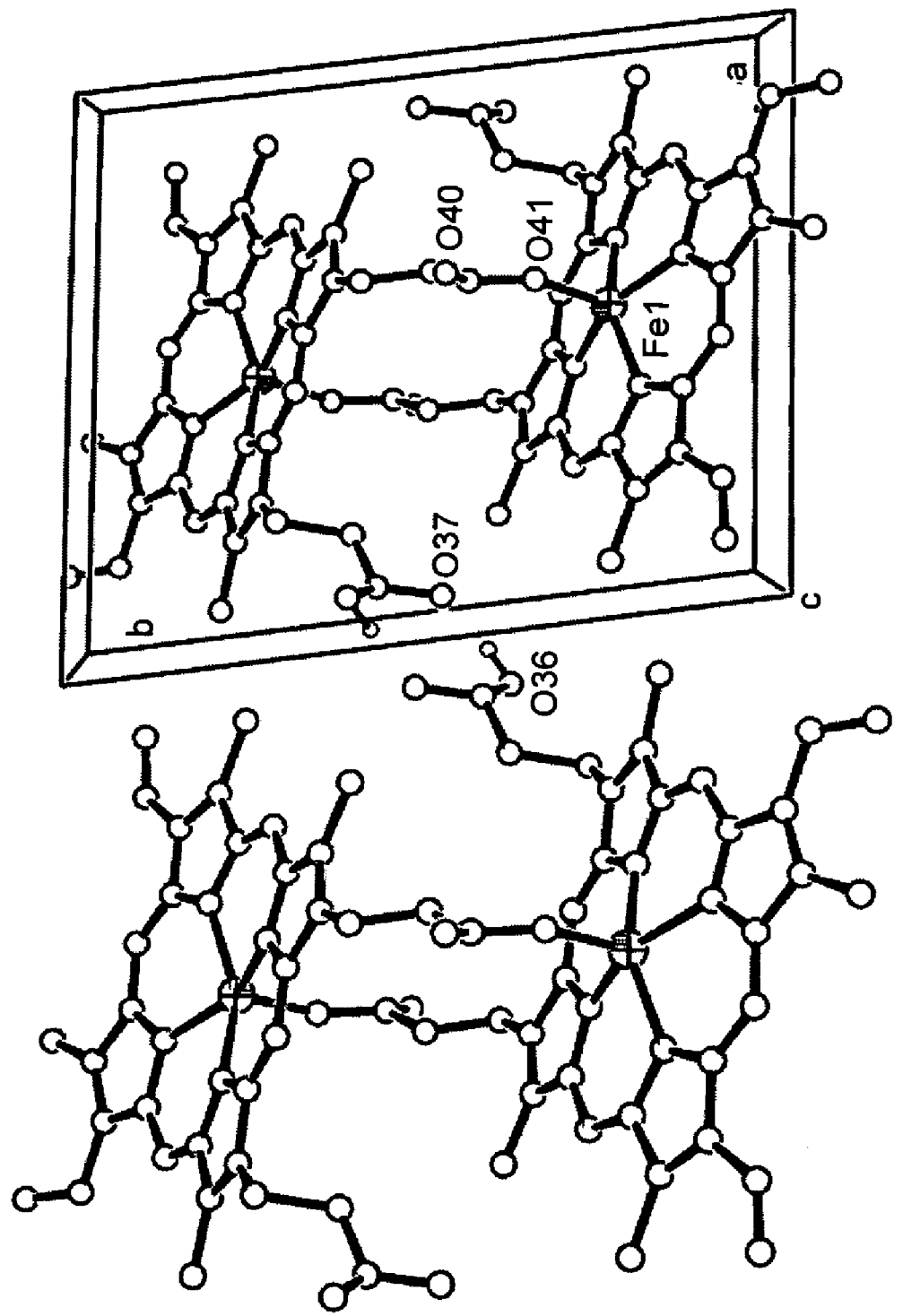
FIG. 10. Chemical structure of hemozoin. Dimerization of heme through a Fe1-O41 linkage leads to the formation of β-hematin. Oxygen mediated non-covalent interaction between β-hematin units leads to the stacking and the polymerized product is known as hemozoin. Adapted from (Pagola et al., 2000)
Figure 11:
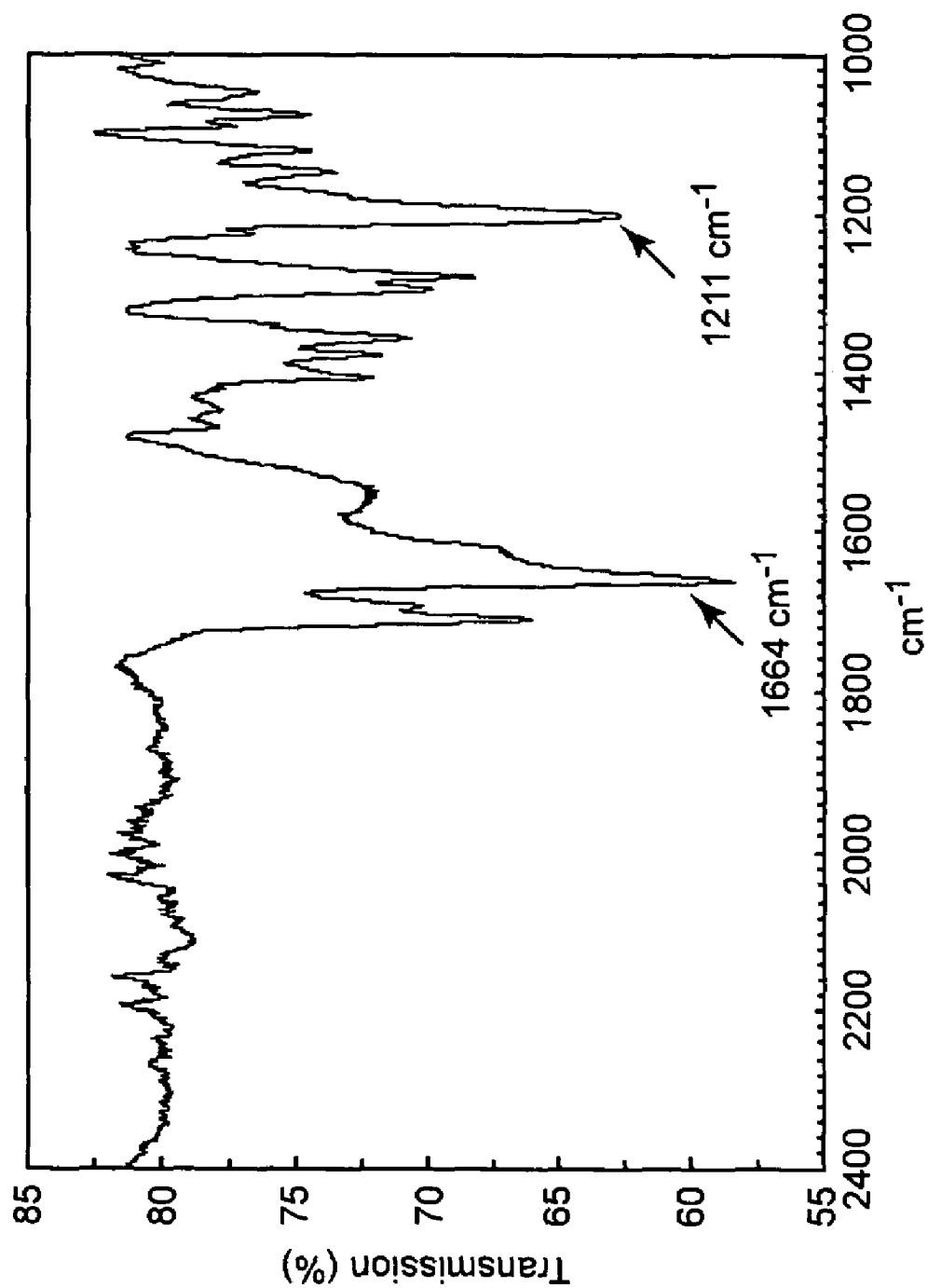
FIG. 11. Spectroscopic verification of FRAP-mediated polymerized heme as hemozoin. Heme polymerized into hemozoin was subjected to Fourier transform-Infra Red (FT-IR) spectroscopy to verify its chemical nature. The insoluble product showed a dramatic decrease in transmittance at 1664 and 1211 cm$^{-1}$, a well established spectroscopic signature of β-hematin.

The authenticity of the polymerized heme as hemozoin was verified by FT-IR spectroscopy. The IR spectra of hemozoin contains an intense absorbance at 1664 and 1211 $cm^{-1}$, that are absent in the spectra of free heme (Slater et al., 1991). These are characteristics of a carboxylate group coordinated to the iron center of ferriporphyrin (Fe01-O41) arising from stretching of the localized carbon-oxygen double and single bonds, respectively (Slater et al., 1991). The chemical structure of β-hematin is depicted in FIG. 10 (adapted from (Pagola et al., 2000)). The infra red spectra of the FRAP-generated product showed the characteristic decrease in transmittance at 1664 and 1211 $cm^{-1}$, chemically validating that the product formed was indeed hemozoin (FIG. 11).

FRAP residues involved in heme polymerization were identified by generating 11 variants of FRAP by site-directed mutagenesis. Evaluation of these mutants for heme polymerization-activity revealed that three residues viz., F42, H44 & H122 are critically involved in hemozoin formation, as their conversion to alanine lead to a complete loss of activity (Table 9).

FRAP protein shows remarkably high amount of sequence homology between different *Plasmodium* species. In FRAP, a highly conserved protein sequence has biological relevance as the residues shown to be involved in hemozoin formation viz., F42, H44, H122 (Table 9) are not only conserved within the *Plasmodium* genus, they are also conserved in *Theileria* parasites. This indicates that FRAP protein from a non-human malaria parasite can be used as target for screening and development of novel inhibitors for FRAP protein of human malaria parasite.

This can be achieved by screening a library of small molecules/inhibitors in vitro in the FRAP-mediated hemozoin formation assay, which will lead to the identification of a candidate molecule(s). These molecules can be subsequently evaluated in an in vitro *P. falciparum* culture in the laboratory. Once their efficacy has been proved in vitro, these molecules can be evaluated in a rodent malaria parasite model. This will be feasible due to the extremely conserved nature of the protein and the amino acids residues of FRAP involved in the process of hemozoin formation (F42, H44, H122), as seen by site-directed mutagenesis, being identical between all known FRAP proteins (Table 9, FIG. 3).

Once a small molecule shows efficacy in the mouse malaria model, it can be directly evaluated in a monkey model without requiring extensive experimentation as FRAP in *P. knowlesi*, the monkey malaria parasite, has the same residues in its active site. Therefore, it is possible to develop FRAP inhibitors for human malaria parasite by targeting FRAP sequence from other species of *Plasmodium*.

TABLE 9

Identification of FRAP residues involved in Hemozoin formation. 11 FRAP residues were individually mutated to alanine by site-directed mutagenesis; proteins were expressed in *E. coli* and purified to homogeneity. Polymerization of heme was investigated with 500 pmoles of each of the proteins and their activity was compared with the unmutated FRAP. Conversion of F42, H44 and H122 lead to a complete loss of activity, suggesting a critical role for these residues in the polymerase activity of the protein.

| Protein | Heme Polymerized (nmoles) | % Decrease |
|---|---|---|
| FRAP | 139.2 | — |
| Y39A | 155.2 | — |
| F42A | 0.6 | 99.5 |
| H44A | 6.7 | 95.1 |
| F64A | 102.2 | 26.6 |
| H79A | 133.5 | 4.1 |
| F90A | 111.1 | 20.1 |
| H122A | 0.9 | 99.3 |
| C191A | 104.9 | 24.6 |
| H192A | 115.6 | 16.9 |
| H197A | 106.4 | 23.5 |

Figure 12:
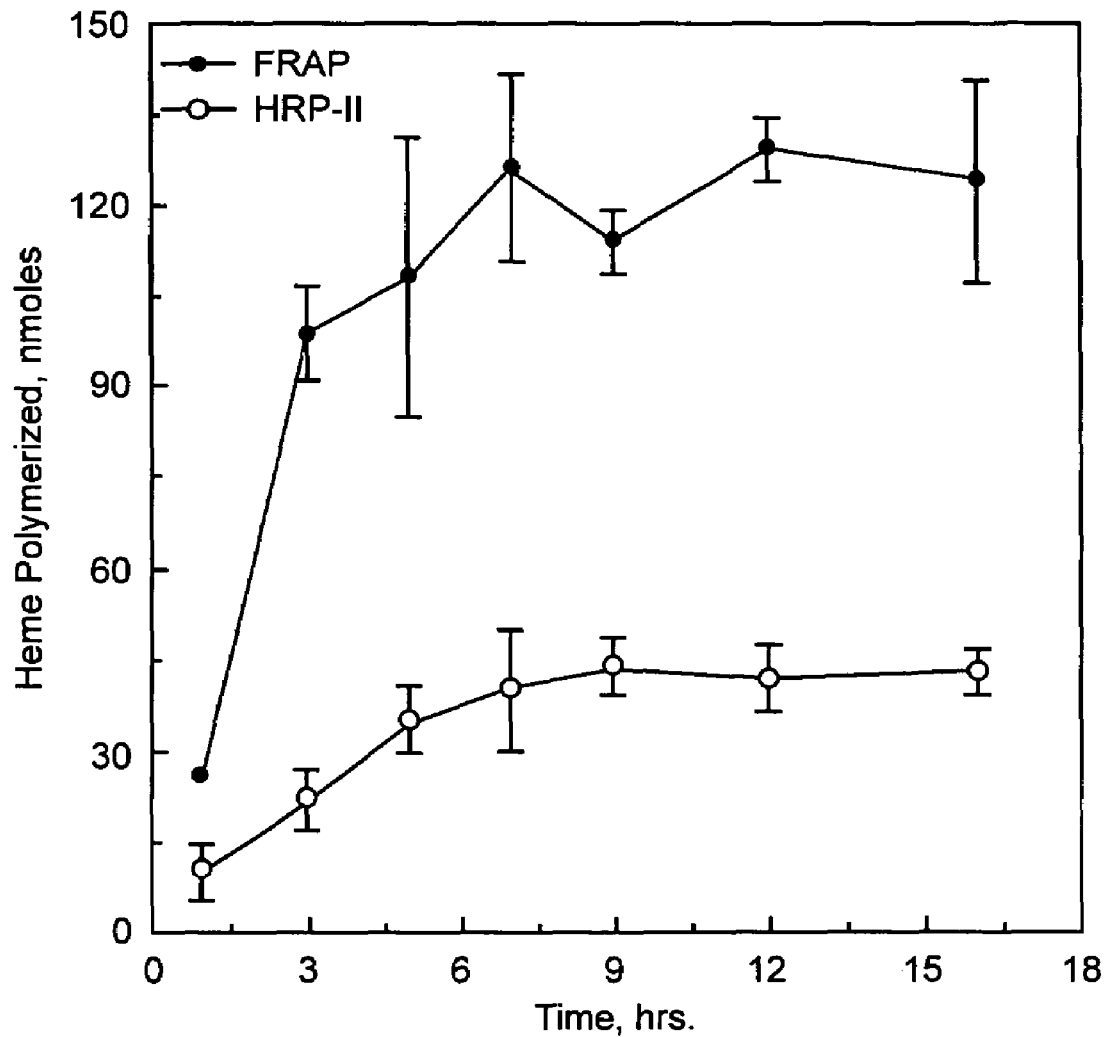
FIG. 12. Time Kinetics of hemozoin formation. FRAP-mediated hemozoin formation was investigated with respect to time. 500 pmoles of protein was incubated with 300 nmoles of heme for different times and the amount of heme polymerized was measured as previously described. Hemozoin formation was found to be essentially complete by 5 hours.
Figure 13:
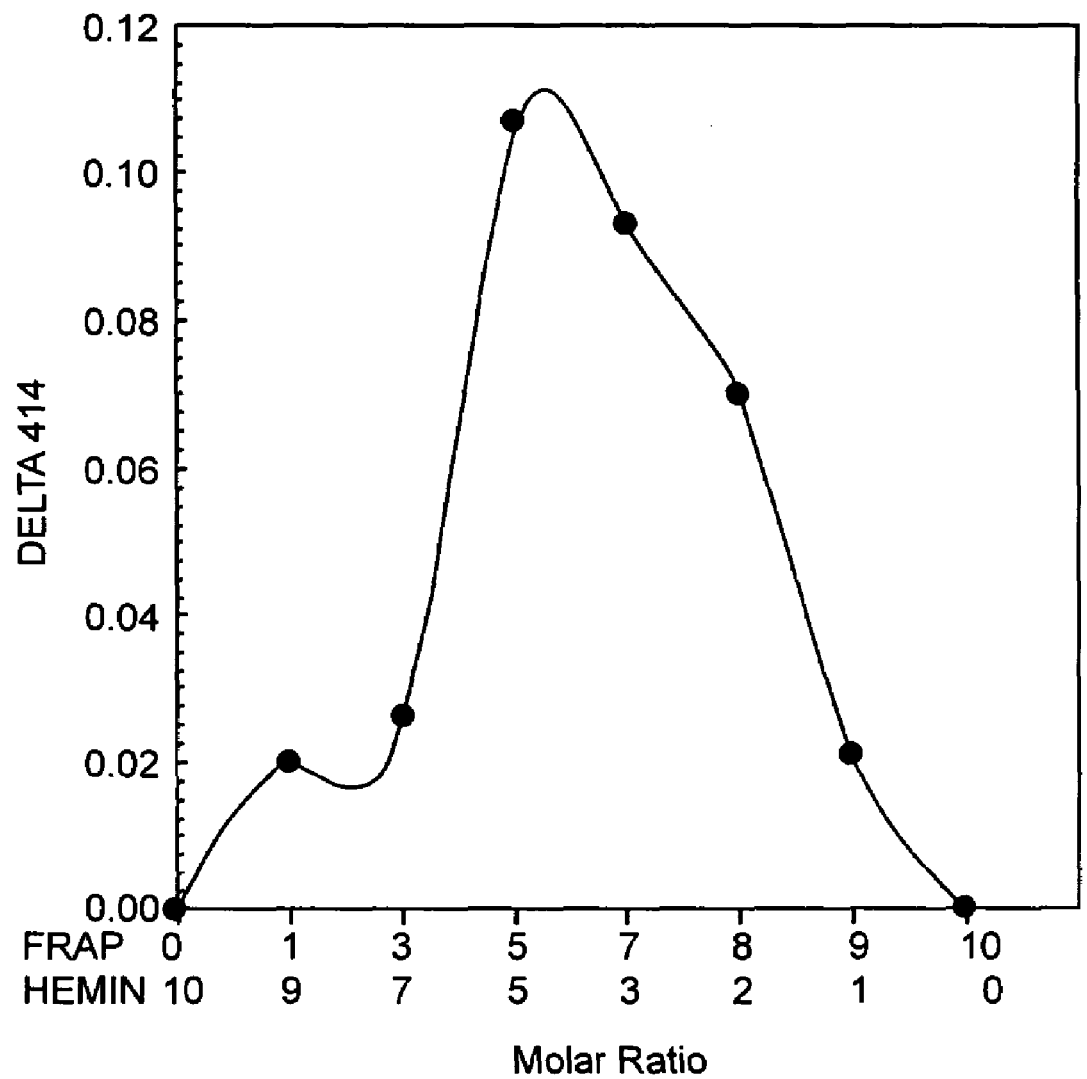
FIG. 13. Stoichiometry of FRAP-Heme Interaction. Stoichiometry of the FRAP-Heme interaction was determined spectrophotometrically by continuous variation method (Job Plot). Change in absorbance was measured by using different molar ratios of FRAP-heme complex. FRAP-Heme have a 1:1 stoichiometry.
Figure 14:
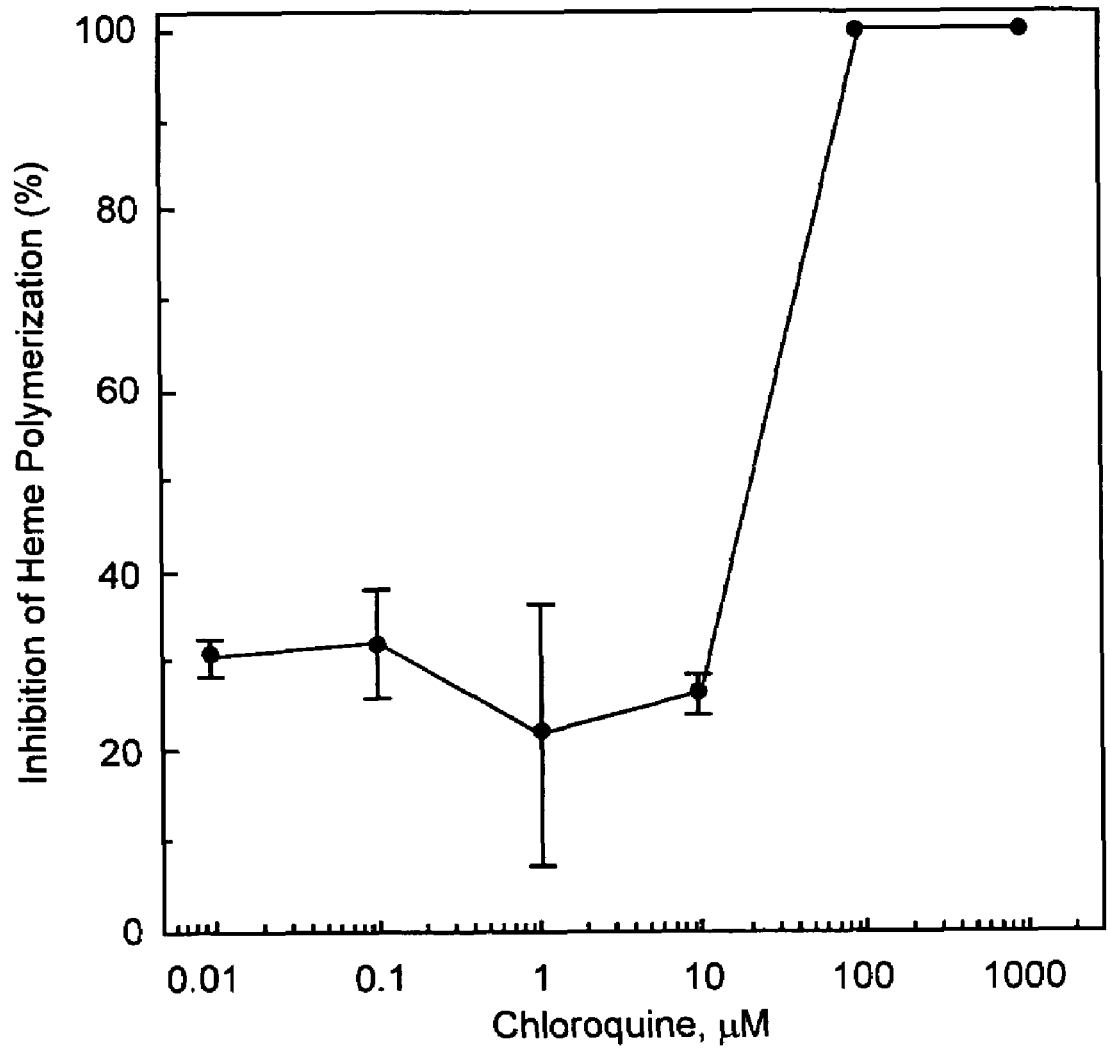
FIG. 14. Inhibition of FRAP-mediated hemozoin formation by Chloroquine. Hemozoin formation was investigated in the absence or presence of different concentrations of chloroquine, an antimalarial drug with high affinity for heme. Chloroquine inhibited heme polymerization in a dose dependent manner. This indicates that blocking FRAP-Heme interaction could serve as an effective antimalarial strategy.

A time kinetic analysis for hemozoin formation revealed that the conversion of heme into hemozoin was complete within hours and was pH dependent where a pH of 5.2 was required for optimal activity (FIG. 12). Stoichiometric analysis for FRAP-Heme interaction using continuous variation method (Job's Plot) revealed that the protein has a 1:1 stoichiometry with heme (FIG. 13). Hemozoin formation could be effectively inhibited by chloroquine, an antimalarial that is known to exerts its activity by binding to free heme and preventing its polymerization into hemozoin (FIG. 14).

These results clearly demonstrate that (i) FRAP is responsible for neutralization of heme through a polymerase activity and (ii) the polymerization can be inhibited by chloroquine. In addition, the active site residues that are critical for this activity were identified. Therefore, FRAP is an efficient drug target for malaria drug development, for example, for the design of small molecules that bind to the active site and inhibit the catalytic capability of FRAP.

REFERENCES FOR EXAMPLE 3

1. Francis, S. E., Sullivan, D. J., Jr. and Goldberg, D. E. (1997) *Annu Rev Microbiol,* 51, 97-123.
2. Gluzman, I. Y., Francis, S. E., Oksman, A., Smith, C. E., Duffin, K. L. and Goldberg, D. E. (1994) *J Clin Invest,* 93, 1602-1608.
3. Pagola, S., Stephens, P. W., Bohle, D. S., Kosar, A. D. and Madsen, S. K. (2000) *Nature,* 404, 307-310.
4. Slater, A. F. and Cerami, A. (1992) *Nature,* 355, 167-169.
5. Slater, A. F., Swiggard, W. J., Orton, B. R., Flitter, W. D., Goldberg, D. E., Cerami, A. and Henderson, G. B. (1991) *Proc Natl Acad Sci USA,* 88, 325-329.
6. Sullivan, D. J., Jr., Gluzman, I. Y. and Goldberg, D. E. (1996) *Plasmodium* hemozoin formation mediated by histidine-rich proteins. *Science,* 271, 219-222.
7. Wellems, T. E., Walker-Jonah, A. and Panton, L. J. (1991) *Proc Natl Acad Sci USA,* 88, 3382-3386.

Example 4

Use of FRAP in High Through Put Assays for Hemozoin Formation for Screening Novel Antimalarials As described above, the pathway for conversion of heme to hemozoin is a major drug target. Until now, in vitro screening of small molecules capable of this blockage has been performed by evaluating their activity in an assay of hemozoin formation, where polymerization is being performed using parasite lysate or is chemically driven requiring extremely high salt concentrations. These conditions, though yielding hemozoin, are far from perfect as a typical experiment requires a 16 hour reaction and less than 10% of the substrate is converted into a product (Tripathi et al., 2004). Our FRAP-based methodology of hemozoin formation is extremely superior to the currently available technology, as it mimics the in vivo process, converts >50% of the initial substrate into product and can be completed in as little as 5 hours. Therefore, a FRAP-based assay system for the identification of antimalarials is an assay system of choice for these processes.

Screening Procedure for Inhibitors of FRAP-Mediated Hemozoin Formation.

The first assay describes in detail how the hemozoin formation is investigated. This is the complete detail of the assay documenting every step of the process. This assay will be used for studying the role of an inhibitor, as inhibition of FRAP activity will cause a decrease in hemozoin formation which will b easily quantifiable by this assay. This assay was used to inhibit hemozoin formation using chloroquine and has been described as assay 2.

Assay 1: FRAP-Mediated Hemozoin Formation Assay (All Temperatures in Degree C.):

The standard assay contained in a total volume of 1.0 ml: 500 mM sodium acetate pH 5.2, 300 nmol/ml hemin-Cl (as substrate) and 500 pmol/ml FRAP, as the source of heme polymerase activity. The amount of FRAP added was chosen such that 50% of the substrate was converted into product (insoluble hemozoin) during the assay. The reaction was initiated by protein addition and allowed to proceed for 16 hours at 37 degree. The reaction was terminated by adding 0.01 ml of 10% SDS solution. The reaction tube was centrifuged at 13,000 rpm for 15 minutes at 23 degrees and the supernatant was carefully removed. The pellet, which contained the polymerized and insoluble hemozoin, was resuspended in 1 ml of 0.1 M sodium bicarbonate pH 9.1 containing 2.5% SDS. At this step, any free heme present in the pellet will go into the solution at it is soluble in sodium bicarbonate while the hemozoin is insoluble. This process essentially removes any free heme that could be present in the pellet. The suspension was spun at 13,000 rpm and the supernatant, containing unpolymerized substrate was removed. This process was repeated thrice, followed by washing of the pellet in pure water. The pellet obtained after final washing was dissolved in 0.3 ml of 0.1 N NaOH and the absorbance of the solution was measured at 405 nm using a spectrophotometer. Amount of heme polymerized was calculated utilizing a standard curve, prepared by dissolving known amounts of commercially available beta-hematin in 0.1 N NaOH. Chemically synthesized beta-hematin and biologically polymerized hemozoin are chemically identical (Pagola et al, 2000 *Nature*).

To assure that the heme polymerized was due specifically to the action of FRAP, a parallel control incubations were performed which either did not contain any protein or contained bovine serum albumin, which was used a non-specific protein control. Furthermore, the hemozoin formation was also evaluated with truncated variants and point mutants of FRAP to not only describe its structural requirements, but also pin point the residues that are involved in the polymerization process.

Assay 2: Inhibition of FRAP-Mediated Hemozoin Formation

For inhibition studies, the inhibitor under examination was added to the standard assay cocktail (as described above) at the desired concentration and the FRAP-mediated hemozoin formation activity was compared to that found in control (minus inhibitor) incubations which lacked inhibitor.

This assay system will be utilized for screening FRAP inhibitors. A difference in the amount of hemozoin seen in the presence of an inhibitor with respect to the reaction where the inhibitor was absent is directly attributable to the activity of the inhibitor in the reaction.

Example 5

SiRNA Mediated Inhibition of FRAP Activities and Genetic Mechanisms that can Downregulate FRAP Expression Leading to Malaria Control.

Gene knockout experiments were performed for FRAP to study its criticality in the life of the parasite. DNA encoding a short segment of FRAP was cloned into a vector encoding the gene for Dihydrofolate reductase (DHFR) as a selection marker. The resulting plasmid vector was transfected into parasites in culture, and the parasites were then subjected to drug pressure (e.g. Drug WR99210) to select for parasites that do not encode a functional FRAP gene. Deletion of FRAP from the genome led to the death of the parasites indicating that (i) this gene is critical for the survival of the parasite and (ii) any strategy that can either prevent the expression of the FRAP gene product or decrease its level of expression can be exploited for controlling malaria. This result also gains credence from the biological role of this protein described by inventors where they have shown that the protein is involved in the infectivity process and in neutralization of heme, which is critical for the survival of the parasite. Therefore, methods that can neutralize the FRAP gene product will automatically lead to malaria control.

In the last few years, inhibition of a gene flinction by utilizing small inhibitory RNA (siRNA) has been shown to be feasible for a variety of pathogens. This technology has proved to be extremely effective in Trypanosome parasites, where it has been extensively utilized for understanding the role of a particular gene in the infectivity process and pathogenicity (Best et al., 2005; Ullu et al., 2002). As deletion of FRAP from the genome is lethal, and the protein plays an important role in the disease process, therefore, siRNA mediated gene silencing can be an effective method for controlling malaria. This is achieved by designing short segments of sense and anti-sense RNA fragments that are complementary to the coding sequence of FRAP. These sequences are delivered to the cytosol of the parasite through a plasmid DNA construct. Once in the cytosol, transcription of the siRNA occurs and prevents the expression of FRAP. The result is loss of the activity of this critical protein, without which the parasite is not able to survive.

For example, human *Plasmodium* parasites can be transformed with vectors expressing one or more siRNA molecules based on SEQ ID NOS: 2 or 8. Methods for design of siRNA molecules have been published by a number of sources. A recent publication by Dharmacon Inc. (Reynolds, A. et al., Rational design for RNA interference (2004), Nature Biotechnology 22: 326-330) suggests eight design criteria optimal for effective siRNA design. The siDESIGN™ Center Program provided by Dharmacon Inc. can be used to design optimal siRNA molecules based on the SEQIDs 2 or 8, that have one or more of the following features: have low G/C nucleotide content (30-52% G/C); three or more A/U nucleotides at the 3'-terminus of the sense strand (the mRNA coding strand); a lack of internal repeats that can form secondary structures; and sequence-specific preferences at the following positions on the sense strand—an A at position 19, an A at position 3, a U at position 10, and an absence of a G or C at position 19 and a G at position 13. The resulting siRNA oligonucleotides can be cloned as a small hairpin RNAs (shRNA) between a *Plasmodium* RNA Polymerase mi (Pol III) promoter, which initiates synthesis at a defined distance from the promoter, and a termination sequence consisting of a string of 4-5 uridines, or other suitable constitutive promoters can be used as well. When transfected and co-expressed with a selectable marker into *Plasmodium* cells, siRNA expression will reduce the levels of the endogenous mRNAs corresponding to SEQ ID 2 or 8.

Several sources are available which give detailed descriptions of the use of siRNA technology. For example, WO0044895 (Kreutzer and Limmer) specifically covers the use of small dsRNAs as therapeutics, and specifically to methods and medicaments involving the use of small dsRNAs formed from two separate strands and having a region complementary to the target gene.

US2005026278 (Tuschl et al.) describes a key structural feature of siRNAs, namely the presence of overhangs at the 3'-end of each of the two strands and includes data on mammalian cell gene silencing. U.S. Pat. Nos. 5,898,031 and 6,107,094 (the entire contents of which are hereby incorporated by reference) describe degradation of target MRNA mediated by chemically modified RNAi-like oligonucleotides.

Example 6

A Variant of FRAP that Leads to Attenuated Parasites, which can be Used as a Whole Organism Vaccine We have successfully demonstrated that FRAP performs the critical neutralization of toxic heme into non-toxic hemozoin. We have also identified amino acids in FRAP, whose conversion result in protein variants in which the heme polymerase activity has been totally lost or has been compromised (Table 7). Developing a parasite which has been genetically modified in such a way, where the FRAP gene is present in the genome, but it has been modified by a genetic modification to a variant copy of the protein, which encodes a protein that is not fully functional, will give rise to attenuated parasites. Such a process has been previously demonstrated in other systems where CSP, a gene encoding a parasite protein involved in pathogenesis was swapped by genetic manipulation resulting in attenuated parasites (Tewari et al., 2005). Attenuated parasites may also be produced using siRNA vectors as described in the section above.

Example 7

Use of FRAP as a Tool for High Expression of Recombinant Proteins and Subsequent Purification As described in Example 1, expression of DNA encoding FRAP in *E. coli* leads to very high expression and up to 40 mg of purified protein can be purified from a one liter shaker flask culture. Obtaining high yields for a recombinant protein and development of optimal purification strategies has long been recognized as a major bottleneck for developing therapeutics. In the field of recombinant protein expression and purification, these issues have been tackled by expressing a gene of interest fused with a second gene (commonly called as a tag), which has distinct binding properties and a high level of expression. The two most commonly utilized tags for such purposes are DNA encoding for maltose-binding protein and glutathione S transferase. These tags not only facilitate purification of protein by exploiting the distinct binding properties of the tags but also help by enhancing the expression of the gene of interest.

The high level of expression of FRAP in its recombinant expression and its unique capabilities of interaction with heme makes this protein uniquely fitted to serve as a tag in recombinant expression vectors. FRAP-based fusions proteins are purified by affinity chromatography by exploiting its heme-binding properties in a column chromatography system, where the fusion protein binds to the column through available heme moiety and is eluted by excess of free heme. Various fusion proteins of FRAP having epitopes of CSP and TRAP may be produced by this method for use, e.g. in a vaccine.

REFERENCES FOR EXAMPLES 4-7

Best, A., Handoko, L., Schluter, E. and Goringer, H. U. (2005) *J Biol Chem,* 280, 20573-20579.

Tewari, R., Rathore, D. and Crisanti, A. (2005) *Cell Microbiol,* 7, 699-707.

Tripathi, A. K., Khan, S. I., Walker, L. A. and Tekwani, B. L. (2004) *Anal Biochem,* 325, 85-91.

Ullu, E., Djikeng, A., Shi, H. and Tschudi, C. (2002) RNA interference: advances and questions. *Philos Trans R Soc Lond B Biol Sci,* 357, 65-70.

Example 8

Production of Fully Human Antibodies

Fully human monoclonal antibodies against *Plasmodium* or *Theileria* antigens are made in mice directly, when these mice are engineered to produce only human antibody chains. For example the technology practiced by companies such as Abgenix Inc. [XenoMouse technology, U.S. Pat. No. 6,657, 103], Medarex Inc. and GenMab A/S [HuMab Mouse or UltiMAB technology; WO2005023177] can be used. Purified proteins as described above are used to immunize such engineered mice. Monoclonals produced in this manner are produced, screened and characterized in the standard manner. Fully human antibodies are produced using phage display methods by screening against human antibody phage display libraries. For example technologies practiced by companies such as Cambridge Antibody Technology [U.S. Pat. No. 5,969,108 and U.S. Pat. No. 6,172,197] and others, can be used to identify fully human antibodies in this manner. Phage display screening has as an added advantage that the process does not rely on animal immunization. The genes for fully human antibodies produced using engineered mice, or identified through phage display, are isolated, sequenced and cloned for expression in mammalian cell lines for high level expression using standard methods.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. An isolated transfected cell comprising expressable recombinant DNA that encodes a polypeptide comprising the amino acid sequence set forth as SEQ ID NO: 1, SEQ ID NO: 24, SEQ ID NO: 25, or SEQ ID NO: 37, wherein said amino acid sequence is encoded by a nucleic acid sequence set forth as SEQ ID NO: 2, SEQ ID NO: 39, SEQ ID NO: 26, or SEQ ID NO: 38, respectively.

2. A method for expression and purification of a recombinant protein, comprising the step of providing a vector that operably encodes said recombinant protein, wherein said recombinant protein comprises the amino acid sequence set forth as SEQ ID NO:1, and wherein said amino acid sequence is encoded by the nucleic acid sequence, SEQ ID NO: 2.

3. The method of claim 2, wherein said recombinant protein is a fusion protein.

4. The method of claim 2, wherein said recombinant protein further comprises one or more copies of amino acid sequence set forth as SEQ ID NO: 24, SEQ ID NO: 25 or SEQ ID NO: 37, wherein said amino acid sequence is encoded by nucleic acid sequence set forth as SEQ ID NO: 39, SEQ ID NO: 26 or SEQ ID NO: 38, respectively.

5. The method of claim 2, wherein said vector further encodes an antigen selected from the group consisting of Circumsporozoite protein (CSP) and Thrombospondin-related anonymous protein (TRAP).

6. A composition for eliciting an immune response to *Plasmodium*, comprising the nucleic acid sequence encoding the amino acid sequence set forth as SEQ ID NO: 1 or SEQ ID NO: 25, wherein said nucleic acid sequence is SEQ ID NO: 2 or SEQ ID NO: 26.

7. The composition of claim 6, further comprising one or more adjuvants.

8. The composition of claim 6, further comprising a nucleic acid sequence encoding the polypeptides which is not encoded by SEQ ID NO: 2, or SEQ ID NO: 26.

9. The composition of claim 6, wherein said nucleic acid sequence is expressed in a vector.

10. The composition of claim 9, wherein said vector is an adenoviral vector.

11. A composition for eliciting an immune response to *Plasmodium,* comprising a nucleic acid sequence encoding the amino acid sequence set forth as SEQ ID NO: 37, wherein said nucleic acid sequence is SEQ ID NO: 38.

12. The composition of claim 11, wherein said nucleic acid sequence comprises the nucleic acid sequence encoding the amino acid sequence represented by set forth as SEQ ID NO: 24, wherein said nucleic acid sequence is SEQ ID NO: 39.

13. The composition of claim 11, further comprising one or more adjuvants.

14. The composition of claim 11, further comprising a nucleic acid sequence encoding the polypeptides which is not encoded by SEQ ID NO: 38 or SEQ ID NO: 39.

15. The composition of claim 11, wherein said nucleic acid sequence is expressed in a vector.

16. the composition of claim 15, wherein said vector is an adenoviral vector.

* * * * *

UNITED STATES PATENT AND TRADEMARK OFFICE
CERTIFICATE OF CORRECTION

| | |
|---|---|
| PATENT NO. | : 7,438,916 B2 |
| APPLICATION NO. | : 11/249355 |
| DATED | : October 21, 2008 |
| INVENTOR(S) | : Dharmendar Rathore |

Page 1 of 1

It is certified that error appears in the above-identified patent and that said Letters Patent is hereby corrected as shown below:

Column 1 (after the title), lines 4 and 5, delete the heading "STATEMENT OF FEDERALLY SPONSORED RESEARCH AND DEVELOPMENT"

Column 1, lines 6 to 11, delete this paragraph in its entirety

Signed and Sealed this
Twenty-fifth Day of September, 2012

David J. Kappos
*Director of the United States Patent and Trademark Office*